US011440884B2

(12) United States Patent
Burstein et al.

(10) Patent No.: US 11,440,884 B2
(45) Date of Patent: *Sep. 13, 2022

(54) COMPOUNDS, SALTS THEREOF AND METHODS FOR TREATMENT OF DISEASES

(71) Applicant: ACADIA PHARMACEUTICALS INC., San Diego, CA (US)

(72) Inventors: Ethan S. Burstein, San Diego, CA (US); Roger Olsson, Bunkeflostrand (SE); Karl Erik Jansson, Dalby (SE); Niklas Patrik Sköld, Lund (SE); Larisa Yudina Wahlström, Eslöv (SE); Björn Gustav Borgström, Lund (SE); Henrik Von Wachenfeldt, Malmö (SE); Magnus Gustav Wilhelm Bergner, Lund (SE)

(73) Assignee: ACADIA PHARMACEUTICALS INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/640,994

(22) PCT Filed: Aug. 20, 2018

(86) PCT No.: PCT/US2018/000351
§ 371 (c)(1),
(2) Date: Feb. 21, 2020

(87) PCT Pub. No.: WO2019/040104
PCT Pub. Date: Feb. 28, 2019

(65) Prior Publication Data
US 2021/0122713 A1 Apr. 29, 2021

Related U.S. Application Data

(60) Provisional application No. 62/548,317, filed on Aug. 21, 2017.

(51) Int. Cl.
*C07D 211/58* (2006.01)
*C07D 405/04* (2006.01)
*C07D 471/04* (2006.01)

(52) U.S. Cl.
CPC .......... *C07D 211/58* (2013.01); *C07D 405/04* (2013.01); *C07D 471/04* (2013.01); *C07B 2200/05* (2013.01)

(58) Field of Classification Search
CPC ... C07D 211/58; C07D 405/04; C07D 471/04
USPC ....................................................... 514/299
See application file for complete search history.

(56) References Cited

U.S. PATENT DOCUMENTS

| 5,707,798 A | 1/1998 | Brann |
| 7,115,634 B2 | 10/2006 | Thurieau |

| 2004/0106600 A1 | 6/2004 | Andersson et al. |
| 2005/0239796 A1 | 10/2005 | Thurieau et al. |
| 2007/0260064 A1 | 11/2007 | Tolf et al. |
| 2008/0280886 A1 | 11/2008 | Gant et al. |
| 2020/0270239 A1 | 8/2020 | Burstein et al. |

FOREIGN PATENT DOCUMENTS

| CN | 104844502 A | * | 8/2015 | |
| CN | 105481757 A | * | 4/2016 | |
| WO | WO-0166521 A1 | * | 9/2001 | .......... C07D 451/02 |
| WO | WO-2004000808 A2 | | 12/2003 | |
| WO | WO-2004064738 A2 | | 8/2004 | |
| WO | WO-2006036874 A1 | | 4/2006 | |
| WO | WO-2006086705 A1 | | 8/2006 | |
| WO | WO-2008071961 A1 | * | 6/2008 | ............. A61P 31/04 |
| WO | WO-2008141057 A1 | | 11/2008 | |
| WO | WO-2008150089 A1 | * | 12/2008 | ............. A61P 31/04 |
| WO | WO-2009039461 A2 | | 3/2009 | |
| WO | WO-2010111353 A1 | | 9/2010 | |
| WO | WO-2012116176 A2 | | 8/2012 | |
| WO | WO-2015095701 A | * | 6/2015 | .......... C07D 401/04 |
| WO | WO-2017015272 A1 | | 1/2017 | |
| WO | WO-2019040107 A1 | | 2/2019 | |

OTHER PUBLICATIONS

Bhatia et al. A review of Bioisosterism : A rational Approach for Drug Design and Molecular Modification. (Year: 2011).*
Silverman, R.B. The Organic Chemistry of Drug Design and Drug Action 1992, Academic: New York, p. 19.*
Shah "The role of fluorine in medicinal chemistry" Journal of Enzyme Inhibition and Medicinal Chemistry, Oct. 2007; 22(5): 527-540.*
Barnes, N.M., and Sharp T., "A review of central 5-HT receptors and their function," Neuropharmacology 38(8): 1083-1152, Pergamon Press, England (Aug. 1999).
Glennon, R.A., "Serotonin receptors: Clinical implications," Neuroscience and Biobehavioral Reviews 14(1):35-47, Pergamon Press, United States, (1990).
Saltzman, A.G., et al., "Cloning of the human serotonin 5-HT2 and 5-HT1C receptor subtypes," Biochemical and Biophysical Research Communications 181(3):1469-1478, Elsevier, United States, (Dec. 1991).
International Search Report and Written Opinion for International Application No. PCT/US2018/000351, European Patent Office, Netherlands, dated Mar. 15, 2019, 16 pages.
IUPAC-IUB Comm. Biochem. Nomenclature. IUPAC-IUB [International Union of Pure and Applied Chemistry—International Union of Biochemistry] Commission of Biochemical Nomenclature. Abbreviated nomenclature of synthetic polypeptides (polymerized amino acids). Revised recommendations (1971). Biochemistry 11(5): 942-944, (1972).

(Continued)

*Primary Examiner* — David K O'Dell

(74) *Attorney, Agent, or Firm* — Sterne, Kessler, Goldstein & Fox P.L.L.C.

(57) ABSTRACT

The present disclosure relates to compounds according to Formulae (I), (II) and (VIII), useful for treating diseases.

17 Claims, No Drawings

(56) References Cited

OTHER PUBLICATIONS

Meltzer, H.Y., "The role of serotonin in antipsychotic drug action," Neuropsychopharmacology 21(2 Suppl):106S-115S, Elsevier Science Group, United States (Aug. 1999).
Prabhakaran, J., et al., "Synthesis and in vivo evaluation of [O-methyl-11C] 2-(4-methoxyphenyl)-N-(4-methylbenzyl)-N-( 1-methyl-piperidin-4-yl)acetamide as an imaging probe for 5-HT2A receptors," Journal of Labelled Compounds and Radiopharmaceuticals 49(12):1069-1077, John Wiley & Sons, United States (Oct. 2006).
Cheng, Y., et al., "Relationship between the inhibition constant ($K_1$) and the concentration of inhibitor which causes 50 per cent inhibition ($I_{50}$) of an enzymatic reaction," Biochemical Pharmacology 22(23):3099-3108, Pergamon Press, Great Britain (Dec. 1973).
Fuller, R.W., "Drags acting on serotonergic neuronal systems," in Biology of Serotonergic Transmission, N. N. Osborne, ed., pp. 221-247, Wiley, New York, United States (1982).
Nogrady, T., "Principles of Drug Design," in Medicinal Chemistry: A Biochemical Approach. pp. 375-394, Oxford University Press, New York, United States (1985).
Saxena, P.R., et al., "Cardiovascular effects of serotonin agonists and antagonists," Journal of Cardiovascular Pharmacology and Therapeutics 15 Suppl 7:S17-S34, Raven Press, Ltd. New York (1990).
Notice of Allowance dated Nov. 8, 2021. U.S. Appl. No. 16/797,611, Burstein, E.S., et al., filing date Feb. 21, 2020, 9 pages.
Office Action dated Apr. 28, 2021, U.S. Appl. No. 16/797,611, Burstein. E.S., et al., filing date Feb. 21, 2020, 12 pages.
Notice of Allowance dated Feb. 28, 2022, U.S. Appl. No. 16/797,611, Burstein, E.S., et al., filed Feb. 21, 2020, 8 pages.
Duan, M., et al., "Discovery of a novel series of cyclic urea as potent CCR5 antagonists," Bioorganic & Medicinal Chemistry Letters 21:6381-6385, Elsevier Ltd. (2011).

* cited by examiner

COMPOUNDS, SALTS THEREOF AND METHODS FOR TREATMENT OF DISEASES

FIELD

Provided herein are compounds and their pharmaceutically acceptable salts for treatment of diseases and conditions associated with the serotonin receptor 5-HT.

BACKGROUND

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, *Rev. Neurol.* 150:3-15, (1994)). Peripheral functions in the cardiovascular, hematological and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, Biology of Serotonergic Transmission, 1982; Boullin, *Serotonin In Mental Abnormalities* 1:316 (1978); Barchas, et al., *Serotonin and Behavior*, (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et al., *The Peripheral Actions of 5-Hydroxytryptamine*, 246 (1989); Saxena, et al., *J. Cardiovascular Pharmacol.* 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 14 genetically distinct 5-HT receptor subtypes have been identified and assigned to one of seven families (5-HT1-7). Each subtype displays a unique distribution, preference for various ligands, and functional correlate(s).

Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, *Neuropsychopharmacology*, 21:106S-115S (1999); Barnes & Sharp, *Neuropharmacology*, 38:1083-1152 (1999); Glennon, *Neurosci. Biobehavioral Rev.*, 14:35 (1990)).

Given the broad distribution of serotonin within the body and its role in a wide range of physiological and pathological processes, it is understandable that there is tremendous interest in drugs that affect serotonergic systems (Gershon, et al., *The Peripheral Actions of 5-Hydroxytryptamine*, 246 (1989); Saxena, et al., *J. Cardiovascular Pharmacol.* 15: Supp. 7 (1990)).

The effects of serotonin are mediated by at least 14 genetically distinct 5-HT receptor subtypes have been identified and assigned to one of seven families (5-HT1-7). Each subtype displays a unique distribution, preference for various ligands, and functional correlate(s). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes. The high degree of genetic and pharmacological homology between these receptor subtypes has hampered the development of subtype-selective compounds, as well as the determination of the normal physiologic or pathophysiologic role of any particular receptor subtype. Thus there is a need to develop drugs that are selective for individual receptor classes and subclasses amongst monoaminergic neurotransmitter receptors.

The prevailing theory for the mechanism of action of antipsychotic drugs involves antagonism of dopamine D2 receptors. Unfortunately, it is likely that antagonism of dopamine D2 receptors also mediates the extrapyramidal side effects as well as some additional undesired effects of antipsychotic therapies such as a worsening of depression symptoms, anhedonia and impairment of cognitive processes. Antagonism of 5-HT2A receptors is an alternate molecular mechanism for drugs with antipsychotic efficacy, possibly through antagonism of heightened or exaggerated signal transduction through serotonergic systems. 5-HT2A antagonists are therefore good candidates for treating psychosis without extrapyramidal side effects or other undesired effects associated with blockade of dopamine D2 receptors.

Traditionally, GPCRs such as the 5-HT2A receptor have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they alone can activate or inactivate these molecules, respectively. In contrast, classic or neutral antagonists compete against agonists and inverse agonists for access to the receptor, but do not possess the intrinsic ability to inhibit elevated basal or constitutive receptor responses.

Consequently there is a need of new compounds for making antipsychotic drugs that target serotonin receptors.

SUMMARY

Provided herein are compounds according to Formulas (I)-(II),

Provided herein is a compound according to Formula (I)

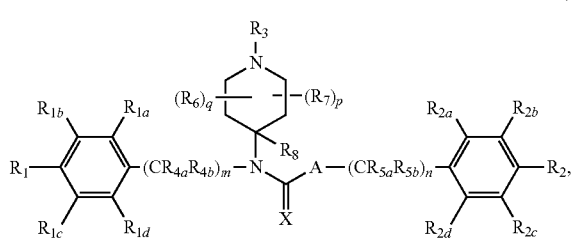

(I)

or a pharmaceutically acceptable salt, hydrate, solvate, polymorph, prodrug, stereoisomer, and deuterated analogue thereof, wherein:

m, and n are independently an integer selected from the group consisting of 0, 1, 2, and 3;

p, and q are independently an integer selected from the group consisting of 0, 1, 2, 3, and 4;

$R_1$, $R_{1a}$, $R_{1b}$, $R_{1c}$ and $R_{1d}$ are independently selected from the group consisting of hydrogen, deuterium, hydroxyl, —OD, halogen, cyano, amino, —S(=O)$_2$R$_{10}$, —OC(=O)R$_{11}$, —C(=O)OR$_{11}$, unsubstituted or substituted C$_{1-6}$ alkyl, unsubstituted or substituted C$_{1-6}$ haloalkyl, unsubstituted or substituted C$_{1-6}$ hydroxyalkyl, unsubstituted or substituted C$_{1-6}$ aminoalkyl, unsubstituted or substituted C$_{2-6}$ alkenyl, unsubstituted or substituted C$_{1-6}$ alkoxy, unsubstituted or substituted C$_{3-6}$ cycloalkyl, unsubstituted or substituted C$_{3-6}$ heteroalicyclyl, substituted or unsubstituted aryl, and substituted or unsubstituted heteroaryl, wherein at least one of $R_1$, $R_{1a}$, $R_{1b}$, $R_{1c}$ and $R_{1d}$ is not hydrogen, wherein $R_{10}$ and $R_{11}$, independently are selected from the group consisting of hydrogen, amino, unsubstituted or substituted C$_{1-6}$ alkyl;

$R_2$, $R_{2a}$, $R_{2b}$, $R_{2c}$ and $R_{2d}$ are independently selected from the group consisting of hydrogen, deuterium, amino, hydroxyl, —OD, halogen, cyano, unsubstituted or substituted C$_{1-6}$ alkyl, unsubstituted or substituted C$_{1-6}$ haloalkyl, unsubstituted or substituted C$_{1-6}$ hydroxyalkyl, unsubstituted or substituted C$_{2-6}$ alkenyl, unsubstituted or substituted C$_{1-6}$ alkoxy, unsubstituted or substituted C$_{3-6}$ cycloalkyl, unsubstituted or substituted C$_{3-6}$ heteroalicyclyl, substituted or unsubstituted aryl, and substituted or unsubstituted heteroaryl, wherein at least one of $R_2$, $R_{2a}$, $R_{2b}$, $R_{2c}$ and $R_{2d}$ is not hydrogen, or $R_2$ and $R_{2b}$ or $R_{2c}$, taken together with the atoms to which they are attached form a ring system;

$R_3$ is selected from the group consisting of hydrogen, deuterium, hydroxyl, —OD, unsubstituted or substituted C$_{1-6}$ alkyl, unsubstituted or substituted C$_{1-6}$ haloalkyl, unsubstituted or substituted C$_{1-6}$ hydroxyalkyl, unsubstituted or substituted C$_{2-6}$ alkenyl, unsubstituted or substituted C$_{3-6}$ cycloalkyl, unsubstituted or substituted C$_{3-6}$ heteroalicyclyl, substituted or unsubstituted aryl, and substituted or unsubstituted heteroaryl; or $R_3$, the nitrogen to which $R_3$ is attached and a carbon atom adjacent to the nitrogen taken together with $R_6$ or $R_7$ form a heteroalicyclic ring system;

$R_{4a}$, $R_{4b}$, $R_{5a}$, and $R_{5b}$, are independently selected from the group consisting of hydrogen, deuterium, and unsubstituted or substituted C$_{1-6}$ alkyl;

$R_6$ is selected from the group consisting of hydrogen, deuterium, halogen, hydroxyl, oxo, —OD, cyano, substituted or unsubstituted C$_{1-4}$ alkyl, and substituted or unsubstituted C$_{1-4}$ alkoxy, substituted or unsubstituted aryl;

$R_7$ is selected from the group consisting of hydrogen, deuterium, halogen, hydroxyl, oxo, —OD, cyano, substituted or unsubstituted C$_{1-4}$ alkyl, and substituted or unsubstituted C$_{1-4}$ alkoxy;

$R_8$ is absent, or selected from the group consisting of hydrogen, deuterium, cyano, hydroxyl, —OD, substituted or unsubstituted C$_{1-4}$ alkyl, substituted or unsubstituted C$_{2-4}$ alkenyl, substituted or unsubstituted C$_{3-6}$ cycloalkyl, and substituted or unsubstituted C$_{1-4}$ alkoxy;

A is a bond, —S— or —O—, and —CH=CH—; wherein if A is —CH=CH—, n is 0; and X is O or S.

In certain embodiments, the compound of Formula (I) is not N-(2,4-difluorobenzyl)-2-(4-methoxyphenyl)-N-(piperidin-4-yl)acetamide.

Provided herein is also a method for treating a disease in a patient comprising administering to the patient an effective amount of a compound, pharmaceutically acceptable salt, polymorph or stereoisomer of a compound according to Formula (I), wherein the disease is selected from the group consisting of Abnormal hormonal activity, Alzheimer's disease, Alzheimer's disease dementia, Alzheimer's disease psychosis, Addiction (alcohol, cocaine, methamphetamine, nicotine and opioid), Addison's disease, ADHD, Alzheimer's disease psychosis, Affective disorders, Aggressiveness, Agitation, Akathisia, Alcohol addiction, Alcohol withdrawal, Amenorrhea, Amyotrophic lateral sclerosis, Anhedonia, Anorexia, Anti-NMDAR encephalitis, Anxiety, Appetite disorders, Asthma, Autism, Behavioral disorders, Behavioral disturbances associated with dementia, Binge eating disorder associated with impulse control disorder (ICD), Bipolar disorder, Blindness, Borderline disorder, Borderline personality disorder, Bradykinesia, Bulimia, Buying associated with ICD, Cardiac arrhythmia, Cerebral vascular accidents, Charles Bonnet disease, Chemotherapy-induced emesis, Childhood autism, Chronic pain, Chronic insomnia, cocaine addiction, Cognitive disorders, craniofacial pain, temporomandibular joint (TMJ)/temporomandibular disorder (TMD), Cushing's disease, Delusion, Dementia, Dementia with Lewy Body or Lewy Body dementia, dementia and psychosis associated with Creutzfeld-Jakob disease (CJD), Gerstmann-Strausser-Schenker disease (GSSD) and fatal familial insomnia (FFI), Depression, Diabetes mellitus (non-insulin dependent), Diabetic peripheral neuropathy, Drug addiction, Double vision, Down's syndrome, Dyskinesia, Dysthymia, Dystonia, Ejaculatory problem, Emphysema, Epilepsy, Extrapyramidal disorder, Fibromyalgia, Frailty, Friedrich's Ataxia, Frontotemperal Dementia, Gambling associated with ICD, Galactorrhea, General anxiety disorder, Glaucoma, Hair loss or thinning, Hallucination, Headache, Hemorrhoids, Huntington's disease, Hyperprolactinemia, Hypertension, Hypersexuality associated with ICD, Hypotension, Hypoglutamateriga disorders, Impulse control disorder, Idiopathic thrombocytopenic purpura, Impotence, Incontinence, Increased intraocular pressure, Infertility, Inflammatory pain, Insomnia, Ischemia, Ischemic stroke, Lewy body disease (LBD), Learning disorders, Libido (decreased), Loss of libido, Low male fertility, Low sperm mobility, Lupus, Machado-Joseph disease, Major depression, Mania, Menopausal symptoms, Metabolic syndrome, methamphetamine addiction, Migraine, mild cognitive impairment (MCI), Motor tics, Multi-infarct dementia, Multiple sclerosis, Multiplex development disorder, Myocardial infarction, Myoclonus, Neuropathic pain, Neurodegenerative disorder, Neuropsychiatric disease, Nicotine addiction, Non motor symptoms of Parkinson's disease selected from dementia, depression, apathy, hallucinations, dribbling saliva (sialorrhea), constipation, pain, genitourinary problems and sleep disorders, Obsessive compulsive disorder, On/off phenomena, Opioid addiction, Osteoporosis, Pancreatis, Panic attacks, Parkinson's disease, Parkinson's disease dementia, Parkinson's disease psychosis, Periodic limb movement during sleep (PLMS), Peripheral vascular disease, Pituitary tumor, Postherpetic neuralgia, Progressive Supranucelar Palsy, Prion disease including Creutzfeld-Jakob disease (CJD), Gerstmann-Strausser-Schenker disease (GSSD) and fatal familiar insomnia (FFI), Prolactinoma, Pseudobulbar affect (PBA), Psychomotor slowing, Psychosis, Psychoses secondary to neurodegenerative disorders, Psychosomatic disorders, Psychotic depression, post-traumatic stress disorder (PTSD), Raynaud's disease, Reflex sympathetic dystrophy, Restless legs syndrome, Retinal disease, Schizoaffective disorders, Schizophrenia, negative symptoms of schizophrenia, cognitive impairment associated with schizophrenia, Sepsis, Serotonin syndrome, Sexual dysfunction, Sexual dysfunction associated with antidepressant use, Sleep apnea, Sleep disorders, Sleep maintenance insomnia, social anxiety disorder, Spinal injury, Spinocerebellar Atrophy, Suicidal tendency, Thrombosis, Thrombotic stroke, Thrombotic thrombocytopenic purpura, Tinnitus, Tiredness, Tourette's syndrome, Transient insomnia, Traumatic brain injury, Treatment-resistant depression, Treatment-resistant schizophrenia, Tremor, Vaginal dryness, Vasospasm Wakefulness, vascular dementia, Hallucinations associated with Parkinson's disease, Delusions associated with Parkinson's disease; cancer, brain cancer, glioma, Pancreatic cancer, Hypoactive sexual desire disorder, adult type 2 diabetes mellitus with Parkinson's disease or dementia and Liver fibrosis.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety. In the event that there are a plurality of definitions for a term herein, those in this section prevail unless stated otherwise.

As used herein, any "R" group(s) such as, without limitation, $R_1$, $R_2$, $R_3$, $R_4$, $R_5$, $R_6$, $R_7$, $R_8$, $R_9$, and $R_{10}$, represent substituents that can be attached to the indicated atom. A non-limiting list of R groups includes but is not limited to hydrogen, alkyl, alkenyl, alkynyl, cycloalkyl, cycloalkenyl, cycloalkynyl, aryl, heteroaryl, and heteroalicyclyl. If two "R" groups are covalently bonded to the same atom or to adjacent atoms, then they may be "taken together" or "combined" as defined herein to form a cycloalkyl, aryl, heteroaryl or heteroalicyclyl group. For example, without limitation, if $R_a$ and $R_b$ of an $NR_aR_b$ group are indicated to be "taken together" or "combined", it means that they are covalently bonded to one another at their terminal atoms to form a ring that includes the nitrogen:

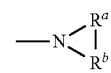

As readily recognized by the skilled person, any given atom with unsatisfied valences disclosed in the text, formulas, schemes, examples and figures herein is assumed to have a sufficient number of hydrogen atoms to satisfy the valency.

Whenever a group is described as being "unsubstituted or substituted," if substituted, the substituent(s) (which may be present one or more times, such as 1, 2, 3 or 4 times) are independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

When a substituent on a group is deemed to be "substituted," the substituent itself is substituted with one or more of the indicated substituents. When the referenced substituent is substituted, it is meant that one or more hydrogen atoms on the referenced substituent may be replaced with a group(s) individually and independently selected from deuterium, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. The protecting groups that may form the protective derivatives of the above substituents are known to those of skill in the art and may be found in references Greene and Wuts, Protective Groups in Organic Synthesis, $3^{rd}$ Ed., John Wiley & Sons, New York, N.Y., 1999, which is hereby incorporated by reference in its entirety.

Whenever a group, such as an "unsubstituted or substituted" alkyl group, is described without the use of "unsubstituted or substituted", e.g. "alkyl" it is understood as an "unsubstituted alkyl", unless the group is separately defined herein to be able to carry substituents. For example $C_{1-6}$ alkyl means an unsubstituted alkyl comprising 1 to 6 carbon atoms.

As used herein, "$C_m$ to $C_n$," "$C_n$-$C_n$" or "$C_{m\text{-}n}$" in which "m" and "n" are integers refers to the number of carbon atoms in the relevant group. That is, the group can contain from "m" to "n", inclusive, carbon atoms. Thus, for example, a "$C_1$ to $C_6$ alkyl" group refers to all alkyl groups having from 1 to 6 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH)_3CH_2$—, $CH_3CH(CH)_3CH_2$— and $(CH_3)_3C$—. If no "m" and "n" are designated with regard to a group, the broadest range described in these definitions is to be assumed.

As used herein, "alkyl" refers to a straight or branched hydrocarbon chain group that is fully saturated (no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms, such as "$C_{1-6}$". The alkyl group could also be a lower alkyl having 1 to 4 carbon atoms. The alkyl group of the compounds may be designated as "$C_1$-$C_4$ alkyl," "Ca alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, the term "optionally", for example "optionally deuterated" means that group may be unsubstituted or substituted with one or more of the indicated substituents, e.g. one or more hydrogen(s) may be replaced by one or more deuterium(s).

As used herein, "alkenyl" refers to an alkyl group that contains in the straight or branched hydrocarbon chain one or more double bonds. If more than one double bond is present, the double bonds may be conjugated or not conjugated. The alkenyl group may have 2 to 20 carbon atoms (whenever it appears herein, a numerical range such as "2 to 20" refers to each integer in the given range; e.g., "2 to 20 carbon atoms" means that the alkenyl group may consist of 2 carbon atoms, 3 carbon atoms, 4 carbon atoms, etc., up to and including 20 carbon atoms, although the present definition also covers the occurrence of the term "alkenyl" where no numerical range is designated). When substituted, the substituent group(s) is(are) one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, mercapto, alkylthio, cyano, halogen, nitro, haloalkyl, haloalkoxy, and amino, including mono- and di-substituted amino groups, and the protected derivatives thereof.

As used herein, "alkynyl" refers to an alkyl group that contains in the straight or branched hydrocarbon chain one or more triple bonds. The alkynyl group may have 2 to 20 carbon atoms (whenever it appears herein, a numerical range such as "2 to 20" refers to each integer in the given range; e.g., "2 to 20 carbon atoms" means that the alkynyl group may consist of 2 carbon atoms, 3 carbon atoms, 4 carbon atoms, etc., up to and including 20 carbon atoms, although the present definition also covers the occurrence of the term "alkynyl" where no numerical range is designated). An alkynyl group may be unsubstituted or substituted. When substituted, the substituent(s) may be selected from the same groups disclosed above with regard to alkenyl group substitution.

As used herein, "hetero" refers to heteroatoms selected from nitrogen, oxygen, phosphorus and sulfur.

As used herein, "heteroalkyl," by itself or in combination with another term, refers to a straight or branched alkyl group consisting of the stated number of carbon atoms, where one or more carbon atom(s), such as 1, 2, 3 or 4 carbon atom(s), and the associated hydrogen atom(s) have been independently replaced with the same or different heteroatoms selected from nitrogen, oxygen and sulfur. The carbon atom(s) being replace may be in the middle or at the end of the alkyl group. Examples of heteroalkyl include, but are not limited to, —S-alkyl, —O-alkyl, —NH-alkyl, -alkylene-O-alkyl, etc As used herein, "aryl" refers to a carbocyclic (all carbon) ring or two or more fused rings (rings that share two adjacent atoms) that have a fully delocalized pi-electron system. Examples of aryl groups include, but are not limited to, benzene, naphthalene and azulene. An aryl group may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to a monocyclic or multicyclic aromatic ring system (a ring system with fully delocalized pi-electron system), in which at least one of the atoms in the ring system is a heteroatom, that is, an element other than carbon, including but not limited to, nitrogen, oxygen and sulfur. Examples of monocyclic "heteroaryl" include, but are not limited to, furan, thiophene, phthalazine, pyrrole, oxazole, thiazole, imidazole, pyrazole, isoxazole, isothiazole, triazole, thiadiazole, pyridine, pyridazine, pyrimidine, pyrazine, tetrazole, oxadiazole, and triazine. Examples of multicyclic "heteroaryl" include, but are not limited to, quinoline, isoquinoline, quinazoline, quinoxaline, indole, purines, benzofuran, benzothiophene, benzopyranones (e.g. coumarin, chromone, and isocoumarin). A heteroaryl may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on a heteroaryl group may form a non-aromatic ring fused to the aryl group, including a cycloalkyl, cycloalkenyl, cycloalkynyl, and heterocyclyl.

An "aralkyl" or "arylalkyl" is an aryl group connected, as a substituent, via an alkylene group. The alkylene and aryl group of an aralkyl may be substituted. Examples include but are not limited to benzyl, substituted benzyl, 2-phenylethyl, 3-phenylpropyl, and naphthylalkyl. In some cases, the alkylene group is a lower alkylene group.

A "heteroaralkyl" or "heteroarylalkyl" is heteroaryl group connected, as a substituent, via an alkylene group. The alkylene and heteroaryl group of heteroaralkyl may be substituted. Examples include but are not limited to 2-thienylmethyl, 3-thienylmethyl, furylmethyl, thienylethyl, pyrrolylalkyl, pyridylalkyl, isoxazolylalkyl, pyrazolylalkyl and imidazolylalkyl, and their substituted as well as benzo-fused analogs. In some cases, the alkylene group is a lower alkylene group.

An "alkylene" is a straight-chained tethering group, forming bonds to connect molecular fragments via their terminal carbon atoms. The alkylene may have 1 to 20 carbon atoms. The alkylene may also be a medium size alkylene having 1 to 10 carbon atoms, such as "$C_{1-6}$." The alkylene could also be a lower alkylene having 1 to 4 carbon atoms. The alkylene may be designated as "$C_1$-$C_4$ alkylene", "$C_{1-4}$ alkylene" or similar designations. Non-limiting examples include, methylene (—$CH_2$—), ethylene (—$CH_2CH_2$—), propylene (—$CH_2CH_2CH_2$—), and butylene (—$(CH_2)_4$—) groups. In the case of methylene, the two connected fragments are connected to the same carbon atom. A lower alkylene group may be substituted.

As used herein, "heteroalkylene" by itself or in combination with another term refers to an alkylene group consisting of the stated number of carbon atoms in which one or more of the carbon atoms, such as 1, 2, 3 or 4 carbon atom(s), are independently replaced with the same or different heteroatoms selected from oxygen, sulfur and nitrogen. Examples of heteroalkylene include, but not limited to —$CH_2$—O—, —$CH_2$—$CH_2$—O—, —$CH_2$—$CH_2$—$CH_2$—O—, —$CH_2$—NH—, —$CH_2$—$CH_2$—NH—, —$CH_2$—$CH_2$—$CH_2$—NH—, —$CH_2$—$CH_2$—NH—$CH_2$—, —O—$CH_2$—$CH_2$—O—$CH_2$—$CH_2$—O—, —O—$CH_2$—$CH_2$—O—$CH_2$—$CH_2$—, and the like.

As used herein, "alkylidene" refers to a divalent group, such as =CR'R", which is attached to one carbon of another group, forming a double bond. Alkylidene groups include, but are not limited to, methylidene (=$CH_2$) and ethylidene (=$CHCH_3$). As used herein, "arylalkylidene" refers to an alkylidene group in which either R' or R" is an aryl group. An alkylidene group may be substituted.

As used herein, "alkoxy" refers to the group —OR wherein R is an alkyl, e.g. methoxy, ethoxy, n-propoxy, cyclopropoxy, 1-methylethoxy (isopropoxy), n-butoxy, iso-butoxy, sec-butoxy, tert-butoxy, amoxy, tert-amoxy and the like. An alkoxy may be substituted.

As used herein, "alkylthio" refers to the formula —SR wherein R is an alkyl is defined as above, e.g. methylmercapto, ethylmercapto, n-propylmercapto, 1-methylethylmercapto (isopropylmercapto), n-butylmercapto, iso-butylmercapto, sec-butylmercapto, tert-butylmercapto, and the like. An alkylthio may be substituted.

As used herein, "aryloxy" and "arylthio" refers to RO— and RS—, in which R is an aryl as defined above, e.g., phenoxy, naphthalenyloxy, azulenyloxy, anthracenyloxy, naphthalenylthio, phenylthio and the like. Both an aryloxy and arylthio may be substituted.

As used herein, "alkenyloxy" refers to the formula —OR wherein R is an alkenyl as defined above, e.g., vinyloxy, propenyloxy, n-butenyloxy, iso-butenyloxy, sec-pentenyloxy, tert-pentenyloxy, and the like. The alkenyloxy may be substituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from $C_3$ to $C_{10}$, such as from $C_3$ to $C_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. When substituted, substituents on a cycloalkyl group may form an aromatic ring fused to the cycloalkyl group, including an aryl and a heteroaryl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). When composed of two or more rings, the rings may be connected together in a fused, bridged or spiro-connected fashion. Cycloalkenyl groups may range from $C_3$ to $C_{10}$, such as from $C_3$ to $C_8$ or from $C_5$ to $C_{10}$. For example, $C_{3-8}$ cycloalkenyl includes $C_{4-8}$ cycloalkenyl, $C_{5-8}$ cycloalkenyl or $C_{6-8}$ cycloalkenyl. A cycloalkenyl group may be unsubstituted or substituted. When substituted, the substituent(s) may be an alkyl or selected from the groups disclosed above with regard to alkyl group substitution unless otherwise indicated. When substituted, substituents on a cycloalkenyl group may form an aromatic ring fused to the cycloalkenyl group, including an aryl and a heteroaryl.

As used herein, "cycloalkynyl" refers to a cycloalkyl group that contains one or more triple bonds in the ring. When composed of two or more rings, the rings may be joined together in a fused, bridged or spiro-connected fashion. Cycloalkynyl groups may range from $C_8$ to $C_{12}$. A cycloalkynyl group may be unsubstituted or substituted. When substituted, the substituent(s) may be an alkyl or selected from the groups disclosed above with regard to alkyl group substitution unless otherwise indicated. When substituted, substituents on a cycloalkynyl group may form an aromatic ring fused to the cycloalkynyl group, including an aryl and a heteroaryl.

As used herein, "heteroalicyclic" or "heteroalicyclyl" refers to a 3- to 18 membered ring which consists of carbon atoms and from one to five heteroatoms selected from the group consisting of nitrogen, oxygen and sulfur. The heteroalicyclic or heteroalicyclyl groups may range from $C_2$ to $C_{10}$, in some embodiments it may range from $C_2$ to $C_9$, and in other embodiments it may range from $C_2$ to $C_8$. The "heteroalicyclic" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heteroalicyclic" or "heteroalicyclyl" may be oxidized; the nitrogen may be quaternized; and the rings may also contain one or more double bonds provided that they do not form a fully delocalized pi-electron system throughout all the rings, examples are 2H-benzo[b][1,4]oxazin-3(4H)-one, 3,4-dihydroquinolin-2(1H)-one, 1,2,3,4-tetrahydroquinoline, 3,4-dihydro-2H-benzo[b][1,4]oxazine, 2,3-dihydrobenzo[d]oxazole, 2,3-dihydro-1H-benzo[d]imidazole, indoline, and 1,3-dihydro-2H-benzo[d]imidazol-2-one, and benzo[d]oxazol-2 (3H)-one. Heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, C-amido, N-amido, S-sulfonamido, N-sulfonamido, isocyanato, thiocyanato, isothiocyanato, nitro, silyl, haloalkyl, haloalkoxy, trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, dioxolanyl, imidazolinyl, morpholinyl, oxetanyl, oxiranyl, piperidinyl N-Oxide, piperidinyl, piperazinyl, pyrrolidinyl, pyranyl, 4-piperidonyl, pyrazolidinyl, 2-oxopyrrolidinyl, tetrahydrofuranyl, tetrahydropyranyl, thiamorpholinyl, thiamorpholinyl sulfoxide, and thiamorpholinyl sulfone. When substituted, substituents on a heteroalicyclyl group may form an aromatic ring fused to the heteroalicyclyl group, including an aryl and a heteroaryl.

A "fused bicyclic ring" refers to a ring system where the two rings share two adjacent atoms. The two rings share one covalent bond. An example of a fused bicyclic ring is decalin.

A "spiro bicyclic ring" refers to a bicyclic ring wherein the two rings share one atom.

A "bridged ring system" refers to a ring system where two rings share three or more atoms. The two bridgehead atoms are separated by a bridge containing at least one atom, a specific example is norbornane, also known as bicyclo [2.2.1]heptane. The structure of bicyclo[2.2.1]heptane is shown below, also indicating the bridgehead atoms

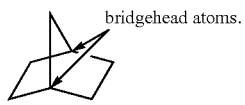

A "(cycloalkyl)alkyl" is a cycloalkyl group connected, as a substituent, via an alkylene group. The alkylene and cycloalkyl of a (cycloalkyl)alkyl may be substituted. Examples include but are not limited cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

A "(cycloalkenyl)alkyl" is a cycloalkenyl group connected, as a substituent, via an alkylene group. The alkylene and cycloalkenyl of a (cycloalkenyl)alkyl may be substituted. In some cases, the alkylene group is a lower alkylene group.

A "(cycloalkynyl)alkyl" is a cycloalkynyl group connected, as a substituent, via an alkylene group. The alkylene and cycloalkynyl of a (cycloalkynyl)alkyl may be substituted. In some cases, the alkylene group is a lower alkylene group.

As used herein, "halo" or "halogen" refers to F (fluoro), Cl (chloro), Br (bromo) or I (iodo).

As used herein, "haloalkyl" refers to an alkyl group in which one or more of the hydrogen atoms are replaced by halogen. Such groups include but are not limited to, chloromethyl, fluoromethyl, difluoromethyl, trifluoromethyl and 1-chloro-2-fluoromethyl, 2-fluoroisobutyl. A haloalkyl may be substituted.

As used herein, "haloalkoxy" refers to a RO-group in which R is a haloalkyl group. Such groups include but are not limited to, chloromethoxy, fluoromethoxy, difluoromethoxy, trifluoromethoxy and 1-chloro-2-fluoromethoxy, 2-fluoroisobutyoxy. A haloalkoxy may be substituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted.

A "C-carboxy" group refers to a "—C(=O)OR" group in which R can be the same as defined with respect to O-carboxy. A C-carboxy may be substituted.

A "trihalomethanesulfonyl" group refers to an "$X_3CSO_2$—" group" wherein X is a halogen.

A dashed bond, -----, represents an optional unsaturation between the atoms forming the bond. This bond may be unsaturated (e.g. C=C, C=N, C=O) or saturated (e.g. C—C, C—N, C—O). When a dashed bond is present in a ring system it may form part of an aromatic ring system.

A "nitro" group refers to a "—$NO_2$" group.
A "cyano" group refers to a "—CN" group.
A "cyanato" group refers to an "—OCN" group.
An "isocyanato" group refers to a "—NCO" group.
A "thiocyanato" group refers to a "—SCN" group.
A "carbonyl" group refers to a "—C(=O)—" group.
A "thiocarbonyl" group refers to a "—C(=S)—" group.
An "oxo" group refers to a "=O" group.
A "hydroxy" group or "hydroxyl" group refers to an "—OH" group.
An "isothiocyanato" group refers to an "—NCS" group.
A "sulfinyl" group refers to an "—S(=O)—R" group in which R can be the same as defined with respect to O-carboxy. A sulfinyl may be substituted.

A "sulfonyl" group refers to an "$SO_2R$" group in which R can be the same as defined with respect to O-carboxy. A sulfonyl may be substituted.

An "S-sulfonamido" group refers to a "—$SO_2NR_AR_B$" group in which $R_A$ and $R_B$ independently of each other can be the same as defined with respect to the R group as defined for O-carboxy, or combined to form a ring system selected from the group consisting of substituted or unsubstituted $C_{3-8}$ cycloalkyl, substituted or unsubstituted $C_{3-8}$ cycloalkenyl, substituted or unsubstituted heteroalicyclyl, substituted or unsubstituted aryl, and substituted or unsubstituted heteroaryl. A S-sulfonamido may be substituted.

An "N-sulfonamido" group refers to a "$RSO_2N(R_A)$—" group in which R and $R_A$ independently of each other can be the same as defined with respect to the R group as defined for O-carboxy. An N-sulfonamido may be substituted.

A "trihalomethanesulfonamido" group refers to an "$X_3CSO_2N(R)$—" group with X as halogen and R can be the same as defined with respect to O-carboxy. A trihalomethanesulfonamido may be substituted.

A "C-amido" group refers to a "—C(=O)$NR_AR_B$" group in which $R_A$ and $R_B$ independently of each other can be the same as defined with respect to the R group as defined for O-carboxy, or combined to form a ring system selected from the group consisting of substituted or unsubstituted $C_{3-8}$ cycloalkyl, substituted or unsubstituted $C_{3-8}$ cycloalkenyl, substituted or unsubstituted heteroalicyclyl, substituted or unsubstituted aryl, and substituted or unsubstituted heteroaryl. A C-amido may be substituted.

An "N-amido" group refers to a "RC(=O)$NR_A$—" group in which R and $R_A$ independently of each other can be the same as defined with respect to the R group as defined for O-carboxy. An N-amido may be substituted.

An "ester" refers to a "—C(=O)OR" group in which R can be the same as defined with respect to O-carboxy. An ester may be substituted.

A lower alkoxyalkyl refers to an alkoxy group connected via a lower alkylene group. A lower alkoxyalkyl may be substituted.

An "amine" or "amino" refers to "$RNH_2$" (a primary amine), "$R_2NH$" (a secondary amine), "$R_3N$" (a tertiary amine). An amino group may be substituted.

An aminoalkyl refers to an amino group connected via a lower alkylene group. An aminoalkyl may be substituted.

As used herein "0" (zero), for example in connection with a subscript means that it's absent. For example —$(CH_2)_s$—$C_{2-6}$ alkyl, wherein S can be "0" means that the —$(CH_2)$— is absent and the remaining group is —$C_{2-6}$ alkyl.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, 3$^{rd}$ Ed., John Wiley & Sons, New York, N.Y., 1999).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As employed herein, the following terms have their accepted meaning in the chemical literature.

| | |
|---|---|
| EtOAc | Ethylacetate |
| DIEA | N,N-Diisopropylethylamine |
| HCl | Hydrochloric acid |
| DMF | N,N-dimethylformamide |
| THF | Tetrahydrofuran |
| $CDCl_3$ | Chloroform-d |
| DMSO-D6 | Dimethylsulfoxide-d6 |
| $MgSO_4$ | Magnesium Sulfate |
| $POCl_3$ | Phosphorus(V) oxychloride |
| KOH | Potassium hydroxide |
| NaOH | Sodium hydroxide |
| $Na_2SO_4$ | Sodium Sulfate |
| $K_2CO_3$ | Potassium carbonate |
| $Na_2CO_3$ | Sodium carbonate |
| TFA | Trifluoroacetic acid |
| Boc | t-butoxycarbonyl |
| FMOC | Fluorenylmethyloxycarbonyl |
| FMOC—Cl | 9-Fluorenylmethoxycarbonyl chloride |
| TEOC | 2-(trimetylsilyl)ethoxycarbonyl |
| equiv. | equivalents |
| min | minutes |
| cat | catalytical |
| HCl | hydrochloric acid |
| HPLC | high performance liquid chromatography |

It is understood that, in any compound disclosed herein having one or more stereocenters, if an absolute stereochemistry is not expressly indicated, then each center may independently be of R-configuration or S-configuration or a mixture thereof. Thus, the compounds provided herein may be enatiomerically pure or be stereoisomeric mixtures. Further, compounds provided herein may be scalemic mixtures. In addition, it is understood that in any compound having one or more double bond(s) generating geometrical isomers that can be defined as E or Z each double bond may independently be E or Z or a mixture thereof. Likewise, all tautomeric forms are also intended to be included.

As used herein, "tautomer" and "tautomeric" refer to alternate forms of a compound disclosed herein that differ in the position of a proton. Non-limiting examples include enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

It is understood that isotopes may be present in the compounds described herein. Each chemical element as represented in a compound structure may include any isotope of said element. For example, in a compound described herein a hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise. For example the term "methyl" includes —$CH_3$, —$CD_3$, —$CH_2D$ etc.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, acetates, adipates, aspartates, ascorbates, benzoates, butyrates, caprate, caproate, caprylate, camsylates, citrates, decanoates, formates, fumarates, gluconates, glutarate, glycolates, hexanoates, laurates, lactates, maleates, nitrates, oleates, oxalates, octanoates, propanoates, palmitates, phosphates, sebacates, succinates, stearates, sulfates, sulfonates, such as methanesulfonates, ethanesulfonates, p-toluenesulfonates, salicylates, tartrates, and tosylates.

Pharmaceutically acceptable solvates and hydrates are complexes of a compound with one or more solvent of water molecules, or 1 to about 100, or 1 to about 10, or one to about 2, 3 or 4, solvent or water molecules.

As used herein, a "prodrug" refers to a compound that may not be pharmaceutically active but that is converted into an active drug upon in vivo administration. The prodrug may be designed to alter the metabolic stability or the transport characteristics of a drug, to mask side effects or toxicity, to improve the flavor of a drug or to alter other characteristics or properties of a drug. Prodrugs are often useful because they may be easier to administer than the parent drug. They may, for example, be bioavailable by oral administration whereas the parent drug is not. The prodrug may also have better solubility than the active parent drug in pharmaceutical compositions. An example, without limitation, of a prodrug would be a compound disclosed herein, which is administered as an ester (the "prodrug") to facilitate absorption through a cell membrane where water solubility is detrimental to mobility but which then is metabolically hydrolyzed to a carboxylic acid (the active entity) once inside the cell where water-solubility is beneficial. A further example of a prodrug might be a short peptide (polyaminoacid) bonded to an acid group where the peptide is metabolized in vivo to release the active parent compound. By virtue of knowledge of pharmacodynamic processes and drug metabolism in vivo, those skilled in the art, once a pharmaceutically active compound is known, can design prodrugs of the compound (see, e.g. Nogrady (1985) *Medicinal Chemistry A Biochemical Approach*, Oxford University Press, New York, pages 388-392). A specific example of prodrugs relates to formation of a basic nitrogen comprising the piperidyl group of Formula (I), wherein the basic nitrogen may be formed by the metabolic cleavage of a group attached to the nitrogen of the piperidyl group, forming a basic nitrogen, e.g. as shown in Formula A. Particular examples are acyl and tosyl groups attached to the nitrogen.

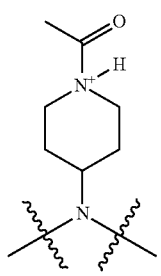

(A)

"Anti-drug" refers to a compound or composition acting against or opposing illicit drugs or their use. Compounds of the present application may act as anti-drugs.

As used herein, to "modulate" the activity of a receptor means either to activate it, i.e., to increase its cellular function over the base level measured in the particular environment in which it is found, or deactivate it, i.e., decrease its cellular function to less than the measured base level in the environment in which it is found and/or render it unable to perform its cellular function at all, even in the presence of a natural binding partner. A natural binding partner is an endogenous molecule that is an agonist for the receptor.

An "agonist" is defined as a compound that increases the basal activity of a receptor (i.e. signal transduction mediated by the receptor).

As used herein, "partial agonist" refers to a compound that has an affinity for a receptor but, unlike an agonist, when bound to the receptor it elicits only a fractional degree of the pharmacological response normally associated with the receptor even if a large number of receptors are occupied by the compound.

An "inverse agonist" is defined as a compound, which reduces, or suppresses the basal activity of a receptor, such that the compound is not technically an antagonist but, rather, is an agonist with negative intrinsic activity.

As used herein, "antagonist" refers to a compound that binds to a receptor to form a complex that does not give rise to any response, as if the receptor was unoccupied. An antagonist attenuates the action of an agonist on a receptor. An antagonist may bind reversibly or irreversibly, effectively eliminating the activity of the receptor permanently or at least until the antagonist is metabolized or dissociates or is otherwise removed by a physical or biological process.

As used herein, a "subject" refers to an animal that is the object of treatment, observation or experiment. "Animal" includes cold- and warm-blooded vertebrates and invertebrates such as birds, fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

A "receptor" is intended to include any molecule present inside or on the surface of a cell that may affect cellular physiology when it is inhibited or stimulated by a ligand. Typically, a receptor comprises an extracellular domain with ligand-binding properties, a transmembrane domain that anchors the receptor in the cell membrane, and a cytoplasmic domain that generates a cellular signal in response to ligand binding ("signal transduction"). A receptor also includes any intracellular molecule that in response to ligation generates a signal. A receptor also includes any molecule having the characteristic structure of a receptor, but with no identifiable ligand. In addition, a receptor includes a truncated, modified, mutated receptor, or any molecule comprising partial or all of the sequences of a receptor.

"Ligand" is intended to include any substance that interacts with a receptor.

"Selective" or "selectivity" is defined as a compound's ability to generate a desired response from a particular receptor type, subtype, class or subclass while generating less or little response from other receptor types. "Selective"

or "selectivity" of one or more particular subtypes of a compound means a compound's ability to increase the activity of the subtypes while causing less, little or no increase in the activity of other subtypes. Selectivity of a compound between receptor targets may for example be determined by the ratio of potencies or affinities for those targets. For example, a compound is said to be 10-fold selectivity for Target 1 over Target 2 if said compound has a pKi of 10 nM for Target 1 and 100 nM for Target 2. Said compound is therefore 10-fold more potent at Target 1, i.e. it is 10-fold selective for Target 1.

As used herein, "IC50" refers to an amount, concentration, or dosage of a particular test compound that achieves a 50% inhibition of a maximal response. The IC50 can be determined using an assay. The assay may be an R-SAT® assay as described herein but is not limited to an RSAT assay.

As used herein, "EC50" refers to an amount, concentration or dosage of a particular test compound that elicits a dose-dependent response at 50% of maximal expression of a particular response that is induced, provoked or potentiated by the particular test compound, in an assay that measures such response such as but not limited to R-SAT® assay described herein.

As used herein, "pKi" refers to the negative logarithm of the Ki, the equilibrium dissociation constant of an antagonist-receptor complex measured in a functional antagonist or radioligand binding assay, e.g. R-SAT® assay as described herein.

As used herein, "coadministration" of pharmacologically active compounds refers to the delivery of two or more separate chemical entities, whether in vitro or in vivo. Coadministration means the simultaneous delivery of separate agents; the simultaneous delivery of a mixture of agents; as well as the delivery of one agent followed by delivery of a second agent or additional agents. Agents that are coadministered are typically intended to work in conjunction with each other.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

Compounds

Provided herein are compounds according to Formulas (I)-(II), or pharmaceutically acceptable salt, polymorph or stereoisomer thereof.

Some embodiments relate to a compound of Formula (I),

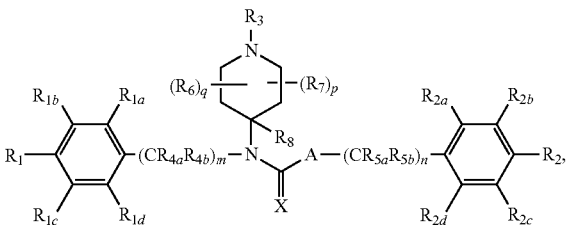

(I)

or a pharmaceutically acceptable salt, hydrate, solvate, polymorph, prodrug, stereoisomer, and deuterated analogue thereof, wherein:

m, and n are independently an integer selected from the group consisting of 0, 1, 2, and 3;

p, and q are independently an integer selected from the group consisting of 0, 1, 2, 3, and 4;

$R_1$, $R_{1a}$, $R_{1b}$, $R_{1c}$ and $R_{1d}$ are independently selected from the group consisting of hydrogen, deuterium, hydroxyl, —OD, halogen, cyano, amino, —S(=O)$_2R_{10}$, —OC(=O)$R_{11}$, —C(=O)OR$_{11}$, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{1-6}$ aminoalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein at least one of $R_1$, $R_{1a}$, $R_{1b}$, $R_{1c}$ and $R_{1d}$ is not hydrogen, wherein $R_{10}$ and $R_{11}$, independently are selected from the group consisting of hydrogen, amino, unsubstituted or substituted $C_{1-6}$ alkyl;

$R_2$, $R_{2a}$, $R_{2b}$, $R_{2c}$ and $R_{2d}$ are independently selected from the group consisting of hydrogen, deuterium, amino, hydroxyl, —OD, halogen, cyano, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein at least one of $R_2$, $R_{2a}$, $R_{2b}$, $R_{2c}$ and $R_{2d}$ is not hydrogen, or $R_2$ and $R_{2b}$ or $R_{2c}$, taken together with the atoms to which they are attached form a ring system;

$R_3$ is selected from the group consisting of hydrogen, deuterium, hydroxyl, —OD, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl; or $R_3$, the nitrogen to which $R_3$ is attached and a carbon atom adjacent to the nitrogen taken together with $R_6$ or $R_7$ form a heteroalicyclic ring system;

$R_{4a}$, $R_{4b}$, $R_{5a}$, and $R_{5b}$, are independently selected from the group consisting of hydrogen, deuterium, and unsubstituted or substituted $C_{1-6}$ alkyl;

$R_6$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy, substituted or unsubstituted aryl;

$R_7$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy;

$R_8$ is absent, or selected from the group consisting of hydrogen, deuterium, cyano, hydroxyl, —OD, substituted or unsubstituted $C_{1-4}$ alkyl, substituted or unsubstituted $C_{2-4}$ alkenyl, substituted or unsubstituted $C_{3-6}$ cycloalkyl, and substituted or unsubstituted $C_{1-4}$ alkoxy;

A is a bond, —S— or —O—; and

X is O or S.

In some embodiments the compound is a compound of Formula (I) provided it is not N-(2,4-difluorobenzyl)-2-(4-methoxyphenyl)-N-(piperidin-4-yl)acetamide.

In some embodiments $R_1$, $R_{1a}$, $R_{1b}$, $R_{1c}$ and $R_{1d}$ independently are selected from the group consisting of hydrogen, deuterium, hydroxyl, halogen, amino, —SO$_2$NH$_2$, —SO$_2$N(C$_{1-4}$ alkyl)$_2$, —SO$_2$—C$_{1-4}$ alkyl, —OC(═O)—C$_{1-4}$ alkyl, —N(C$_{1-4}$ alkyl)$_2$, C$_{1-6}$ alkyl, C$_{1-6}$ haloalkyl, C$_{1-6}$ alkoxy, C$_{3-4}$ cycloalkyl, C$_{3-4}$ cycloalkyl-C$_{1-3}$ alkyl and deuterated analogues thereof, e.g. $R_{1a}$, $R_{1b}$, $R_{1c}$ and $R_{1d}$ are independently selected from the group consisting of hydrogen, deuterium, hydroxyl, halogen, amino, SO$_2$NH$_2$, —SO$_2$CH$_3$, —OC(═O)CH$_3$, methyl, —CD$_3$, methoxy, —OCD$_3$, —OCF$_3$ and —CF$_3$; and $R_1$ is selected from halogen, amino, SO$_2$NH$_2$, —SO$_2$CH$_3$, —OC(═O)CH$_3$, methyl, —CD$_3$, ethyl, —CD$_2$CD$_3$, optionally deuterated n-propyl, optionally deuterated iso-propyl, optionally deuterated n-butyl, optionally deuterated iso-butyl, optionally deuterated n-pentyl, optionally deuterated 2-methyl-butyl, optionally deuterated n-hexyl, optionally deuterated 2-methyl-pentyl, methoxy, —OCD$_3$, optionally deuterated ethoxy, optionally deuterated n-propoxy, optionally deuterated isopropoxy, optionally deuterated n-butoxy, optionally deuterated iso-butoxy, optionally deuterated pentyl-oxy, optionally deuterated 4-methyl-butoxy, optionally deuterated hexyl-oxy, optionally deuterated 4-methylpentoxy, —OCF$_3$, —OCF$_2$CF$_3$, —OCHF$_2$, —OCDF$_2$, —CF$_3$, —CF$_2$CF$_3$, —CHF$_2$, CDF$_2$—CH$_2$CF$_3$, —CD$_2$CF$_3$, —CH$_2$F, 1,1,2,2-tetrafluorobutyl and 1,1,1,2,2-pentafluorobutyl.

In some embodiments $R_{1a}$, $R_{1b}$, $R_{1c}$ and $R_{1d}$ are independently selected from the group consisting of hydrogen, deuterium, hydroxyl, halogen, amino, SO$_2$NH$_2$, —SO$_2$CH$_3$, —OC(═O)CH$_3$, methyl, —CD$_3$, methoxy, —OCD$_3$, —OCF$_3$ and —CF$_3$; and $R_1$ is selected from the group consisting of halogen, hydroxyl, —CD$_3$, —CD$_2$CD$_3$, C$_{1-6}$ alkyl, —OCD$_3$, C$_{1-6}$ alkoxy, —OCF$_3$, —OCF$_2$CF$_3$, —OCHF$_2$, —OCDF$_2$, —CF$_3$, —CF$_2$CF$_3$, —CHF$_2$, —CDF$_2$—CH$_2$CF$_3$, —CD$_2$CF$_3$, and —CH$_2$F.

In some embodiments $R_{1a}$, $R_{1b}$, and $R_{1c}$ are hydrogen, and $R_{1d}$ is selected from the group consisting of hydrogen, hydroxyl and fluoro; and $R_1$ is selected from fluoro, chloro, methyl, methoxy, —OCF$_3$ and —CF$_3$, such as fluoro, chloro and —CF$_3$.

In some embodiments $R_1$ and $R_{1d}$ are fluoro, and $R_{1a}$, $R_{1b}$ and $R_{1c}$ are hydrogen.

In some embodiments $R_{1a}$, $R_{1b}$, and $R_{1c}$ are hydrogen, and $R_{1d}$ is selected from the group consisting of hydrogen, hydroxyl, fluoro, chloro, methyl, methoxy, CF$_3$ and OCF$_3$.

In some embodiments $R_1$ is selected from the group consisting of fluoro, chloro, methyl, methoxy, —OCF$_3$ and —CF$_3$. In some embodiments $R_1$ is selected from the group consisting of fluoro, chloro, methyl, and methoxy.

In some embodiments $R_{1d}$ is selected from the group consisting of hydrogen, hydroxyl, fluoro, chloro, methyl, methoxy, CF$_3$ and OCF$_3$; and $R_1$ is selected from the group consisting of fluoro, chloro, methyl, methoxy, —OCF$_3$ and —CF$_3$; and $R_{1a}$, $R_{1b}$, and $R_{1c}$ are hydrogen. In some embodiments $R_1$ and $R_{1d}$ are independently selected from the group consisting of fluoro, chloro, methyl, methoxy, CF$_3$, and OCF$_3$; and $R_{1a}$, $R_{1b}$ and $R_{1c}$ are hydrogen.

In some embodiments $R_{1a}$, $R_{1b}$, and $R_{1c}$ are hydrogen, and $R_{1d}$ is fluoro and $R_1$ is selected from fluoro, chloro, methyl, methoxy, —OCF$_3$ and —CF$_3$.

In some embodiments $R_{1a}$, $R_{1b}$, and $R_{1c}$ are hydrogen, and $R_1$ is fluoro and $R_{1d}$ is selected from fluoro, chloro, methyl, methoxy, —OCF$_3$ and —CF$_3$.

In some embodiments $R_1$ and $R_{1d}$ are fluoro or chloro, and $R_{1a}$, $R_{1b}$ and $R_{1c}$ are hydrogen.

In some embodiments $R_{1a}$ and $R_{1d}$ are fluoro, and $R_{1b}$, $R_{1c}$ and $R_1$ are independently selected from the group consisting of hydrogen, fluoro, chloro, methyl, methoxy, —OCF$_3$ and —CF$_3$. In some embodiments, $R_{1a}$ and $R_{1d}$ are fluoro, and at least one of $R_{1b}$, $R_{1c}$ and $R_1$ is selected from the group consisting of fluoro, chloro, methyl, methoxy, —OCF$_3$ and —CF$_3$. In some embodiments $R_{1a}$ and $R_{1d}$ are fluoro, and $R_{1b}$ and $R_{1c}$ are hydrogen, and $R_1$ is independently selected from the group consisting of hydrogen, fluoro, chloro, methyl, methoxy, —OCF$_3$ and —CF$_3$. In some embodiments $R_{1a}$ and $R_{1d}$ are fluoro, and $R_1$ or $R_{1c}$ are hydrogen, and $R_{1b}$ is independently selected from the group consisting of hydrogen, fluoro, chloro, methyl, methoxy, —OCF$_3$ and —CF$_3$.

In some embodiments $R_{1a}$, $R_{1c}$, and $R_{1d}$ are hydrogen, and $R_{1b}$ is selected from the group consisting of hydrogen, hydroxyl and fluoro; and $R_1$ is selected from fluoro, chloro, methyl, methoxy, —OCF$_3$ and —CF$_3$, such as fluoro, chloro and —CF$_3$.

In some embodiments $R_1$ and $R_{1b}$ are independently selected from the group consisting of fluoro, chloro, methyl, methoxy, —OCF$_3$ and —CF$_3$. In some embodiments, $R_1$ and $R_{1b}$ are independently selected from the group consisting of fluoro, chloro, methyl, methoxy, —OCF$_3$ and —CF$_3$, and $R_{1a}$, $R_{1c}$ and $R_{1d}$ are hydrogen.

In some embodiments $R_1$ and $R_{1d}$ are fluoro, and $R_{1a}$, $R_{1b}$ and $R_{1c}$ are hydrogen.

In some embodiments one of $R_{1a}$, $R_{1b}$, $R_{1c}$ and $R_{1d}$ is selected from the group consisting of fluoro, chloro, methyl and methoxy, the others are hydrogen; $R_1$ is selected from the group consisting of fluoro, chloro, methyl and methoxy.

In some embodiments two of $R_{1a}$, $R_{1b}$, $R_{1c}$ and $R_{1d}$ are independently selected from the group consisting of fluoro, chloro, methyl, methoxy, —OCF$_3$ and —CF$_3$, the others are hydrogen; $R_1$ is selected from the group consisting of fluoro, chloro, methyl, methoxy, —OCF$_3$ and —CF$_3$. In some embodiments $R_{1a}$ and $R_{1b}$ are independently selected from the group consisting of fluoro, chloro, methyl, methoxy, —OCF$_3$ and —CF$_3$, $R_{1c}$ and $R_{1d}$ are hydrogen; $R_1$ is selected from the group consisting of fluoro, chloro, methyl, methoxy, —OCF$_3$ and —CF$_3$. In some embodiments $R_{1a}$ and $R_{1c}$ are independently selected from the group consisting of fluoro, chloro, methyl, methoxy, —OCF$_3$ and —CF$_3$, $R_{1b}$ and $R_{1d}$ are hydrogen; $R_1$ is selected from the group consisting of fluoro, chloro, methyl, methoxy, —OCF$_3$ and —CF$_3$. In some embodiments $R_{1a}$ and $R_{1d}$ are independently selected from the group consisting of fluoro, chloro, methyl, methoxy, —OCF$_3$ and —CF$_3$, $R_{1b}$ and $R_{1c}$ are hydrogen; $R_1$ is selected from the group consisting of fluoro, chloro, methyl, methoxy, —OCF$_3$ and —CF$_3$.

In some embodiments $R_2$, $R_{2a}$, $R_{2b}$, $R_{2c}$ and $R_{2d}$ independently are selected from the group consisting of hydrogen, hydroxyl, halogen, cyano, C$_{1-6}$ alkyl, C$_{1-6}$ haloalkyl, C$_{1-6}$ alkoxy, C$_{1-6}$ haloalkoxy, C$_{3-4}$ cycloalkyl, C$_{3-4}$ cycloalkyl-C$_{1-3}$ alkyl and deuterated analogues thereof, or $R_{2a}$, $R_{2c}$ and $R_{2a}$ are hydrogen and $R_2$ and $R_{2b}$, taken together with the phenyl ring they attach to and the atoms to which they are attached form a bicyclic fused ring system that has the following general formulae

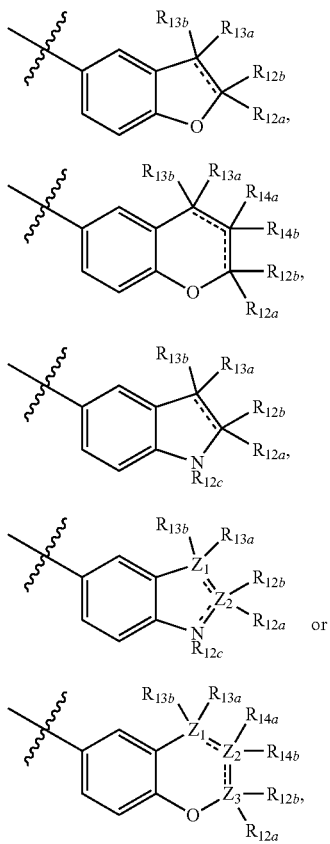

wherein $R_{12a}$, $R_{12b}$, $R_{12c}$, $R_{13a}$, $R_{13b}$, $R_{14a}$, and $R_{14b}$ independently are absent or selected from the group consisting of hydrogen, halogen, hydroxyl, cyano, $C_{1-4}$ alkyl, and $C_{1-4}$ alkoxy, and wherein $Z_1$, $Z_2$ and $Z_3$ independently are selected from the group consisting of C, N, O and S, e.g. $R_{2a}$, $R_{2b}$, $R_{2c}$ and $R_{2d}$ independently are selected from the group consisting of hydrogen, deuterium, hydroxyl, halogen, methyl, —$CD_3$, methoxy, —$OCD_3$, —$OCF_3$ and —$CF_3$; and $R_2$ is selected from halogen, methyl, —$CD_3$, ethyl, —$CD_2CD_3$, optionally deuterated n-propyl, optionally deuterated iso-propyl, optionally deuterated n-butyl, optionally deuterated iso-butyl, optionally deuterated n-pentyl, optionally deuterated 2-methyl-butyl, optionally deuterated n-hexyl, optionally deuterated 2-methyl-pentyl, optionally deuterated methoxy, optionally deuterated ethoxy, optionally deuterated n-propoxy, optionally deuterated isopropoxy, optionally deuterated allyloxy, optionally deuterated prop-2-yn-1-yloxy, optionally deuterated n-butoxy, optionally deuterated iso-butoxy, optionally deuterated tert-butoxy, optionally deuterated pentyl-oxy, optionally deuterated 4-methyl-butoxy, optionally deuterated hexyl-oxy, optionally deuterated 4-methylpentoxy, optionally deuterated cyclopropyloxy, optionally deuterated cyclopropylmethoxy, optionally deuterated cyclopropylethoxy, optionally deuterated cyclobutyloxy, optionally deuterated cyclobutyloxy, optionally deuterated cyclobutylmethoxy, optionally deuterated cyclobutylethoxy, optionally deuterated $C_{1-6}$ haloalkoxy, —$OCF_3$, —$OCF_2CF_3$, —$OCHF_2$, —$OCDF_2$, —$CF_3$, —$CF_2CF_3$, —$CHF_2$, $CDF_2$—$CH_2CF_3$, —$CD_2CF_3$, —$CH_2F$, 1,1,2,2-tetrafluorobutyl and 1,1,1,2,2-pentafluorobutyl. $R_2$ is not a nitro group.

In some embodiments the formed ring system is of Formula (III), and both $R_{12a}$ and $R_{12b}$ are hydrogen or methyl, and both $R_{13a}$ and $R_{13b}$ are hydrogen or methyl.

In some embodiments $R_{2a}$, $R_{2c}$, $R_{2d}$ and $R_{2b}$, provided $R_{2b}$ is not forming a ring system with $R_2$, independently are selected from the group consisting of hydrogen, deuterium, hydroxyl, halogen, methyl, —$CD_3$, methoxy, —$OCD_3$, —$OCF_3$ and —$CF_3$. In some embodiments $R_{2a}$, $R_{2c}$ and $R_{2b}$, provided $R_{2b}$ is not forming a ring system with $R_2$, are hydrogen, and $R_{2d}$ is hydrogen, fluoro or hydroxyl. In some embodiments $R_{2a}$ or $R_{2b}$ is fluoro and the other is hydrogen, $R_{2c}$ and $R_{2d}$ are hydrogen.

In some embodiments, provided $R_2$ is not forming a ring system with $R_{2b}$, $R_2$ is selected from the group consisting of halogen, cyano, methyl, —$CD_3$, ethyl, —$CD_2CD_3$, optionally deuterated n-propyl, optionally deuterated iso-propyl, optionally deuterated n-butyl, optionally deuterated iso-butyl, optionally deuterated n-pentyl, optionally deuterated 2-methyl-butyl, optionally deuterated n-hexyl, optionally deuterated 2-methyl-pentyl, optionally deuterated methoxy, optionally deuterated ethoxy, optionally deuterated n-propoxy, optionally deuterated isopropoxy, optionally deuterated allyloxy, optionally deuterated prop-2-yn-1-yloxy, optionally deuterated n-butoxy, optionally deuterated iso-butoxy, optionally deuterated tert-butoxy, optionally deuterated pentyl-oxy, optionally deuterated 4-methyl-butoxy, optionally deuterated hexyl-oxy, optionally deuterated 4-methylpentoxy, optionally deuterated cyclopropyloxy, optionally deuterated cyclopropylmethoxy, optionally deuterated cyclopropylethoxy, optionally deuterated cyclobutyloxy, optionally deuterated cyclobutyloxy, optionally deuterated cyclobutylmethoxy, optionally deuterated cyclobutylethoxy, optionally deuterated $C_{1-6}$ haloalkoxy, —$OCF_3$, —$OCF_2CF_3$, —$OCHF_2$, —$OCDF_2$, —$CF_3$, —$CF_2CF_3$, —$CHF_2$, $CDF_2$—$CH_2CF_3$, —$CD_2CF_3$, —$CH_2F$, —$CF_2CH_3$, 2-fluoroethoxy, 3-fluoropropoxy, 4-fluorobutoxy, (1,3-difluoropropan-2-yl)oxy, 2-hydroxy-2-methylpropoxy, 1,1,2,2-tetrafluorobutyl and 1,1,1,2,2-pentafluorobutyl.

In some embodiments, provided $R_2$ is not forming a ring system with $R_{2b}$, $R_2$ is selected from the group consisting of halogen, hydroxyl, —$CD_3$, —$CD_2CD_3$, $C_{1-6}$ alkyl, —$OCD_3$, $C_{1-6}$ alkoxy, —$OCF_3$, —$OCF_2CF_3$, —$OCHF_2$, —$OCDF_2$, —$CF_3$, —$CF_2CF_3$, —$CHF_2$, —$CDF_2$—$CH_2CF_3$, —$CD_2CF_3$, and —$CH_2F$.

In some embodiments, provided $R_2$ is not forming a ring system with $R_{2b}$, $R_2$ is selected from the group consisting of methoxy, ethoxy, n-propoxy, isopropoxy, allyloxy, prop-2-yn-1-yloxy, n-butoxy, iso-butoxy, tert-butoxy, pentyl-oxy, 4-methyl-butoxy, hexyl-oxy, 4-methylpentoxy cyclopropyloxy, cyclopropylmethoxy, cyclopropylethoxy, cyclobutyloxy, cyclobutylmethoxy, cyclobutylethoxy, —$CF_2CH_3$, 2-fluoroethoxy, 3-fluoropropoxy, 4-fluorobutoxy, 2-hydroxyl-2-methyl-propoxy, 1,1-difluoroethyl, and (1,3-difluoropropan-2-yl)oxy.

In some embodiments $R_{2a}$, $R_{2b}$, and $R_{2c}$ are hydrogen, $R_{2d}$ is hydrogen, fluoro or hydroxyl, and $R_2$ is selected from methoxy, ethoxy, n-propoxy, isopropoxy, allyloxy, n-butoxy, iso-butoxy, tert-butoxy, pentyl-oxy, 4-methyl-butoxy, hexyl-oxy, 4-methylpentoxy, cyclopropyloxy, cyclopropylmethoxy, cyclopropylethoxy, cyclobutyloxy, cyclobutylmethoxy, cyclobutylethoxy, 2-fluoroethoxy, 3-fluoropropoxy, 4-fluoroethoxy, and (1,3-difluoropropan-2-yl)oxy.

In some embodiments $R_{2a}$, $R_{2b}$, and $R_{2c}$ are hydrogen, $R_{2a}$ is hydrogen, fluoro or hydroxyl, and $R_2$ is selected from the group consisting of methoxy, ethoxy, n-propoxy, isopropoxy, allyloxy, n-butoxy, iso-butoxy, tert-butoxy, pentyloxy, 4-methyl-butoxy, hexyl-oxy, 4-methylpentoxy, cyclopropyloxy, cyclopropylmethoxy, cyclopropylethoxy, cyclobutyloxy, cyclobutylmethoxy, cyclobutylethoxy, 2-fluoroethoxy, 3-fluoropropoxy, 4-fluorobutoxy, 2-hydroxyl-2-methyl-propoxy, 1,1-difluoroethyl, and (1,3-difluoropropan-2-yl)oxy.

In some embodiments $R_1$ and $R_{1d}$ are independently selected from the group consisting of fluoro, chloro, methyl, methoxy, $CF_3$, and $OCF_3$, and $R_{1a}$, $R_{1b}$ and $R_{1c}$ are hydrogen; $R_2$ is selected from the group consisting of methoxy, ethoxy, n-propoxy, isopropoxy, allyloxy, prop-2-yn-1-yloxy, n-butoxy, iso-butoxy, tert-butoxy, pentyl-oxy, 4-methyl-butoxy, hexyl-oxy, 4-methylpentoxy, cyclopropyloxy, cyclopropylmethoxy, cyclopropylethoxy, cyclobutyloxy, cyclobutylmethoxy, cyclobutylethoxy, 2-fluoroethoxy, 3-fluoropropoxy, 4-fluorobutoxy, 2-hydroxyl-2-methyl-propoxy, 1,1-difluoroethyl, and (1,3-difluoropropan-2-yl)oxy; and $R_{2a}$, $R_{2b}$, $R_{2d}$ and $R_{2d}$ are hydrogen; or $R_2$ and $R_{2b}$, taken together with the phenyl ring they attach to and the atoms to which they are attached form a bicyclic fused ring system that, has the following general formula

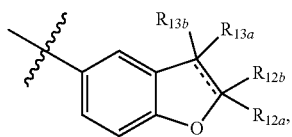

(III)

wherein $R_{12a}$ and $R_{12b}$ are hydrogen or methyl, and both $R_{13a}$ and $R_{13b}$ are hydrogen or methyl, and $R_{2a}$, $R_{2c}$ and $R_{2d}$ are hydrogen.

In some embodiments, $R_1$ and $R_{1d}$ are independently selected from the group consisting of fluoro, chloro, methyl, methoxy, $CF_3$, and $OCF_3$, and $R_{1a}$, $R_{1b}$ and $R_{1c}$ are hydrogen; and $R_2$ is selected from the group consisting of ethoxy, isopropoxy, allyloxy, tert-butoxy, isobutoxy, n-butoxy, cyclopropyloxy, 2-fluoroethoxy, 3-fluoropropoxy, 2-hydroxyl-2-methyl-propoxy, 1,1-difluoroethyl, and (1,3-difluoropropan-2-yl)oxy, and $R_{2a}$, $R_{2b}$, $R_{2d}$ and $R_{2d}$ are hydrogen; or $R_2$ and $R_{2b}$, taken together with the atoms to which they are attached form a heteroalicyclic ring system wherein the formed ring system, taken together with the phenyl group to which it is fused, has the following formulae

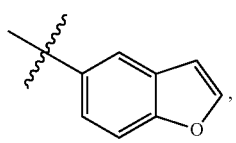

(IIIa)

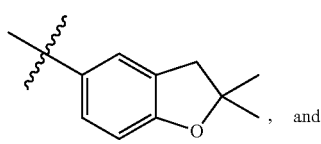

, and (IIIb)

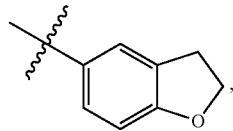

(IIIc)

and $R_{2a}$, $R_{2c}$ and $R_{2a}$ are hydrogen.

In some embodiments $R_1$ and $R_{1d}$ are fluoro, and $R_{1a}$, $R_{1b}$ and $R_{1c}$ are hydrogen; and $R_2$ is selected from the group consisting of ethoxy, isopropoxy, allyloxy, tert-butoxy, cyclopropyloxy, and 2-fluoroethoxy, and $R_{2a}$, $R_{2b}$, $R_{2d}$ and $R_{2d}$ are hydrogen; or $R_2$ and $R_{2b}$, taken together with the phenyl ring they attach to and the atoms to which they are attached form a bicyclic fused ring system that has the following general formulae

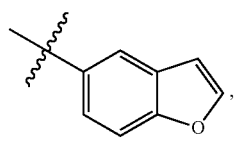

(IIIa)

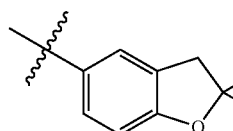

, and (IIIb)

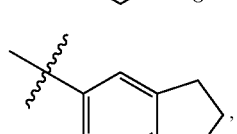

(IIIc)

and $R_{2a}$, $R_{2c}$ and $R_{2d}$ are hydrogen.

In some embodiments $R_3$ is selected from hydrogen, deuterium, hydroxyl, —OD, substituted or unsubstituted $C_{1-6}$ alkyl, substituted or unsubstituted $C_{1-6}$ alkoxy, substituted or unsubstituted —$(CH_2)_s$—$C_{3-6}$ cycloalkyl, substituted or unsubstituted —$(CH_2)_s$—$C_{2-5}$ heteroalicyclyl, substituted or unsubstituted —$(CH_2)_s$—$C_{2-5}$ heteroaryl, and substituted or unsubstituted —$(CH_2)_s$—$C_{5-6}$ aryl, wherein each s is selected from 0, 1, 2 and 3. $R_3$ could for example be hydrogen, methyl, —$CD_3$, ethyl, —$CD_2CD_3$, n-propyl, —$CD_2CD_2CD_3$, iso-propyl, —$CDCD_3CD_3$, and —$(CR_{9a}R_{9b})_tC(=O)OR_{9c}$ and —$(CH_2)_tC(=O)NR_{9a}R_{9b}$, wherein $R_{9a}$, $R_{9b}$, and $R_{9c}$ independently are selected from hydrogen and $C_{1-4}$-alkyl, wherein each t is selected from 0, 1, 2, and 3.

In some embodiments $R_3$ is selected from the group consisting of hydrogen, methyl, —$CD_3$, ethyl, —$CD_2CD_3$, n-propyl, —$CD_2CD_2CD_3$, iso-propyl, cyclopropyl, 3-oxetanyl, —$CDCD_3CD_3$, —$(CR_{9a}R_{9b})_tC(=O)OR_{9c}$, —$(CR_{9a}R_{9b})_t(CR_{9c}R_{9d})_wC(=O)OR_{9c}$, —$(CH_2)_t(CR_{9c}R_{9d})_wC(=O)NR_{9a}R_{9b}$ and —$(CH_2)_tC(=O)NR_{9a}R_{9b}$, wherein $R_{9a}$, $R_{9b}$, $R_{9c}$, $R_{9d}$ and $R_{9e}$ independently are hydrogen or $C_{1-4}$-alkyl, wherein each of t and w is selected from 0, 1, 2, and 3. In some embodiments $R_3$ is selected from the group consisting of hydrogen, methyl, ethyl, cyclopropyl, 3-oxetanyl, $CH_2C(CH_3)_2COOH$, and $CH_2C(CH_3)_2COOMe$.

In some embodiments $R_3$ is hydrogen or methyl.

In some embodiments $R_3$ is taken together with one $R_6$ or $R_7$, which is attached to a carbon atom adjacent the nitrogen atom, to form a heteroalicyclic ring system according to the following formulas:

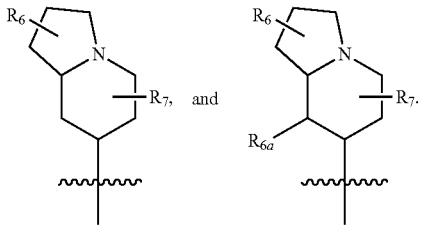

Optionally the formed heteroalicyclic ring systems may comprise additional $R_6$ and/or $R_7$ substituents, as shown above.

In some embodiments $R_{4a}$, $R_{4b}$, $R_{5a}$ and $R_{5b}$ are independently selected from the group consisting of hydrogen, methyl and —$CF_3$, for example $R_{4a}$, $R_{4b}$ and $R_{5a}$ are hydrogen and $R_{5b}$ is methyl or hydrogen; or $R_{4a}$, $R_{5a}$ and $R_{5b}$ are hydrogen and $R_{4b}$ is methyl or hydrogen.

In some embodiments $R_{4a}$, $R_{4b}$, $R_{5a}$ and $R_{5b}$ are independently selected from the group consisting of hydrogen, methyl and —$CF_3$, for example $R_{4a}$, $R_{4b}$ and $R_{5a}$ are hydrogen and $R_{5b}$ is methyl, —$CF_3$ or hydrogen; or $R_{4a}$, $R_{5a}$ and $R_{5b}$ are hydrogen and $R_{4b}$ is methyl, —$CF_3$ or hydrogen.

In some embodiments $R_{4a}$, $R_{4b}$, $R_{5a}$ and $R_{5b}$ are hydrogen.

In some embodiments $R_6$ is absent (e.g. when an unsaturation if present or when q is 0) or selected from the group consisting of hydrogen, deuterium, halogen, hydroxyl, —OD, substituted or unsubstituted $C_{1-4}$ alkyl, and substituted or unsubstituted $C_{1-4}$ alkoxy, for example deuterium, halogen, methyl and methoxy.

In some embodiments $R_{6a}$ is selected from the group consisting of hydrogen, deuterium, halogen, hydroxyl, —OD, substituted or unsubstituted $C_{1-4}$ alkyl, and substituted or unsubstituted $C_{1-4}$ alkoxy, for example deuterium, halogen, methyl and methoxy.

In some embodiments $R_6$ and $R_{6a}$ are independently absent, halogen or $C_{1-4}$ alkyl.

In some embodiments $R_7$ is absent (e.g. when p is 0, or when an unsaturation is present) or selected from hydrogen, deuterium, halogen, and substituted or unsubstituted $C_{1-4}$ alkyl, for example hydrogen, fluoro and methyl.

In some embodiments $R_7$ is selected from the group consisting of hydrogen, deuterium, halogen, methyl and methoxy. In some embodiments, $R_7$ is selected from the group consisting of hydrogen or fluoro.

In some embodiments $R_8$ is selected from the group consisting of hydrogen, halogen, methyl, ethyl, propyl, methoxy, ethoxy, $C_{1-2}$-haloalkyl, and $C_{1-2}$-haloalkoxy.

In some embodiments $R_8$ is selected from the group consisting of hydrogen, halogen, methyl, ethyl, propyl, methoxy, ethoxy, $C_{1-2}$-haloalkyl, and $C_{1-2}$-haloalkoxy, e.g. hydrogen, —$CF_3$, —$CHF_2$, —$CF_2CF_3$, —$OCF_3$, —$OCF_2CF_3$ and —$OCHF_2$.

In some embodiments $R_8$ is hydrogen.
In some embodiments X is O.
In some embodiments A is —O—.
In some embodiments m, and n independently are selected from the group consisting of 0 and 1, for example m is 1 and n is 0 or 1.
In some embodiments A is —O— and m and n are 1.

In some embodiments A is —O— and m is 1 and n is 0.
In some embodiments A is a bond.
In some embodiments A is a bond and m is 1 and n is 1.
In certain embodiments a compound provided herein has hERG % inhibition of less than 65%. In some embodiments the hERG % inhibition is less than 50%. In some embodiments A is —S—.

Some embodiments relate to a compound, pharmaceutically acceptable salt, hydrate, solvate, polymorph, prodrug or stereoisomer according to Formula (II)

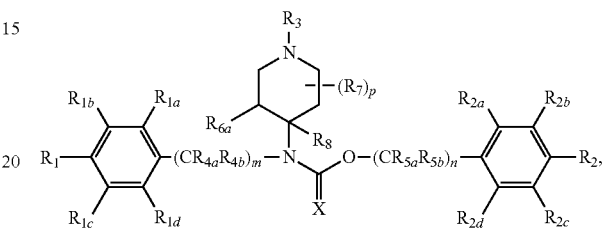

(II)

wherein $R_1$, $R_{1a}$, $R_{1b}$, $R_{1d}$, $R_2$, $R_{2a}$, $R_{2b}$, $R_{2c}$, $R_{2a}$, $R_3$, $R_{4a}$, $R_{4b}$, $R_{5a}$, $R_{5b}$, $R_{6a}$, $R_7$, $R_8$, X, m, n, and p are as defined in the embodiments disclosed above and in the appending claims.

In some embodiments $R_{1a}$, $R_{1b}$, $R_{1c}$, $R_{2a}$, $R_{2b}$, $R_{2c}$, $R_{2d}$, $R_{4a}$, $R_{4b}$, $R_{5a}$, $R_{5b}$, and $R_8$ are hydrogen; p is 0; $R_3$ is hydrogen or methyl; X is O; m is 1; n is 0 or 1; $R_1$ is fluoro and $R_{1d}$ is selected from the group consisting of hydrogen, hydroxyl, and halogen; $R_2$ is $C_{1-6}$ alkoxy; and $R_{6a}$ is hydrogen or halogen, e.g. fluoro.

Some embodiments relate to a compound, pharmaceutically acceptable salt, hydrate, solvate, polymorph, prodrug or stereoisomer according to Formula (VIII)

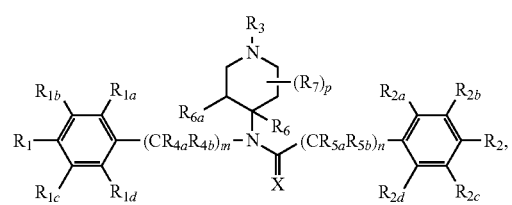

(VIII)

wherein $R_1$, $R_a$, $R_{1b}$, $R_{1c}$, $R_{1d}$, $R_2$, $R_{2a}$, $R_{2b}$, $R_{2c}$, $R_{2a}$, $R_3$, $R_{4a}$, $R_{4b}$, $R_{5a}$, $R_{5b}$, $R_{6a}$, $R_7$, $R_8$, X, m, n, and p are as defined in the embodiments disclosed above and in the appending claims.

In some embodiments $R_{1a}$, $R_{1b}$, $R_{1c}$, $R_{2a}$, $R_{2b}$, $R_{2c}$, $R_{2d}$, $R_{4a}$, $R_{4b}$, $R_{5a}$, $R_{5b}$, and $R_8$ are hydrogen; p is 0; $R_3$ is hydrogen or methyl; X is O; m is 1; n is 0 or 1; $R_1$ is fluoro and $R_{1d}$ is selected from the group consisting of hydrogen, hydroxyl, and halogen; $R_2$ is $C_{1-6}$ alkoxy; and $R_{6a}$ is hydrogen or halogen, e.g. fluoro.

In certain embodiments a compound provided herein has hERG % inhibition of less than 65%. In some embodiments the hERG % inhibition is less than 50%.

Some embodiments disclosed herein relate to a method for treating a disease in a patient comprising administering to the patient an effective amount of a compound, pharmaceutically acceptable salt, polymorph or stereoisomer of a compound according to Formulas (I)-(II), wherein the disease is selected from the group consisting of Abnormal hormonal activity, Alzheimer's disease, Alzheimer's disease dementia, Alzheimer's disease psychosis, Addiction (alcohol, cocaine, methamphetamine, nicotine and opioid), Addison's disease, ADHD, Alzheimer's disease psychosis, Affective disorders, Aggressiveness, Agitation, Akathisia, Alcohol addiction, Alcohol withdrawal, Amenorrhea, Amyotrophic lateral sclerosis, Anhedonia, Anorexia, Anti-NMDAR encephalitis, Anxiety, Appetite disorders, Asthma, Autism, Behavioral disorders, Behavioral disturbances associated with dementia, Binge eating disorder associated with impulse control disorder (ICD), Bipolar disorder, Blindness, Borderline disorder, Borderline personality disorder, Bradykinesia, Bulimia, Buying associated with ICD, Cardiac arrhythmia, Cerebral vascular accidents, Charles Bonnet disease, Chemotherapy-induced emesis, Childhood autism, Chronic pain, Chronic insomnia, cocaine addiction, Cognitive disorders, craniofacial pain, temporomandibular joint (TMJ)/temporomandibular disorder (TMD), Cushing's disease, Delusion, Dementia, Dementia with Lewy Body or Lewy Body dementia, dementia and psychosis associated with Creutzfeld-Jakob disease (CJD), Gerstmann-Strausser-Schenker disease (GSSD) and fatal familiar insomnia (FFI), Depression, Diabetes mellitus (non-insulin dependent), Diabetic peripheral neuropathy, Drug addiction, Double vision, Down's syndrome, Dyskinesia, Dysthymia, Dystonia, Ejaculatory problem, Emphysema, Epilepsy, Extrapyramidal disorder, Fibromyalgia, Frailty, Friedrich's Ataxia, Frontotemperal Dementia, Gambling associated with ICD, Galactorrhea, General anxiety disorder, Glaucoma, Hair loss or thinning, Hallucination, Headache, Hemorrhoids, Huntington's disease, Hyperprolactinemia, Hypertension, Hypersexuality associated with ICD, Hypotension, Hypoglutamateriga disorders, Impulse control disorder, Idiopathic thrombocytopenic purpura, Impotence, Incontinence, Increased intraocular pressure, Infertility, Inflammatory pain, Insomnia, Ischemia, Ischemic stroke, Lewy body disease (LBD), Learning disorders, Libido (decreased), Loss of libido, Low male fertility, Low sperm mobility, Lupus, Machado-Joseph disease, Major depression, Mania, Menopausal symptoms, Metabolic syndrome, methamphetamine addiction, Migraine, mild cognitive impairment (MCI), Motor tics, Multi-infarct dementia, Multiple sclerosis, Multiplex development disorder, Myocardial infarction, Myoclonus, Neuropathic pain, Neurodegenerative disorder, Neuropsychiatric disease, Nicotine addiction, Non motor symptoms of Parkinson's disease selected from dementia, depression, apathy, hallucinations, dribbling saliva (sialorrhea), constipation, pain, genitourinary problems and sleep disorders, Obsessive compulsive disorder, On/off phenomena, Opioid addiction, Osteoporosis, Pancreatis, Panic attacks, Parkinson's disease, Parkinson's disease dementia, Parkinson's disease psychosis, Periodic limb movement during sleep (PLMS), Peripheral vascular disease, Pituitary tumor, Postherpetic neuralgia, Progressive Supranucelar Palsy, Prion disease including Creutzfeld-Jakob disease (CJD), Gerstmann-Strausser-Schenker disease (GSSD) and fatal familiar insomnia (FFI), Prolactinoma, Pseudobulbar affect (PBA), Psychomotor slowing, Psychosis, Psychoses secondary to neurodegenerative disorders, Psychosomatic disorders, Psychotic depression, post-traumatic stress disorder (PTSD), Raynaud's disease, Reflex sympathetic dystrophy, Restless legs syndrome, Retinal disease, Schizoaffective disorders, Schizophrenia, negative symptoms of schizophrenia, cognitive impairment associated with schizophrenia, Sepsis, Serotonin syndrome, Sexual dysfunction, Sexual dysfunction associated with antidepressant use, Sleep apnea, Sleep disorders, Sleep maintenance insomnia, social anxiety disorder, Spinal injury, Spinocerebellar Atrophy, Suicidal tendency, Thrombosis, Thrombotic stroke, Thrombotic thrombocytopenic purpura, Tinnitus, Tiredness, Tourette's syndrome, Transient insomnia, Traumatic brain injury, Treatment-resistant depression, Treatment-resistant schizophrenia, Tremor, Vaginal dryness, Vasospasm Wakefulness, vascular dementia, Hallucinations associated with Parkinson's disease, Delusions associated with Parkinson's disease; cancer, brain cancer, glioma, Pancreatic cancer, Hypoactive sexual desire disorder, adult type 2 diabetes mellitus with Parkinson's disease or dementia and Liver fibrosis.

Suitable routes of administration of compounds of Formulas (I)-(II) may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tableting processes.

Pharmaceutical compositions for use as described herein thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

EXAMPLES

Unless otherwise stated, starting materials were obtained from commercial suppliers, such as (but not limited to); Chemtronica, Merck (Sigma-Aldrich), Fluorochem, Fisher, Bepharm, Broadpharm, Larodan, Activate Scientific, and Enamine.

Nuclear Magnetic Resonance (NMR) spectra were recorded on Varian instrument at 400 MHz, at 25° C. Chemical shifts are reported in ppm (δ) using the residual solvent as internal standard. Peak multiplicities are expressed as follow: s, singlet; d, doublet; t, triplet; q, quartet; p, pentet; h, heptet; m, multiplet; bs, broad singlet or combinations thereof, including but not limited to dd, doublet of doublets and dt, doublet of triplet.

LC-MS were acquired on an Agilent 1100 HPLC coupled with an Agilent MSD mass spectrometer operating in ES (+) ionization mode. Column: Waters symmetry 2.1×30 mm C18 or Chromolith RP-18 2×50 mm. Solvent A water+0.1% TFA and solvent B Acetonitrile+0.1% TFA. Wavelength: 254 nM Preparative HPLC were acquired on a Gilson system. Flow: 10 ml/min Column: kromasil 100-5-C18 column. Wavelength: 220 nM. Solvent A water+0.1% TFA and solvent B Acetonitrile+0.1% TFA. Gradient: 40% to 95% B in 15 min The following are examples of abbreviations used:
aq. aqueous
Cat catalytical
HPLC high performance liquid chromatography
MeOH methanol
EtOAc Ethylacetate
DIEA or DIPEA N,N-Diisopropylethylamine
HCl Hydrochloric acid
DMF N,N-dimethylformamide
THF Tetrahydrofuran
CDCl$_3$ Chloroform-d
DMSO-D6 Dimethylsulfoxide-d6
MgSO$_4$ Magnesium Sulfate
POCl$_3$ Phosphorus(V) oxychloride
KOH Potassium hydroxide
NaOH Sodium hydroxide
Na$_2$SO$_4$ Sodium Sulfate
K$_2$CO$_3$ Potassium carbonate
Na$_2$CO$_3$ Sodium carbonate
TFA Trifluoroacetic acid
Boc t-butoxycarbonyl
FMOC Fluorenylmethyloxycarbonyl
FMOC-Cl 9-Fluorenylmethoxycarbonyl chloride
TEOC 2-(trimetylsilyl)ethoxycarbonyl
equiv. equivalents
min minutes Preparation of Starting Materials and Intermediate Compounds Intermediate 1: [4-(propan-2-yloxy)phenyl]methanol

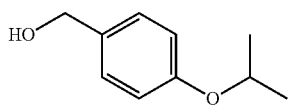

Ethyl 4-hydroxybenzoate (10.0 g, 60 mmol), potassium carbonate (180 mmol, 25.0 g) and 2-iodopropane (150 mmol, 14.9 ml) were stirred at 65° C. in dimethylformamide (40 ml) for 24 hours. The mixture was partitioned between diethyl ether and water, the organic phase was washed twice with water and finally with brine, then separated and evaporated to give ethyl 4-isopropoxybenzoate (12.59 g, 100% yield). This ester (10.0 g, 48 mmol) was dissolved in diethyl ether (50 ml) and dropped to a suspension of lithium aluminum hydride (48 mmol, 2.17 g) in diethyl ether (100 ml). The mixture was refluxed for 2 hours, then cooled and quenched with dropwise addition of methanol (10.0 ml) in diethyl ether (40 ml). The quenched mixture was partitioned between 5 M sodium hydroxide and diethyl ether, the organic phase was separated and washed with brine. The organic phase was dried and evaporated to give the title compound (7.85 g, 98% yield).

Intermediate 2: [4-(2-methylpropoxy)phenyl]methanol

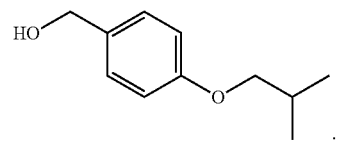

Ethyl 4-hydroxybenzoate (3.32 g, 20 mmol), potassium carbonate (11.0 g, 80 mmol), 1-bromo-2-methylpropane (5.4 ml, 50 mmol) and tetrabutylammonium iodide (738 mg, 2 mmol) were stirred at 70° C. in dimethylformamide (20 ml) for 26 hours. Water (50 ml) was added and the mixture was extracted with diethyl ether (2×200 ml). The organic phase was washed with water (3×100 ml), dried (sodium sulfate), filtered and concentrated to give ethyl 4-(2-methylpropoxy)benzoate (4.0 g, 90% yield). This ester (4.0 g, 18 mmol) was dissolved in diethyl ether (50 ml) and dropped to a suspension of lithium aluminum hydride (1.4 g, 36 mmol) in diethyl ether (30 ml). The mixture was refluxed for 16 hours, then cooled in an ice bath and quenched with water (1.4 ml), sodium hydroxide (15%, aqueous, 1.4 ml) and water (4.2 ml). The mixture was stirred for 20 minutes before it was filtered and concentrated to give the desired intermediate (3.0 g, 92%).

Intermediate 3: (4-methoxyphenyl)methanol

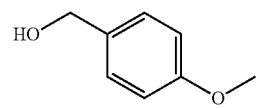

Methyl 4-methoxybenzoate (3.0 g, 16.6 mmol) in tetrahydrofuran (5 ml) was added dropwise to a suspension of lithium aluminum hydride (16.6 mmol, 635 mg) in tetrahydrofuran (10 ml) and the mixture was stirred at 40° C. for 1 hour. The reaction was worked up by sequential addition of water, sodium hydroxide (15%, aqueous), and water and gave the title compound as an oil (1.88 g, 82% yield).

Intermediate 4: 2-[4-(2-methylpropoxy)phenyl]ethan-1-ol

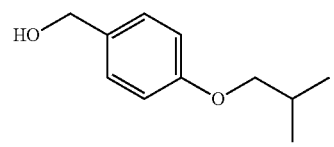

Methyl 2-(4-hydroxyphenyl)acetate (104 mmol, 17.5 g), potassium carbonate (312 mmol, 43 g) and tetrabutylammonium iodide (10 mmol, 3.7 g) were stirred in dimethylformamide (100 ml) and 1-bromo-2-methylpropane (260 mmol, 36 g) was added and the mixture was stirred at 75° C. After 24 hours the mixture was partitioned between diethyl ether and water, the organic phase was washed three times with water, then brine. The organic phase was dried and evaporated to give the alkylated ester as an oil. The oil was hydrolyzed in a mixture of methanol (50 ml), 5 M sodium hydroxide (50 ml) and water (50 ml), then after 6 hours acidified with 5 M hydrochloric acid and the precipitate was collected and gave the intermediate carboxylic acid (19.9 g, 95.5 mmol). This acid was dissolved in a mixture of dichloromethane (70 ml), dimethylformamide (30 µl) and thionyl chloride (35 ml). After stirring for 100 hours at room temperature the mixture was concentrated and gave the acid chloride, 2-[4-(2-methylpropoxy)phenyl]acetyl chloride, as an oil (22.08 g, 92% yield from methyl 2-(4-hydroxyphenyl) acetate). This oil (1.0 g, 4.42 mmol) was dissolved in tetrahydrofuran (5 ml) and added dropwise to a suspension of lithium aluminum hydride (4.41 mmol, 170 mg) in tetrahydrofuran (10 ml). The mixture was stirred 1 hour, then quenched with ethyl acetate (250 µl) and worked up by sequential addition of water, sodium hydroxide (15%, aqueous) and water. The crude material was purified by column chromatography using silicon dioxide gel, eluting with 25% ethyl acetate in petroleum ether to afford the title compound (639 mg, 74%).

Intermediate 5: 4-nitrophenyl [4-(propan-2-yloxy)phenyl] methyl carbonate

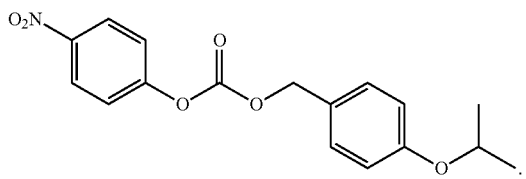 [SMILES: CC(C)Oc1ccc(COC(=O)Oc2ccc([N+](=O)[O-])cc2)cc1]

[4-(propan-2-yloxy)phenyl]methanol (12 mmol, 2.0 g) and 4-nitrophenyl-chloroformate (13.8 mmol, 90%, 3.1 g) were stirred in dichloromethane (20 ml) and a solution of pyridine (13.8 mmol, 1.13 ml) in dichloromethane (10 ml) was added dropwise during 1 hour. The mixture was stirred 72 hours, then concentrated and was purified by column chromatography using silicon dioxide gel, eluting with 20% ethyl acetate in petroleum ether to afford the title compound (2.82 g, 71%).

Intermediate 6: 4-nitrophenyl [4-(2-methylpropoxy)phenyl]methyl carbonate

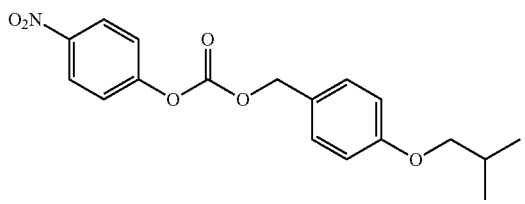 [SMILES: CC(C)COc1ccc(COC(=O)Oc2ccc([N+](=O)[O-])cc2)cc1]

The compound was prepared in analogy with intermediate 5, using [4-(2-methylpropoxy)phenyl]methanol instead of [4-(propan-2-yloxy)phenyl]methanol. Yield 207 mg, 60%.

Intermediate 7: N-[(2,4-difluorophenyl)methyl]-1-methylpiperidin-4-amine

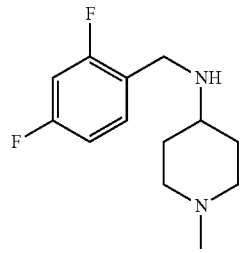 [SMILES: CN1CCC(NCc2ccc(F)cc2F)CC1]

2,4-difluorobenzylamine (4.0 g, 27.1 mmol) was dissolved in ethanol (30 ml) and N-methyl-4-piperidone (3.16 g, 27.1 mmol) was added followed by sodium triacetoxyborohydride (54.2 mmol, 11.85 g). The mixture was stirred at room temperature for 2 hours, then partitioned between diethyl ether and 2 M sodium hydroxide (100 ml). The organic phase was collected and extracted with 2M hydrochloric acid (50 ml), then the acidic aqueous phase was made basic with 5 M sodium hydroxide (30 ml) and extracted with diethyl ether. The organic extract was dried and evaporated to give the title compound as a yellow oil (5.96 g, 91% yield).

Intermediate 8: N-[(4-fluorophenyl)methyl]-1-methylpiperidin-4-amine

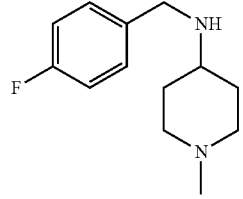 [SMILES: CN1CCC(NCc2ccc(F)cc2)CC1]

The compound was prepared in analogy with intermediate 7 using 4-fluorobenzylamine instead of 2,4-difluorobenzylamine. Yield 17.48 g, 97%.

Intermediate 9: N-[(4-chlorophenyl)methyl]-1-methylpiperidin-4-amine

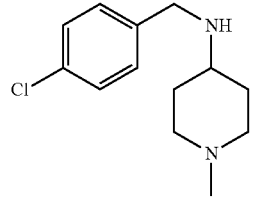 [SMILES: CN1CCC(NCc2ccc(Cl)cc2)CC1]

The compound was prepared in analogy with intermediate 7 using 4-chlorobenzylamine instead of 2,4-difluorobenzylamine. Yield 1.625 g, 98%.

Intermediate 10: 4-nitrophenyl N-[(2,4-difluorophenyl)methyl]-N-(1-methylpiperidin-4-yl)carbamate

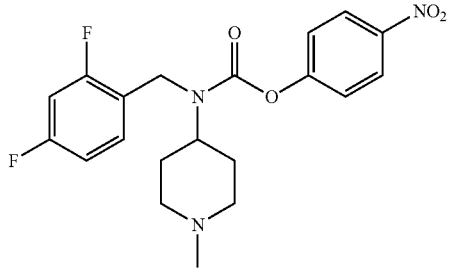 [SMILES: CN1CCC(N(Cc2ccc(F)cc2F)C(=O)Oc2ccc([N+](=O)[O-])cc2)CC1]

N-[(2,4-difluorophenyl)methyl]-1-methylpiperidin-4-amine (1.00 mg, 4.04 mmol) was dissolved in diethyl ether (10 ml) and a solution of p-nitrophenyl chloroformate (995 mg, 90%, 4.44 mmol) in diethyl ether (20 ml) was added which resulted in a precipitate. The suspension was stirred for 10 min, saturated aqueous sodium bicarbonate was added and the organic phase was separated, dried and evaporated to give an oil that was purified by column chromatography using silicon dioxide gel, eluting with methanol to afford the title compound (1.25 g, 76% yield).

Intermediate 11: 4-nitrophenyl N-[(4-fluorophenyl)methyl]-N-(1-methylpiperidin-4-yl)carbamate

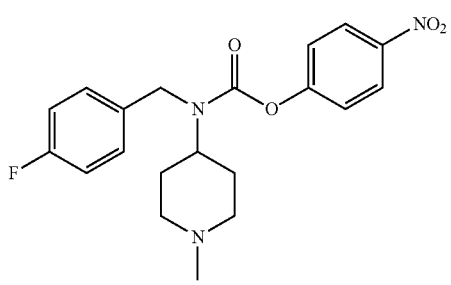 [SMILES: CN1CCC(N(Cc2ccc(F)cc2)C(=O)Oc2ccc([N+](=O)[O-])cc2)CC1]

The compound was prepared in analogy with intermediate 10 using N-[(4-fluorophenyl)methyl]-1-methylpiperidin-4-amine instead of N-[(2,4-difluorophenyl)methyl]-1-methylpiperidin-4-amine. Yield: 1.4 g, 40%.

Intermediate 12: tert-butyl (3R,4S)-4-[(chlorocarbonyl)[(4-fluorophenyl)methyl]amino]-3-fluoropiperidine-1-carboxylate and tert-butyl (3S,4R)-4-[(chlorocarbonyl)[(4-fluorophenyl)methyl]amino]-3-fluoropiperidine-1-carboxylate

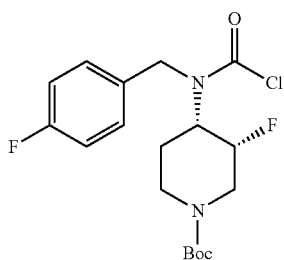

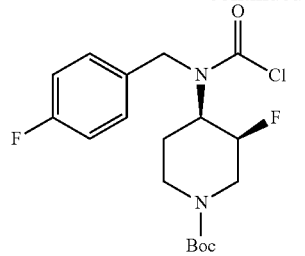

tert-Butyl-3-fluoro-4-oxopiperidine-1-carboxylate (3.0 g, 13.12 mmol) was dissolved in dichloromethane (15 ml) and 4-fluorobenzyl amine (13.8 mmol, 1.78 g) was added followed by sodium triacetoxyborohydride (22.3 mmol, 4.87 g) and the mixture was stirred for 3 hours, then partitioned between 0.5 M sodium hydroxide and dichloromethane. The organic phase was separated, dried, and the solvents were removed. The residue was purified by column chromatography using silicon dioxide gel, eluting with 33% to 50% ethyl acetate in petroleum ether to afford tert-butyl (3R,4S)-3-fluoro-4-{[(4-fluorophenyl)methyl]amino}piperidine-1-carboxylate and tert-butyl (3S,4R)-3-fluoro-4-{[(4-fluorophenyl)methyl]amino}piperidine-1-carboxylate (2.32 g, 54% yield), as a racemic mixture. This racemate (660 mg, 2.0 mmol) was dissolved in dichloromethane (5 ml) and pyridine (6.0 mmol, 489 μl) was added. The solution was dropped to an ice cooled mixture of diphosgene (1.5 mmol, 187 μl) in dichloromethane (2 ml). After 30 minutes the mixture was concentrated and subjected to column chromatography using silicon dioxide gel, eluting with 25% ethyl acetate in petroleum ether to afford the title compounds as a racemic mixture (718 mg, 91% yield).

Intermediate 13: (9H-fluoren-9-yl)methyl (3R,4S)-4-[(chlorocarbonyl)[(4-fluorophenyl)methyl]amino]-3-fluoropiperidine-1-carboxylate and (9H-fluoren-9-yl)methyl (3S,4R)-4-[(chlorocarbonyl)[(4-fluorophenyl)methyl]amino]-3-fluoropiperidine-1-carboxylate

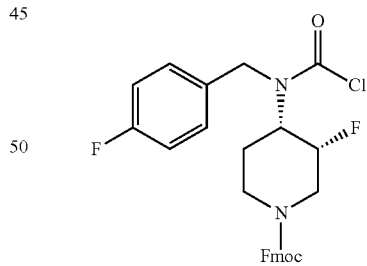

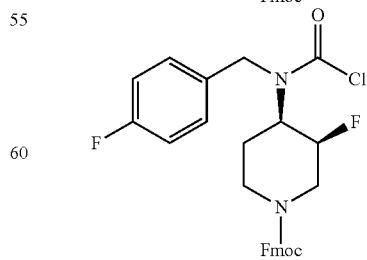

tert-Butyl-3-fluoro-4-oxopiperidine-1-carboxylate (2.0 g, 8.7 mmol) was deprotected in dichloromethane (15 ml) and trifluoroacetic acid (5 ml) for 2 hours and then evaporated and dissolved in dichloromethane (20 ml). The mixture was cooled on an ice bath and FMOC-Cl (13.05 mmol, 3.75 g) followed by pyridine (80 mmol, 6.5 ml) were added and the mixture was stirred at room temperature for 20 hours. The mixture was partitioned between dichloromethane and 0.5 M hydrochloric acid, the organic phase was evaporated and purified by column chromatography using silicon dioxide gel, eluting with 25% to 50% ethyl acetate in petroleum ether to afford the FMOC protected piperidone (2.09 g, 71% yield). This material (1.00 g, 2.94 mmol) was suspended in dichloromethane (15 ml), acetic acid (1 ml) and sodium triacetoxyborohydride (5.88 mmol, 1.285 g) followed by 4-fluorobenzylamine (3.24 mmol, 382 µl) were added. The mixture was stirred for 4 hours and then partitioned between dichloromethane and saturated sodium bicarbonate. The organic phase was evaporated and purified by column chromatography using silicon dioxide gel, eluting with 25% to 100% ethyl acetate in petroleum ether. The slower moving component was collected and gave 572 mg (43% yield) of (9H-fluoren-9-yl)methyl (3R,4S)-3-fluoro-4-{[(4-fluorophenyl)methyl]amino}piperidine-1-carboxylate and (9H-fluoren-9-yl)methyl (3S,4R)-3-fluoro-4-{[(4-fluorophenyl)methyl]amino}piperidine-1-carboxylate. These compounds (485 mg, 1.08 mmol) were dissolved in dichloromethane (5 ml), cooled on ice, and pyridine (4.32 mmol, 350 µl) followed by triphosgene (0.72 mmol, 214 mg, dissolved in 1 ml dichloromethane, corresponding to 2.16 mmol phosgene) were added. After 1 h the mixture was partitioned between 0.5 M hydrochloric acid and diethyl ether. The organic phase was dried, concentrated, and the residue was purified by column chromatography using silicon dioxide gel, eluting with 20% ethyl acetate in petroleum ether to afford the title compounds as a racemic mixture (498 mg, 90% yield).

Intermediate 14: 4-nitrophenyl 2-(trimethylsilyl)ethyl carbonate

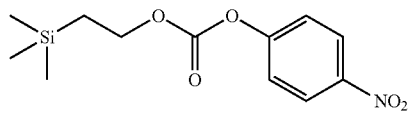 [SMILES: C[Si](C)(C)CCOC(=O)Oc1ccc([N+](=O)[O-])cc1]

2-trimethylsilylethanol (25.1 mmol, 3.0 g) was reacted with p-nitrophenyl chloroformate (27.6 mmol, 5.74 g) in pyridine (60 mmol, 4.9 ml) for 18 hours, then concentrated and purified by column chromatography using silicon dioxide gel, eluting with 20% ethyl acetate in petroleum ether to afford 4-nitrophenyl 2-(trimethylsilyl)ethyl carbonate (5.89 g, 82% yield).

Intermediate 15: 2-(trimethylsilyl)ethyl 4-[(chlorocarbonyl)[(2,4-difluorophenyl)methyl]amino]piperidine-1-carboxylate

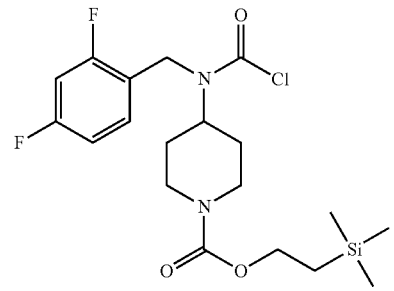 [SMILES: C[Si](C)(C)CCOC(=O)N1CCC(N(Cc2ccc(F)cc2F)C(=O)Cl)CC1]

tert-Butyl 4-oxopiperidine-1-carboxylate (7.0 g, 35 mmol) was deprotected in dichloromethane (25 ml) and trifluoroacetic acid (25 ml) for 1 hour, then the volatiles were removed which gave a semisolid trifluoroacetic acid salt of 4-piperidone. This salt (1.07 g, 5.03 mmol) was reacted with 4-nitrophenyl 2-(trimethylsilyl)ethyl carbonate (1.4 g, 4.7 mmol) in pyridine (5 ml) at 60° C. for 4 hours. The reaction mixture was concentrated and partitioned between 0.5 M sulfuric acid and ethyl acetate. The organic phase was concentrated, the residue was dissolved in diethyl ether and the organic phase was washed with aqueous 0.5 M sodium hydroxide several times. The organic phase was separated, dried, and evaporated to give the intermediate TEOC-protected 4-piperidone (994 mg, 86% yield). The TEOC-protected 4-piperidone (2.32 mmol, 600 mg) and 2,4-difluorobenzylamine (2.85 mmol, 420 mg) were mixed in ethanol (4 ml) and sodium triacetoxyborohydride (5.1 mmol, 1.11 g) was added. The mixture was stirred for 22 hours, then partitioned between diethyl ether and aqueous 0.5 M sodium hydroxide. The organic phase was dried, evaporated and gave an oil that was purified by column chromatography using silicon dioxide gel, eluting with ethyl acetate to afford 2-(trimethylsilyl)ethyl 4-{[(2,4-difluorophenyl)methyl]amino}piperidine-1-carboxylate (796 mg, 92% yield). This material (680 mg, 1.83 mmol) was dissolved in dichloromethane (3 ml), pyridine (7.32 mmol, 600 µl) was added and the solution was added slowly to an ice cooled mixture of triphosgene (1.22 mmol, 362 mg) in dichloromethane (3 ml). After 1 hour the mixture was partitioned between dichloromethane and aqueous 0.5 M hydrochloric acid. A yellow emulsion was formed. The organic phase was dried, evaporated and the residue was purified by column chromatography using silicon dioxide gel, eluting with 25% ethyl acetate in petroleum ether to afford the title compound (795 mg, 100% yield).

Intermediate 16: 4-(2-methylpropoxy)phenol

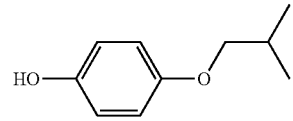

Hydroquinone (1.0 g, 9.0 mmol), cesium carbonate (4.5 mmol, 1.48 g), and 1-bromo-2-methylpropane (1.246 g, 9.0 mmol) in dimethylformamide (5 ml) were reacted at 70° C.

for 24 hours. The mixture was partitioned between 0.5 M hydrochloric acid and diethyl ether, the organic phase was dried and evaporated. The crude was purified by column chromatography using silicon dioxide gel, eluting with 20% ethyl acetate in petroleum ether to afford title compound (427 mg, 28% yield).

Intermediate 17: (7R,8aS)-N-[(4-fluorophenyl)methyl]-octahydroindolizin-7-amine and (7S,8aS)-N-[(4-fluorophenyl)methyl]-octahydroindolizin-7-amine

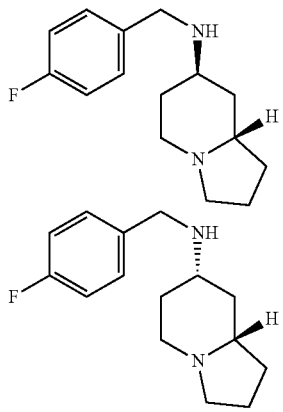

To a mixture of 4-fluorobenzylamine (438 mg, 3.5 mmol) and (8aS)-octahydro-indolizin-7-one (0.5 g, 3.5 mmol) in ethanol (50 ml) sodium triacetoxyborohydride (1.48 g, 7 mmol) was added at ambient temperature under nitrogen atmosphere. After stirring for 1 hour the mixture was evaporated to a solid and redissolved in ethyl acetate and water. The water phase was separated and washed with ethyl acetate. To the water phase was added sodium hydroxide (aqueous, 2M) and mixture was extracted with ethyl acetate. The organic phase was dried with magnesium sulfate and concentrated. The crude material was purified by column chromatography using silicon dioxide gel, eluting with 4% methanol in dichloromethane with 3% triethylamine to afford (7R,8aS)-N-[(4-fluorophenyl)methyl]-octahydroindolizin-7-amine (47 mg, faster eluting compound) and (7S,8aS)-N-[(4-fluorophenyl)methyl]-octahydroindolizin-7-amine (35 mg, slower eluting compound).

Intermediate 18: 2-[4-(2-methylpropoxy)phenyl]acetyl chloride

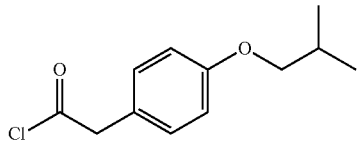

Thionyl chloride (21.6 ml, 298 mmol) was added to 2-[4-(2-methylpropoxy)-phenyl]acetic acid (6.21 g, 29.8 mmol) in dichloromethane (29.8 ml). The mixture was stirred at ambient temperature for 18 hours before it was concentrated to afford the title compound (6.77 g, 100%).

Intermediate 19: 2-[4-(propan-2-yloxy)phenyl]acetyl chloride

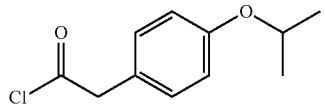

The compound was prepared in analogy with intermediate 18, using 2-[4-(propan-2-yloxy)phenyl]acetic acid.

Intermediate 20: 2-(4-methoxyphenyl)acetyl chloride

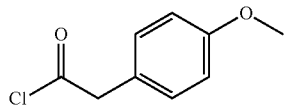

The compound was prepared in analogy with intermediate 18, using 2-(4-methoxyphenyl)acetic acid.

Intermediate 21: 2-[3-fluoro-4-(2-methylpropoxy)phenyl]acetyl chloride

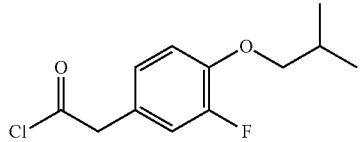 [SMILES: CC(C)COc1ccc(CC(=O)Cl)cc1F]

Sulfuric acid (49 µl, 882 µmol) was added to 2-(3-fluoro-4-hydroxyphenyl)acetic acid (500 mg, 2.94 mmol) in methanol (5 ml). After 1.5 hours, sodium acetate trihydrate (2 mmol) was added and the mixture was concentrated. The crude was suspended in ethyl acetate (5 ml), filtered and concentrated. Dimethylformamide (3 ml), isobutyl bromide (799 µl, 7.35 mmol), potassium carbonate (813 mg, 5.88 mmol) and tetrabutylammonium iodide (109 mg, 294 µmol) were added. The mixture was heated to 70° C. and stirred for 16 hours before it was cooled to ambient temperature and diluted with ethyl acetate (50 ml). The mixture was washed with water (5×30 ml), dried (phase-separator) and concentrated. The crude material was purified by column chromatography using silicon dioxide gel, eluting with 0-10% ethyl acetate in petroleum ether to give the intermediate ether (619 mg, 88%). The material was dissolved in methanol (4 ml) and sodium hydroxide (aqueous, 2M, 2.58 ml, 5.15 mmol) was added. After 1 hour, hydrochloric acid (aqueous, 2M, 3 ml) was added and the mixture was extracted with ethyl acetate (3×10 ml). The combined organic phases were dried (phase-separator), concentrated and re-dissolved in dichloromethane (2 ml). Thionyl chloride (1.87 ml, 25.8 mmol) was added and mixture was stirred at ambient temperature for 16 hours before it was concentrated to give the desired acyl chloride (633 mg, quantitative).

Intermediate 22: 2-[2-fluoro-4-(2-methylpropoxy)phenyl]acetyl chloride

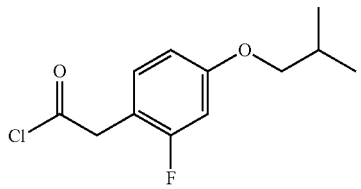 [SMILES: CC(C)COc1ccc(CC(=O)Cl)c(F)c1]

The compound was prepared in analogy with intermediate 21, using 2-(2-fluoro-4-hydroxyphenyl)acetic acid instead of 2-(3-fluoro-4-hydroxyphenyl)acetic acid.

Intermediate 23: 1-[4-(hydroxymethyl)phenoxy]-2-methylpropan-2-ol

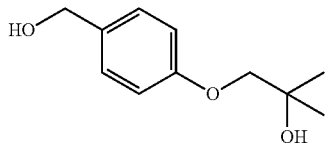

4-hydroxybenzaldehyde (24.1 mmol, 3.0 g) potassium carbonate (48.2 mmol, 6.7 g) were suspended in N,N-dimethylformamide (10 ml) and 1,2-epoxy-2-methylpropane (36.2 mmol, 3.32 ml) was added. The mixture was stirred at 60° C. for 18 hours and then partitioned between diethyl ether and water. The organic phase was washed with water, then brine, dried and evaporated to give the intermediate 4-O-alkylated benzaldehyde as an oil (1.0 g, 21% yield). This oil (1.0 g, 5.15 mmol) was dissolved in ethanol (10 ml) and sodium borohydride (5.15 mmol, 200 mg) was added in portions. The mixture was stirred 1 hour, then concentrated and water was added. The aqueous phase (pH 11) was extracted with diethyl ether. The organic phase was dried and evaporated to give the desired intermediate as a crystalline solid (1.0 g, 100%).

Intermediate 24: (4-cyclopropoxyphenyl)methanol

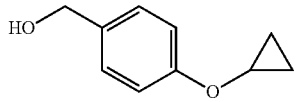 [SMILES: OCc1ccc(OC2CC2)cc1]

4-hydroxybenzaldehyde (500 mg, 4.0 mmol), cesium carbonate (10.0 mmol, 3.29 g) and sodium iodide (0.4 mmol, 61 mg) were suspended in N,N-dimethylacetamide (5 ml) and cyclopropyl bromide (20 mmol, 1.64 ml) was added. The mixture was stirred in a thick-walled glass flask at 150° C. for 20 hours and then partitioned between diethyl ether and water. The organic phase was washed with water, then brine, dried and evaporated to give an oil that was purified by column chromatography using silicon dioxide gel, eluting with 60% ethyl acetate in petroleum ether to afford the intermediate benzaldehyde as an oil (270 mg, 1.66 mmol, 41% yield). This oil (260 mg, 1.6 mmol) was dissolved in ethanol (3 ml) and sodium borohydride (0.8 mmol, 31 mg) was added. The mixture was stirred 1 hour, then concentrated and sodium hydroxide (0.2 M) was added. The aqueous phase was extracted with diethyl ether. The organic phase was concentrated to give the desired intermediate as a solid (236 mg, 90%).

Intermediate 25: [4-(prop-2-en-1-yloxy)phenyl]methanol

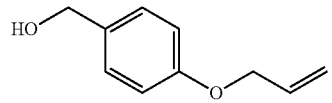

4-Hydroxybenzaldehyde (10.0 g, 80.25 mmol), potassium carbonate (163.8 mmol, 22.6 g), tetrabutylammonium iodide (1.0 mmol, 377 mg), allyl bromide (1.5 eq., 121 mmol, 10.6 ml) and N,N-dimethylformamide (4.0 ml) were stirred at 20° C. for 6 hours and then partitioned between water and diethyl ether. The organic phase was washed with water several times, then dried and evaporated to give 4-(allyloxy)benzaldehyde as an oil (13.3 g, 100%). This material (11.17 g, 68.8 mmol) was dissolved in ethanol (40 ml) and sodium borohydride (35 mmol, 1.351 g) was added in portions. The mixture was stirred 1 hour and then concentrated. Sodium hydroxide (5M, 30 ml) and water (100 ml) were added and the mixture was extracted with diethyl ether. The organic phase was washed with water and brine and then evaporated to give [4-(prop-2-en-1-yloxy)phenyl]methanol (10.49 g, 93%).

Intermediate 26: 2-(4-ethoxyphenyl)acetyl chloride

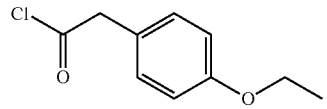

4-Ethoxyphenylacetic acid (10.0 g, 53.38 mmol) was refluxed for 2 hours in a mixture of dichloromethane (60 ml), thionyl chloride (40 ml) and N,N-dimethylformamide (200 µl). The mixture was evaporated and triturated in diethyl ether. The diethyl ether extract was evaporated to give the desired intermediate (10.98 g, 100% yield).

Intermediate 27: 2-(4-butoxyphenyl)acetyl chloride

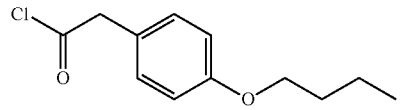

4-n-Butoxyphenylacetic acid (4.0 g, 18.81 mmol) was refluxed 2 hours in a mixture of dichloromethane (24 ml), thionyl chloride (16 ml) and N,N-dimethylformamide (160 µl). The mixture was evaporated and triturated in diethyl ether. The diethyl ether extract was evaporated to give the desired intermediate (4.35 g, 100% yield).

Intermediate 28: [4-(2-fluoroethoxy)phenyl]methanol

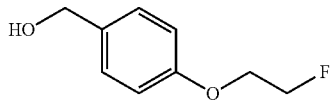 [SMILES: OCc1ccc(OCCF)cc1]

2-fluoroethanol (1.0 g, 95%, 14.8 mmol) was dissolved in dichloromethane (5.0 ml) and diisopropylethylamine (14.8 mmol, 2.59 ml) followed by p-toluenesulphonyl chloride (14.8 mmol, 2.85 g) were added. 4-dimethylaminopyridine (1.5 mmol, 187 mg) was added, the mixture was stirred 20 hours and then partitioned between 0.5 M HCl and diethyl ether, the organic phase was collected, dried, evaporated, and the crude was purified by column chromatography using silicon dioxide gel, eluting with 0-30% ethyl acetate in petroleum ether to afford the desired tosylated fluoroethanol (1.73 g, 54% yield). This material (700 mg, 3.2 mmol), 4-hydroxybenzaldehyde (3.5 mmol, 436 mg), tetrabutylammonium iodide (0.5 mmol, 190 mg), potassium carbonate (7.0 mmol, 967 mg) and DMF (4.0 ml) were stirred at 60° C. for 20 hours, then partitioned between water and diethyl ether, the organic phase was collected, dried, evaporated, and gave the intermediate 4-O-alkylated benzaldehyde (2.84 mmol, 479 mg, 88% yield). This aldehyde (374 mg, 2.22 mmol) was reduced with sodium borohydride (2.0 mmol, 76 mg) in ethanol (2.0 ml). The reaction was quenched with 1 M NaOH, partitioned between ether and NaOH (0.5 M), the organic phase was collected, dried, evaporated, and the crude was purified by column chromatography using silicon dioxide gel, eluting with 30-50% ethyl acetate in petroleum ether to afford the title compound (327 mg, 1.92 mmol, 86% yield).

Intermediate 29: 2-[4-(2-methylpropoxy)phenyl]acetyl chloride

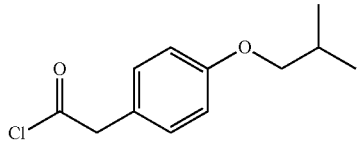

Thionyl chloride (21.6 ml, 298 mmol) was added to 2-[4-(2-methylpropoxy)-phenyl]acetic acid (6.21 g, 29.8 mmol) in dichloromethane (29.8 ml). The mixture was stirred at ambient temperature for 18 hours before it was concentrated to afford the title compound (6.77 g, 100%).

Intermediate 30: 2-[4-(propan-2-yloxy)phenyl]acetyl chloride

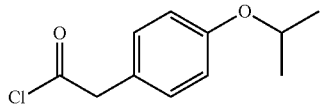

The compound was prepared in analogy with 2-[4-(2-methylpropoxy)phenyl]-acetyl chloride, using 2-[4-(propan-2-yloxy)phenyl]acetic acid.

Intermediate 31: [4-(1,1-difluoroethyl)phenyl]methanol

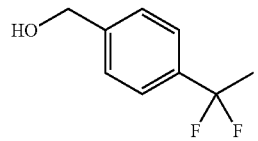

Sodium nitrite (232 mg, 3.36 mmol) was added in portions to [4-(1,1-difluoroethyl)phenyl]methanamine (43.5 mg, 0.25 mmol) in a mixture of water (0.5 ml) and acetic acid (0.5 ml) at 0° C. After 20 hours while warming to room temperature the mixture was diluted with ethyl acetate (2 ml), washed with sodium hydrogen carbonate (1 ml, sat. aq.), and sodium chloride (1 ml, sat. aq.). The organic phase was dried using a phase separator, concentrated to a yellow oil (51 mg).

Intermediate 32: N-{[2-(benzyloxy)-4-fluorophenyl]methyl}-1-methylpiperidin-4-amine

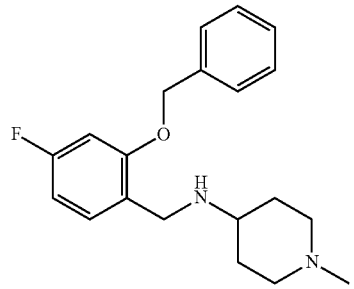 [SMILES: CN1CCC(NCc2ccc(F)cc2OCc2ccccc2)CC1]

Benzyl alcohol (0.77 g, 7.2 mmol) was added to a stirred suspension of potassium tert-butoxide (0.97 g, 8.6 mg) in dioxane (15 ml) at room temperature. After 10 minutes of stirring at room temperature 2,4-difluorobenzonitrile (1.00 g, 7.2 mmol) was added in one portion. After another 90 minutes water (10 ml) was added and the mixture extracted with diethyl ether (3×10 ml), the combined organic phases were dried using a phase separator and concentrated to solids. The crude material was purified by column chromatography using silicon dioxide gel, eluting with 25-50% dichloromethane in petroleum ether to afford 2-(benzyloxy)-4-fluorobenzonitrile as a white solid (1.33 g, 81%).

A cold solution of borane (1.4 ml, 1 M in tetrahydrofuran) was added to 2-(benzyloxy)-4-fluorobenzonitrile (208 mg, 915 µmol). After 15 hours of stirring at room temperature additional borane (1.4 ml, 1 M in tetrahydrofuran) was added. After another 19 hours of stirring additional borane (1.0 ml, 1 M in tetrahydrofuran) was added. After 3 hours the mixture was added to sodium hydroxide (5 ml, 1 M aqueous), extracted with ethyl acetate (3×5 ml), the combined organic phases were dried using a phase separator and concentrated afford [2-(benzyloxy)-4-fluorophenyl]methanamine as oil (260 mg, quantitative). This material was used without further purification.

N-Methyl-4-piperidone (150 mg, 1.32 mmol) was added to a stirred solution of [2-(benzyloxy)-4-fluorophenyl]methanamine (204 mg, 882 µmol) in ethanol (5 ml), after 5 minutes sodium triacetoxyborohydride (372 mg, 1.76 mmol) was added. After 6 hours the reaction mixture was concentrated, redissolved in dichloromethane (5 ml), washed with sodium hydroxide (5 ml, 1 M aqueous), the aqueous phase was extracted with additional dichloromethane (2×1 ml), the combined organic phases were dried using a phase separator, and concentrated to afford the desired intermediate as a yellow oil (253 mg, 87%).

Example 1: [4-(propan-2-yloxy)phenyl]methyl N-[(4-chlorophenyl)methyl]-N-(1-methylpiperidin-4-yl)carbamate (1)

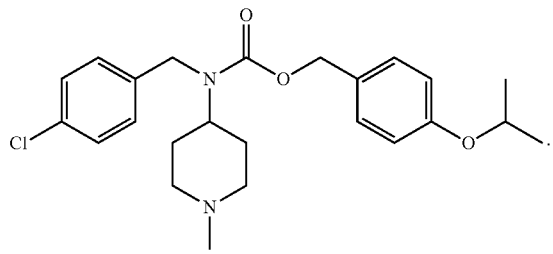 [SMILES: CC(C)Oc1ccc(COC(=O)N(Cc2ccc(Cl)cc2)C2CCN(C)CC2)cc1]

4-nitrophenyl [4-(propan-2-yloxy)phenyl]methyl carbonate (0.6 mmol, 200 mg) was reacted with N-[(4-chlorophenyl)methyl]-1-methylpiperidin-4-amine (0.5 mmol, 120 mg) in pyridine (1.0 ml) at 60° C. for 20 hours. The mixture was purified by column chromatography using silicon dioxide gel, eluting with 10% methanol in ethyl acetate to afford the title compound (44 mg, 20% yield) as an oil: $^1$H NMR (400 MHz, Chloroform-d) δ 7.44-6.95 (m, 6H), 6.81 (bs, 2H), 5.05 (bs, 2H), 4.53 (m, 1H), 4.38 (bs, 2H), 4.24-3.73 (m, 1H), 2.82 (d, 2H), 2.23 (s, 3H), 1.99 (bs, 2H), 1.57 (bs, 4H), 1.33 (d, 6H); LC-MS: 431.3 [M+H]$^+$.

Example 2: [4-(2-methylpropoxy)phenyl]methyl N-[(4-fluorophenyl)methyl]-N-(1-methylpiperidin-4-yl)carbamate (2)

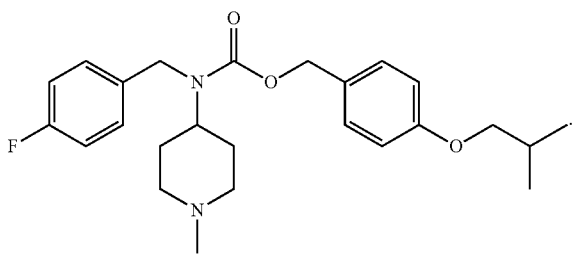 [SMILES: CC(C)COc1ccc(COC(=O)N(Cc2ccc(F)cc2)C2CCN(C)CC2)cc1]

The compound was prepared in analogy to example 1 using 4-nitrophenyl [4-(2-methylpropoxy)phenyl]methyl carbonate and N-[(4-fluorophenyl)methyl]-1-methylpiperidin-4-amine. Yield: 56 mg, 27% $^1$H NMR (400 MHz, Methanol-d) δ 7.44-7.05 (m, 4H), 7.05-6.75 (m, 4H), 5.07 (bs, 2H), 4.45 (bs, 2H), 4.10-3.70 (m, 1H), 3.73 (d, 2H), 2.85 (d, 2H), 2.22 (s, 3H), 2.10-1.90 (m, 3H), 1.76 (m, 2H), 1.59 (bs, 2H), 1.03 (d, 6H); LC-MS: 429.2 [M+H]$^+$.

Example 3: [4-(propan-2-yloxy)phenyl]methyl N-[(4-fluorophenyl)methyl]-N-[(3R,4S)-3-fluoropiperidin-4-yl]carbamate (3a) and [4-(propan-2-yloxy)phenyl]methyl N-[(4-fluorophenyl)methyl]-N-[(3S,4R)-3-fluoropiperidin-4-yl]carbamate (3b)

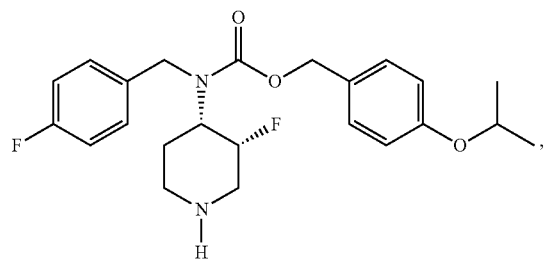

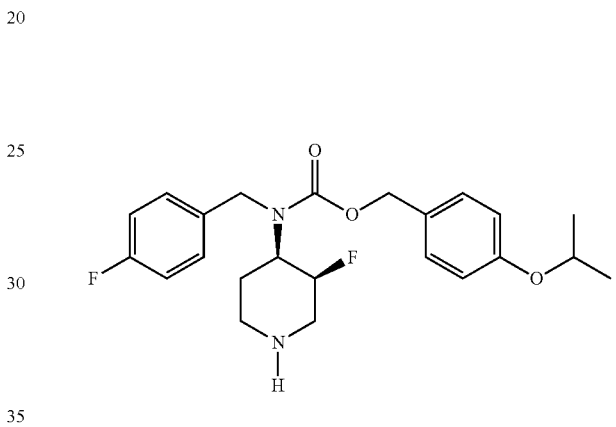

(9H-fluoren-9-yl)methyl (3R,4S)-4-[(chlorocarbonyl)[(4-fluorophenyl)methyl]-amino]-3-fluoropiperidine-1-carboxylate and (9H-fluoren-9-yl)methyl (3S,4R)-4-[(chlorocarbonyl)[(4-fluorophenyl)methyl]amino]-3-fluoropiperidine-1-carboxylate (1:1, 134 mg, 0.262 mmol) were dissolved in tetrahydrofuran (2 ml) and a premixed solution of sodium hydride (0.262 mmol, 10.5 mg) and [4-(propan-2-yloxy)phenyl]methanol (0.262 mmol, 44 mg) in tetrahydrofuran (1 ml) was added. After 1 hour more [4-(propan-2-yloxy)phenyl]methanol (22 mg) and sodium hydride (10 mg) were added. The mixture was stirred 1 hour and then applied directly onto a short silicon dioxide gel column and eluted with ethyl acetate. The crude material was purified by column chromatography using silicon dioxide gel, eluting with 20% to 33% ethyl acetate in petroleum ether to afford the intermediate FMOC protected carbamate (61 mg, 0.095 mmol, 36% yield). This material was dissolved in methanol (3 ml) and 2 M sodium hydroxide (0.2 ml) was added and the mixture was stirred for 10 minutes and then partitioned between diethyl ether and 1 M sodium hydroxide. The organic phase was concentrated and the residue was purified by column chromatography using silicon dioxide gel, eluting with 10% to 15% methanol in ethyl acetate to afford the title compound as a racemic mixture (36 mg, 90% yield): $^1$H NMR (400 MHz, Chloroform-d) δ 7.38-7.01 (m, 4H), 7.00-6.68 (m, 4H), 5.22-4.94 (m, 2H), 4.91-4.63 (m, 2H), 4.61-4.48 (m, 1H), 4.43 (d, 1H), 4.47-3.99 (m, 1H), 3.26 (t, 1H), 3.10 (d, 1H), 2.94-2.47 (m, 2H), 2.00-1.73 (m, 2H), 1.51-1.38 (m, 1H), 1.34 (d, 6H); LC-MS: 419.3 [M+H]$^+$.

Example 4: [4-(propan-2-yloxy)phenyl]methyl N-[(3R,4S)-3-fluoro-1-methylpiperidin-4-yl]-N-[(4-fluorophenyl)methyl]carbamate (4a) and [4-(propan-2-yloxy)phenyl]methyl N-[(3S,4R)-3-fluoro-1-methylpiperidin-4-yl]-N-[(4-fluorophenyl)methyl]carbamate (4b)

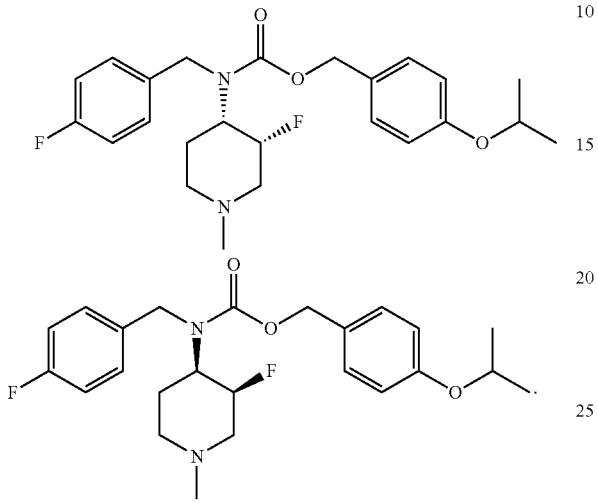

[4-(propan-2-yloxy)phenyl]methyl N-[(4-fluorophenyl)methyl]-N-[(3R,4S)-3-fluoropiperidin-4-yl]carbamate and [4-(propan-2-yloxy)phenyl]methyl N-[(4-fluorophenyl)methyl]-N-[(3S,4R)-3-fluoropiperidin-4-yl]carbamate (1:1, 30 mg, 0.0717 mmol) was dissolved in tetrahydrofuran (2 ml) and formaldehyde (37%, 0.215 mmol, 16 μl) and sodium triacetoxyborohydride (0.215 mmol, 47 mg) were added. After 1 hour the mixture was partitioned between diethyl ether and 0.5 M sodium hydroxide, the organic phase was dried and evaporated and the crude material was purified by column chromatography using silicon dioxide gel, eluting with 10% methanol in ethyl acetate to afford the title compound as a racemic mixture (30 mg, 96% yield): $^1$H NMR (400 MHz, Chloroform-d) δ 7.36-7.01 (m, 4H), 7.00-6.69 (m, 4H), 5.20-4.96 (m, 2H), 4.96-4.62 (m, 2H), 4.61-4.47 (m, 1H), 4.41 (d, 1H), 4.33-3.88 (m, 1H), 3.13 (t, 1H), 2.87 (d, 1H), 2.27 (s, 3H), 2.22-1.92 (m, 3H), 1.43 (m, 1H), 1.33 (d, 6H); LC-MS: 433.3 [M+H]$^+$.

Example 5: [4-(2-methylpropoxy)phenyl]methyl N-[(4-fluorophenyl)methyl]-N-[(3R,4S)-3-fluoropiperidin-4-yl]carbamate (5a) and [4-(2-methylpropoxy)phenyl]methyl N-[(4-fluorophenyl)methyl]-N-[(3S,4R)-3-fluoropiperidin-4-yl]carbamate (5b)

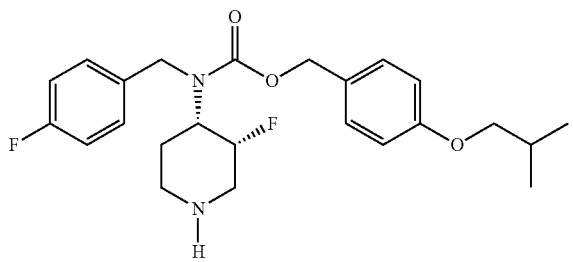

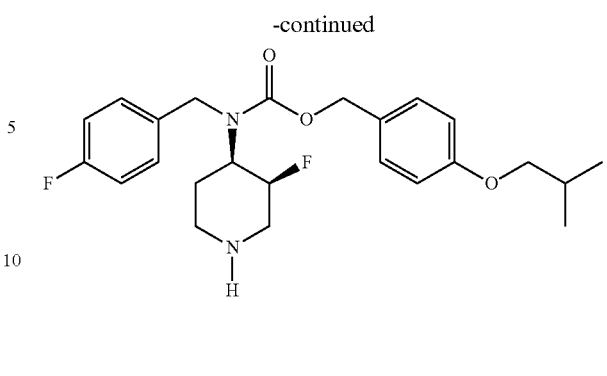

(9H-fluoren-9-yl)methyl (3R,4S)-4-[(chlorocarbonyl)[(4-fluorophenyl)methyl]-amino]-3-fluoropiperidine-1-carboxylate and (9H-fluoren-9-yl)methyl (3S,4R)-4-[(chlorocarbonyl)[(4-fluorophenyl)methyl]amino]-3-fluoropiperidine-1-carboxylate (1:1, 150 mg, 0.294 mmol) was dissolved in tetrahydrofuran (2 ml), cooled on an ice bath and a premixed solution of sodium hydride (0.32 mmol, 14 mg) and [4-(2-methylpropoxy)phenyl]methanol (0.32 mmol, 59 mg) in tetrahydrofuran (1 ml) was added dropwise. The mixture was stirred at room temperature for 72 hours and then partitioned between 0.2 M sodium hydroxide and diethyl ether. The diethyl ether phase was evaporated and methanol (4 ml) and 2 M sodium hydroxide (0.3 ml) were added. The mixture was stirred at room temperature for 1 hour. Dioxane (1 ml) was added to dissolve the precipitate and after 1 hour of stirring the mixture was partitioned between 0.2 M sodium hydroxide and diethyl ether and the organic phase was collected and evaporated. The above procedure was repeated once more on the same scale. The two concentrated organic phases were pooled together and purified by column chromatography using silicon dioxide gel, eluting with 0% to 10% methanol in ethyl acetate to afford the title compounds as a racemic mixture (38 mg, 15% yield): $^1$H NMR (400 MHz, Chloroform-d) δ 7.38-6.99 (m, 4H), 6.99-6.70 (m, 4H), 5.22-4.96 (m, 2H), 4.93-4.51 (m, 2H), 4.49-4.00 (m, 2H), 3.70 (d, 2H), 3.25 (t, 1H), 3.10 (d, 1H), 2.97-2.49 (m, 2H), 2.18 (s, 1H), 2.08 (m, 1H), 1.87 (dq, 1H), 1.43 (d, 1H), 1.02 (d, 6H); LC-MS: 433.3 [M+H]$^+$.

Example 6: [4-(2-methylpropoxy)phenyl]methyl N-[(3R,4S)-3-fluoro-1-methylpiperidin-4-yl]-N-[(4-fluorophenyl)methyl]carbamate (6a) and [4-(2-methylpropoxy)phenyl]methyl N-[(3S,4R)-3-fluoro-1-methylpiperidin-4-yl]-N-[(4-fluorophenyl)methyl]carbamate (6b)

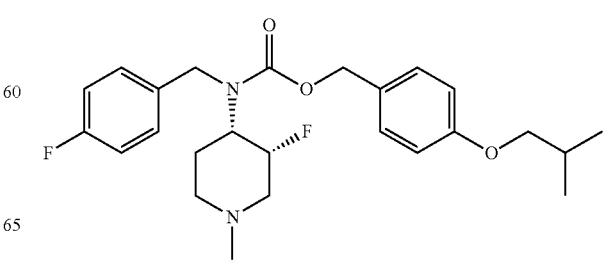

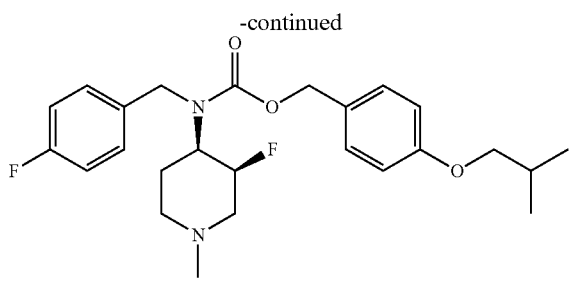

4-(2-methylpropoxy)phenyl]methyl N-[(4-fluorophenyl)methyl]-N-[(3R,4S)-3-fluoropiperidin-4-yl]carbamate and [4-(2-methylpropoxy)phenyl]methyl N-[(4-fluorophenyl)methyl]-N-[(3S,4R)-3-fluoropiperidin-4-yl]carbamate (1:1, 31 mg, 0.0717 mmol) was dissolved in tetrahydrofuran (2 ml) and formaldehyde (37%, 0.215 mmol, 16 µl) followed by sodium triacetoxyborohydride (0.215 mmol, 47 mg) were added. After 3 hours the mixture was partitioned between diethyl ether and 0.5 M sodium hydroxide, the organic phase was dried, evaporated and the residue was purified by column chromatography using silicon dioxide gel, eluting with 0% to 5% methanol in ethyl acetate to afford the title compounds as a racemic mixture (27 mg, 84% yield): $^1$H NMR (400 MHz, Chloroform-d) δ 7.38-7.00 (m, 4H), 7.00-6.73 (m, 4H), 5.26-4.95 (m, 2H), 4.95-4.58 (m, 2H), 4.41 (d, 1H), 4.34-3.87 (m, 1H), 3.71 (d, 2H), 3.13 (t, 1H), 2.87 (d, 1H), 2.27 (s, 3H), 2.22-1.89 (m, 4H), 1.52-1.34 (m, 1H), 1.02 (d, 6H); LC-MS: 447.4 [M+H]$^+$.

Example 7: 4-(2-methylpropoxy)phenyl N-[(4-fluorophenyl)methyl]-N-[(3R,4S)-3-fluoropiperidin-4-yl]carbamate (7a) and 4-(2-methylpropoxy)phenyl N-[(4-fluorophenyl)-methyl]-N-[(3S,4R)-3-fluoropiperidin-4-yl]carbamate (7b)

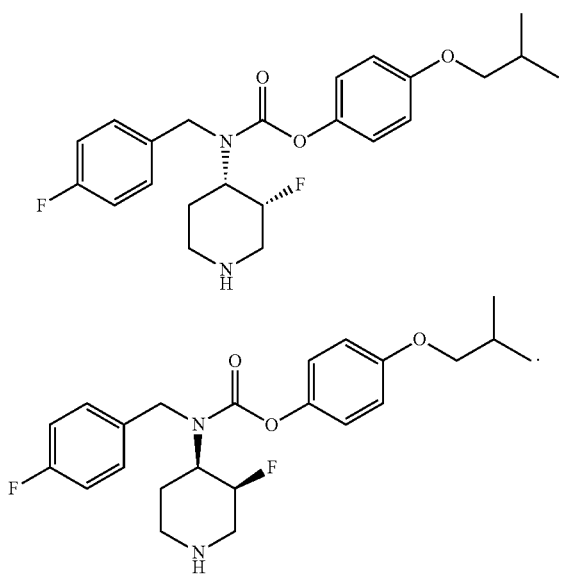

(9H-fluoren-9-yl)methyl (3R,4S)-4-[(chlorocarbonyl)[(4-fluorophenyl)methyl]-amino]-3-fluoropiperidine-1-carboxylate and (9H-fluoren-9-yl)methyl (3S,4R)-4-[(chlorocarbonyl)[(4-fluorophenyl)methyl]amino]-3-fluoropiperidine-1-carboxylate (1:1, 52 mg, 0.1 mmol) was dissolved in tetrahydrofuran (1 ml), cooled on an ice bath and a suspension of 4-(2-methylpropoxy)phenol (18.3 mg, 0.11 mmol) and sodium hydride (0.2 mmol, 8 mg) in tetrahydrofuran (1 ml) was added in one portion. After 1 hour, the mixture was partitioned between diethyl ether and 0.1 M sodium hydroxide, the organic phase was separated and evaporated. The residue was dissolved in methanol (3 ml) and sodium hydroxide (2 M, 0.2 ml) was added. After 1 hour, the mixture was evaporated, partitioned between 0.5 M sodium hydroxide and dichloromethane. The organic phase was separated, dried, and the residue was purified by column chromatography using silicon dioxide gel, eluting with 10% to 15% methanol in ethyl acetate to afford the title compounds as a racemic mixture (33 mg, 78% yield): $^1$H NMR (400 MHz, Methanol-d4) δ 7.36 (t, 2H), 7.20-6.75 (m, 6H), 5.10-4.30 (m, 4H), 3.73 (d, 2H), 3.26 (t, 1H), 3.10 (d, 1H), 2.86 (dd, 1H), 2.71 (t, 1H), 2.15-1.94 (m, 2H), 1.60 (d, 1H), 1.04 (d, 6H); LC-MS: 419.3 [M+H]$^+$.

Example 8: 4-(2-methylpropoxy)phenyl N-[(3R,4S)-3-fluoro-1-methylpiperidin-4-yl]-N-[(4-fluorophenyl)methyl]carbamate (8a) and 4-(2-methylpropoxy)phenyl N-[(3S,4R)-3-fluoro-1-methylpiperidin-4-yl]-N-[(4-fluorophenyl)methyl]carbamate (8b)

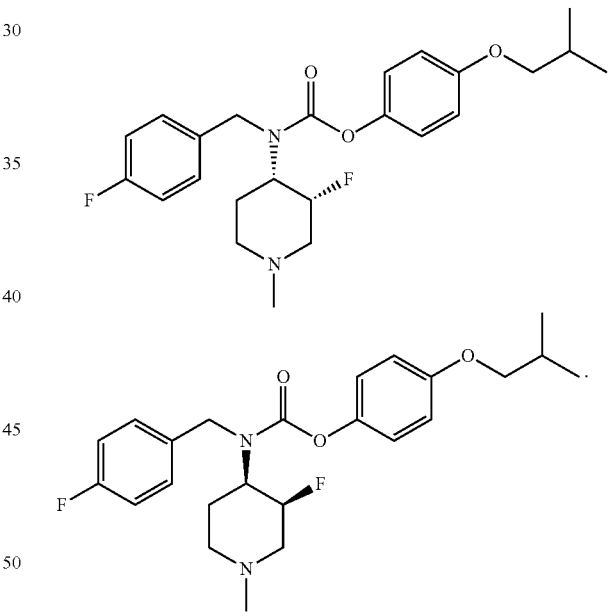

4-(2-methylpropoxy)phenyl N-[(4-fluorophenyl)methyl]-N-[(3R,4S)-3-fluoropiperidin-4-yl]carbamate and 4-(2-methylpropoxy)phenyl N-[(4-fluorophenyl)methyl]-N-[(3S,4R)-3-fluoropiperidin-4-yl]carbamate (1:1, 28 mg, 0.067 mmol) was dissolved in tetrahydrofuran (2 ml) and formaldehyde (0.21 mmol, 16 µl) followed by sodium triacetoxyborohydride (0.21 mmol, 47 mg) were added. The mixture was stirred 4 hours and then concentrated and partitioned between diethyl ether and 0.2 M sodium hydroxide. The organic phase was evaporated and the residue was purified by column chromatography using silicon dioxide gel, eluting with 0% to 10% methanol in ethyl acetate to afford the title compounds as a racemic mixture (27 mg, 93%): $^1$H NMR (400 MHz, Chloroform-d) δ 7.26 (bs, 2H), 7.10-6.75

(m, 6H), 4.94 (d, 1H), 4.93 (d, 1H), 4.65-4.40 (m, 1H), 4.27 (dd, 1H), 3.67 (d, 2H), 3.17 (t, 1H), 2.93 (d, 1H), 2.30 (s, 3H), 2.35-1.90 (m, 4H), 1.54 (d, 1H), 1.00 (d, 6H); LC-MS: 433.3 [M+H]$^+$.

Example 9: 2-[4-(2-methylpropoxy)phenyl]ethyl N-[(4-fluorophenyl)methyl]-N-[(3R,4S)-3-fluoropiperidin-4-yl]carbamate; trifluoroacetic acid (9a) and 2-[4-(2-methylpropoxy)phenyl]ethyl N-[(4-fluorophenyl)methyl]-N-[(3S,4R)-3-fluoropiperidin-4-yl]carbamate; trifluoroacetic acid (9b)

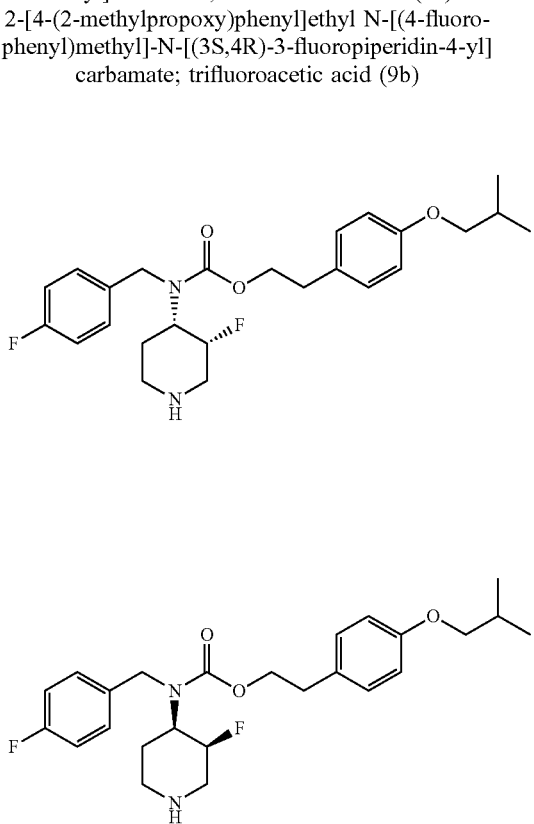

tert-butyl (3R,4S)-4-[(chlorocarbonyl)[(4-fluorophenyl)methyl]amino]-3-fluoropiperidine-1-carboxylate and tert-butyl (3S,4R)-4-[(chlorocarbonyl)[(4-fluorophenyl)methyl]amino]-3-fluoropiperidine-1-carboxylate (1:1, 150 mg, 0.38 mmol) was dissolved in tetrahydrofuran (2 ml) and a suspension of 2-[4-(2-methylpropoxy)phenyl]ethan-1-ol (0.57 mmol, 113 mg) and sodium hydride (0.75 mmol, 30 mg) in tetrahydrofuran (1 ml) was added dropwise, the temperature was then raised to 60° C. and the mixture was stirred for 3 hours. The mixture was partitioned between diethyl ether and 0.2 M sodium hydroxide, the organic phase was concentrated and the residue was purified by column chromatography using silicon dioxide gel, eluting with 20% ethyl acetate in petroleum ether to afford the Boc protected carbamate (126 mg, 0.23 mmol, 60% yield). This was deprotected in dichloromethane (2 ml) and trifluoroacetic acid (1 ml). After 30 min the mixture was evaporated to dryness and gave the title compounds as a racemic mixture (152 mg, 100% yield): $^1$H NMR (400 MHz, Chloroform-d) δ 9.49 (bs, 1H), 8.15 (bs, 1H), 7.24-6.63 (m, 8H), 5.25-3.90 (m, 6H), 3.67 (d, 2H), 3.67-2.68 (m, 6H), 2.29 (q, 1H), 2.05 (m, 1H), 1.62 (m, 1H), 1.02 (d, 6H); LC-MS: 447.4 [M+H]$^+$.

Example 10: 2-[4-(2-methylpropoxy)phenyl]ethyl N-[(3R,4S)-3-fluoro-1-methylpiperidin-4-yl]-N-[(4-fluorophenyl)methyl]carbamate (10a) and 2-[4-(2-methyl-propoxy)phenyl]ethyl N-[(3S,4R)-3-fluoro-1-methylpiperidin-4-yl]-N-[(4-fluorophenyl)-methyl] carbamate (10b)

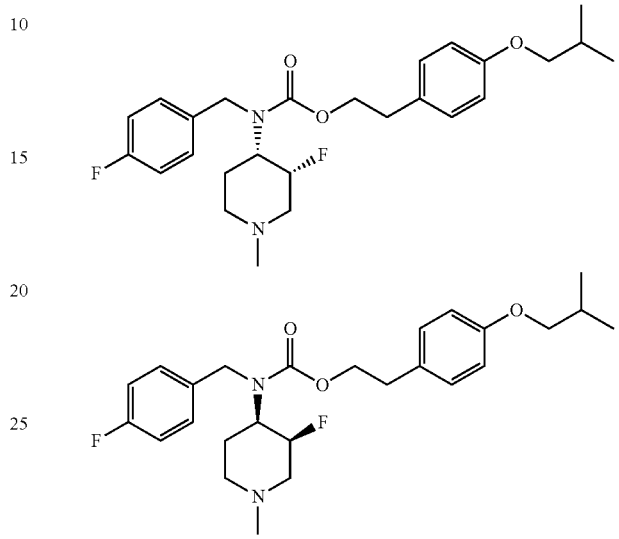

2-[4-(2-methylpropoxy)phenyl]ethyl N-[(4-fluorophenyl)methyl]-N-[(3R,4S)-3-fluoropiperidin-4-yl]carbamate and 2-[4-(2-methylpropoxy)phenyl]ethyl N-[(4-fluorophenyl)methyl]-N-[(3S,4R)-3-fluoropiperidin-4-yl]carbamate (1:1, 143 mg, 0.21 mmol) was dissolved in tetrahydrofuran (3 ml) and formaldehyde (0.67 mmol, 50 µl) followed by sodium triacetoxyborohydride (0.67 mmol, 147 mg) were added. The mixture was stirred for 20 hours and then partitioned between diethyl ether and 0.5 M sodium hydroxide. The organic phase was evaporated and the residue was purified by column chromatography using silicon dioxide gel, eluting with 10% methanol in ethyl acetate and an additional column chromatography using silicon dioxide gel, eluting with 0% to 5% methanol in ethyl acetate to afford the title compounds as a racemic mixture (40 mg, 41% yield): $^1$H NMR (400 MHz, Chloroform-d) δ 7.29-6.60 (m, 8H), 4.99-4.50 (m, 2H), 4.49-4.02 (m, 4H), 3.67 (d, 2H), 3.10 (m, 1H), 2.86 (m, 3H), 2.27 (s, 3H), 2.23-1.74 (m, 4H), 1.38 (bs, 1H), 1.02 (d, 6H); LC-MS: 461.3 [M+H]$^+$.

Example 11: [4-(propan-2-yloxy)phenyl]methyl N-[(2,4-difluorophenyl)methyl]-N-(piperidin-4-yl)carbamate (11)

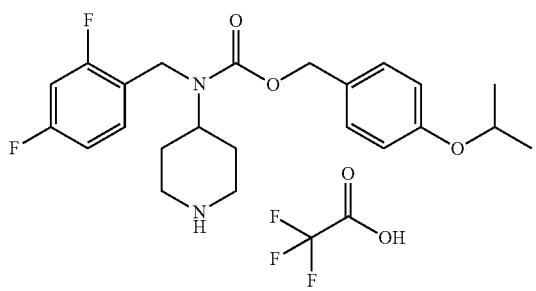

2-(trimethylsilyl)ethyl 4-[(chlorocarbonyl)[(2,4-difluorophenyl)methyl]amino]piperidine-1-carboxylate (117 mg, 0.27 mmol) was stirred in tetrahydrofuran (1 ml) and a premixed solution of [4-(propan-2-yloxy)phenyl]methanol (60.2 mg, 0.351 mmol) and sodium hydride (16.5 mg, 0.41 mmol) in tetrahydrofuran (1 ml) was added. The mixture was stirred for 3 hours, then partitioned between diethyl ether and 0.5 M sodium hydroxide, the organic phase was dried, evaporated, and the residue was purified by column chromatography using silicon dioxide gel, eluting with 20% ethyl acetate in petroleum ether to give the intermediate TEOC protected carbamate (136 mg, 89%). This material (133 mg, 0.236 mmol) was dissolved in tetrahydrofuran (2 ml) and tetrabutylammonium fluoride (1 M solution in tetrahydrofuran, 0.994 mmol, 0.994 ml) was added. The mixture was stirred 4 hours, then partitioned between diethyl ether and 0.5 M sodium hydroxide. The organic phase was collected, evaporated, and the residue was purified by column chromatography using silicon dioxide gel, eluting with methanol to afford the title compound (81 mg, 82% yield): $^1$H NMR (400 MHz, Chloroform-d) δ 7.45-6.98 (m, 3H), 6.96-6.60 (m, 4H), 5.22-4.95 (m, 2H), 4.63-4.32 (m, 3H), 4.26-3.80 (m, 1H), 3.07 (d, 2H), 2.74-2.44 (m, 2H), 1.75-1.41 (m, 5H), 1.34 (d, 6H); LC-MS: 419.2 [M+H]$^+$.

Example 12: [4-(propan-2-yloxy)phenyl]methyl N-[(4-fluorophenyl)methyl]-N-(1-methylpiperidin-4-yl)carbamate (12)

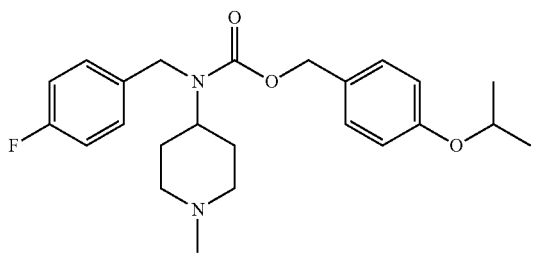 [SMILES: CC(C)Oc1ccc(COC(=O)N(Cc2ccc(F)cc2)C2CCN(C)CC2)cc1]

The compound was prepared in analogy with example 1 using N-[(4-fluorophenyl)methyl]-1-methylpiperidin-4-amine and 4-nitrophenyl [4-(propan-2-yloxy)phenyl]methyl carbonate. Yield: 87 mg, 25%: $^1$H NMR (400 MHz, Chloroform-d) δ 7.41-7.00 (m, 4H), 7.00-6.68 (m, 4H), 5.06 (bs, 2H), 4.53 (m, 1H), 4.39 (bs, 2H), 4.22-3.70 (m, 1H), 2.82 (d, 2H), 2.21 (s, 3H), 2.09-1.82 (m, 2H), 1.79-1.50 (m, 4H), 1.32 (d, 6H); LC-MS: 415.2 [M+H]$^+$.

Example 13: [4-(propan-2-yloxy)phenyl]methyl N-[(2,4-difluorophenyl)methyl]-N-(1-methylpiperidin-4-yl)carbamate (13)

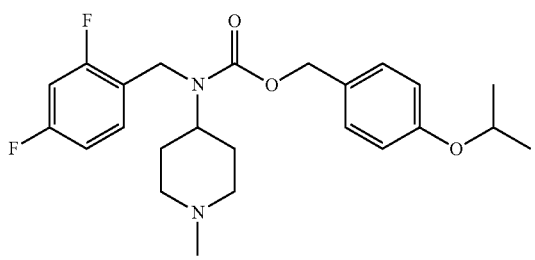 [SMILES: CC(C)Oc1ccc(COC(=O)N(Cc2ccc(F)cc2F)C2CCN(C)CC2)cc1]

[4-(propan-2-yloxy)phenyl]methanol (1.25 mmol, 208 mg) was dissolved in tetrahydrofuran (2.0 ml) and sodium hydride (1.62 mmol, 60%, 65 mg) was added in one portion. After gas evolution ceased the suspension was added to a solution of 4-nitrophenyl N-[(2,4-difluorophenyl)methyl]-N-(1-methylpiperidin-4-yl)carbamate (136 mg, 0.33 mmol) dissolved in tetrahydrofuran (2.0 ml). The mixture was stirred for 6 hours, then partitioned between diethyl ether and 0.5 M sodium hydroxide, the organic phase was collected, dried, and purified by column chromatography using silicon dioxide gel, eluting with methanol to afford the title compound (107 mg, 75% yield): $^1$H NMR (400 MHz, Chloroform-d) δ 7.45-6.96 (m, 3H), 6.96-6.60 (m, 4H), 5.22-4.95 (m, 2H), 4.68-4.32 (m, 3H), 4.24-3.67 (m, 1H), 2.84 (d, 2H), 2.24 (s, 3H), 2.10-1.87 (m, 2H), 1.81-1.50 (m, 4H), 1.34 (d, 6H); LC-MS: 433.3 [M+H]$^+$.

Example 14: [4-(2-methylpropoxy)phenyl]methyl N-[(2,4-difluorophenyl)methyl]-N-(1-methylpiperidin-4-yl)carbamate (14)

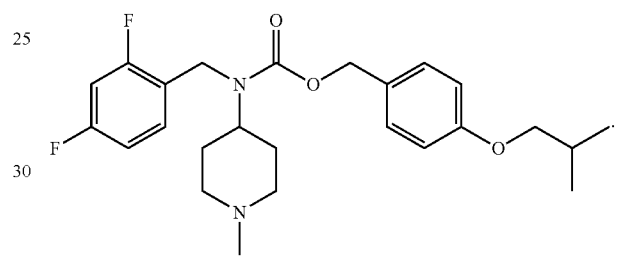

The compound was prepared in analogy with example 13 using [4-(2-methyl-propoxy)phenyl]methanol (0.735 mmol, 135 mg) and 4-nitrophenyl N-[(2,4-difluorophenyl)methyl]-N-(1-methylpiperidin-4-yl)carbamate. The crude material was purified by column chromatography using silicon dioxide gel, eluting with 25% to 50% methanol in ethyl acetate. The solution was filtered to remove silica particles and the filtrate was evaporated to give the title compound (101 mg, 62% yield): $^1$H NMR (400 MHz, Chloroform-d) δ 7.41-6.96 (m, 3H), 6.96-6.60 (m, 4H), 5.22-4.95 (m, 2H), 4.59-4.32 (m, 2H), 4.23-3.77 (m, 1H), 3.71 (d, 2H), 2.86 (d, 2H), 2.25 (s, 3H), 2.17-1.85 (m, 3H), 1.82-1.46 (m, 4H), 1.03 (d, 6H); LC-MS; 447.3 [M+H]$^+$.

Example 15: (4-methoxyphenyl)methyl N-[(2,4-difluorophenyl)methyl]-N-(1-methylpiperidin-4-yl) carbamate (15)

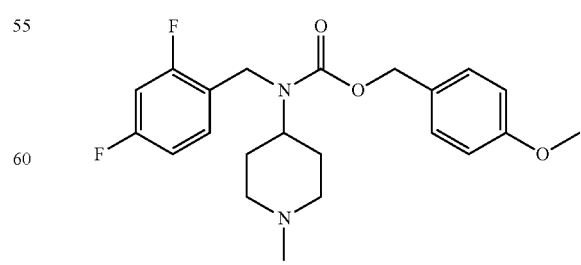

The compound was prepared in analogy with example 13 using 4-nitrophenyl N-[(2,4-difluorophenyl)methyl]-N-(1- methylpiperidin-4-yl)carbamate and (4-methoxyphenyl)-methanol. The crude material was purified by column chromatography using silicon dioxide gel, eluting with 25% to 50% methanol in ethyl acetate to give the title compound (78 mg, 69% yield): $^1$H NMR (400 MHz, Chloroform-d) δ 7.44-6.97 (m, 3H), 6.97-6.63 (m, 4H), 5.23-4.98 (m, 2H), 4.56-4.34 (m, 2H), 4.24-3.73 (m, 1H), 3.81 (s, 3H), 2.86 (d, 2H), 2.25 (s, 3H), 2.02 (m, 2H), 1.83-1.46 (m, 4H); LC-MS: 405.2 [M+H]$^+$.

Example 16: N-[(2,4-difluorophenyl)methyl]-N-(1-methylpiperidin-4-yl){[(4-methoxyphenyl)methyl]sulfanyl}formamide (16)

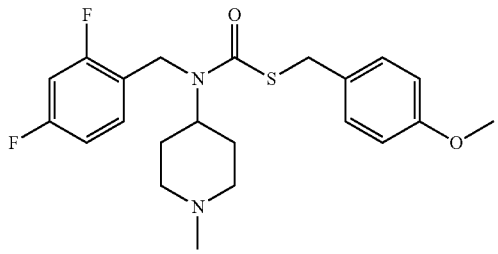 [SMILES: COc1ccc(COC(=O)N(Cc2ccc(F)cc2F)C2CCN(C)CC2)cc1]

4-nitrophenyl N-[(2,4-difluorophenyl)methyl]-N-(1-methylpiperidin-4-yl)carbamate (57.4 mg, 0.142 mmol) was dissolved in dimethylformamide (1 ml) and (4-methoxyphenyl)methanethiol (0.425 mmol, 60 µl) was added. The mixture was stirred at 60° C. for 5 hours, then at 50° C. for 17 hours. The mixture was partitioned between diethyl ether and 0.5 M sodium hydroxide, the organic phase was collected, dried, and evaporated. The residue was purified by column chromatography using silicon dioxide gel, eluting with 0% to 30% methanol in ethyl acetate to afford the title compound (36 mg, 61% yield): $^1$H NMR (400 MHz, Chloroform-d) δ 7.28 (d, 2H), 7.19 (q, 1H), 6.84 (d, 2H), 6.84-6.72 (m, 2H), 4.60-3.60 (m, 1H), 4.59 (s, 2H), 4.16 (s, 2H), 3.80 (s, 3H), 2.87 (d, 2H), 2.25 (s, 3H), 2.10-1.90 (m, 2H), 1.81-1.57 (m, 4H); LC-MS: 421.2 [M+H]$^+$.

Example 17: 2,2,2-trifluoro-1-[4-(propan-2-yloxy)phenyl]ethyl N-[(4-fluorophenyl)methyl]-N-(1-methylpiperidin-4-yl)carbamate (17)

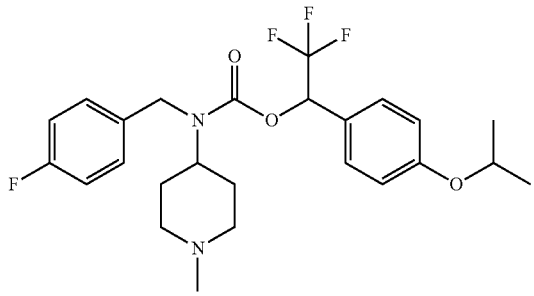 [SMILES: CC(C)Oc1ccc(C(OC(=O)N(Cc2ccc(F)cc2)C2CCN(C)CC2)C(F)(F)F)cc1]

4-isopropoxybenzaldehyde (285 mg, 1.67 mmol, 271.5 µl) was dissolved in dimethylformamide (3.0 ml), potassium carbonate (20 mg, catalytic amount) was added followed by trimethyl(trifluoromethyl)silane (2 M solution in tetrahydrofuran, 2.0 mmol, 1.0 ml). The mixture was stirred 2 hours, then aqueous hydrochloric acid (1 M, 1.0 ml) was added and the mixture was stirred for 20 hours. The mixture was partitioned between diethyl ether and water, the organic phase was dried, evaporated and the residue was purified by column chromatography using silicon dioxide gel, eluting with 20% ethyl acetate in petroleum ether to afford 2,2,2-trifluoro-1-[4-(propan-2-yloxy)phenyl]ethan-1-ol (376 mg, 96% yield). This compound (109 mg, 0.44 mmol) was dissolved in tetrahydrofuran (1.0 ml) and sodium hydride (0.51 mmol, 21 mg) was added. The resulting heterogenous mixture was added to a solution of 4-nitrophenyl N-[(4-fluorophenyl)methyl]-N-(1-methylpiperidin-4-yl)carbamate (137 mg, 0.336 mmol) in tetrahydrofuran (1.0 ml) and the mixture was stirred for 17 hours at 60° C. It was then partitioned between diethyl ether and 0.5 M sodium hydroxide. The organic phase was separated, dried, concentrated, and the residue was purified by column chromatography using silicon dioxide gel, eluting with 0% to 30% methanol in ethyl acetate to afford the title compound (106 mg, 65% yield): $^1$H NMR (400 MHz, Chloroform-d) δ 7.47-7.06 (m, 4H), 7.05-6.69 (m, 4H), 6.22-5.98 (m, 1H), 4.69-4.34 (m, 3H), 4.18-3.86 (m, 1H), 2.98-2.78 (m, 2H), 2.27 (s, 3H), 2.13-1.94 (m, 2H), 1.86-1.50 (m, 4H), 1.34 (d, 6H); LC-MS: 483.3 [M+H]$^+$.

Example 18: [4-(propan-2-yloxy)phenyl]methyl N-[(7S,8aS)-octahydroindolizin-7-yl]-N-[(4-fluorophenyl)methyl]carbamate (18)

4-nitrophenyl [4-(propan-2-yloxy)phenyl]methylcarbonate

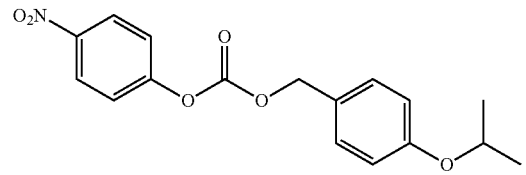 [SMILES: CC(C)Oc1ccc(COC(=O)Oc2ccc([N+](=O)[O-])cc2)cc1]

Ethyl 4-hydroxybenzoate (5.0 g, 30 mmol), potassium carbonate (12.5 g, 90 mmol), and 2-iodopropane (7.45 ml, 75 mmol) were stirred in dimethylformamide (20 mL) at 65° C. for 31 h. More 2-iodopropane (3 ml) was added and stirring at 65° C. was continued for another 21 h. The mixture was partitioned between water and diethyl ether. The organic phase was washed two times with water and one time with brine. The organic phase was dried and evaporated to give ethyl 4-isopropoxybenzoate (6.13 g). This material (5.63 g, 27 mmol) was dissolved in tetrahydrofuran (15 ml) and added slowly to a mixture of lithium aluminum hydride (1.54 g, 40.5 mmol) in tetrahydrofuran (50 ml). After 20 hours, the reaction was quenched with ethyl acetate (7 ml, 70 mmol). Silicon dioxide (15.4 g) was added and the mixture was stirred for 30 min. The resulting suspension was filtered and the filtrate was evaporated and give a residue that was partitioned between diethyl ether and sodium hydroxide (aqueous, 1M). The organic phase was separated, dried and evaporated to give 4-isopropoxybenzyl alcohol (3.46 g). The alcohol (6 mmol, 1.0 g) was dissolved in dichloromethane (10 mL) and p-nitrophenyl chloroformate (1.25 g, 6 mmol) was added. Pyridine (510 µl, 6 mmol) dissolved in dichloromethane (5 ml) was added dropwise. After 1 hour, the mixture was concentrated. The crude material was purified by column chromatography using silicon dioxide gel, eluting with 20% ethyl acetate in petroleum ether to afford the desired carbonate (1.56 g).

[4-(propan-2-yloxy)phenyl]methyl N-[(7S,8aS)-octahydroindolizin-7-yl]-N-[(4-fluorophenyl)methyl] carbamate (18)

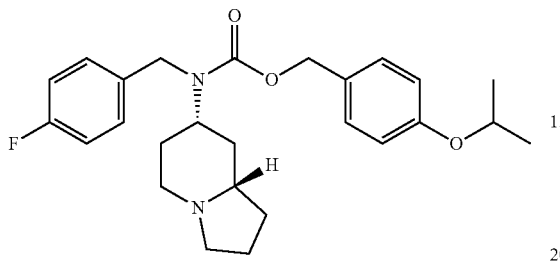

4-Nitrophenyl [4-(propan-2-yloxy)phenyl]methylcarbonate (60 mg, 0.18 mmol) was added to (7S,8aS)-N-[(4-fluorophenyl)methyl]-octahydroindolizin-7-amine (30 mg, 0.12 mmol) in pyridine (1.0 ml). The mixture was stirred at 55° C. for 20 h and then cooled to ambient temperature and concentrated. The crude was partitioned between diethyl ether and sodium hydroxide (aqueous, 1M). The organic phase was evaporated. The crude material was purified by column chromatography using silicon dioxide gel, eluting with 0-10% methanol in ethyl acetate. Fractions containing product were pooled, concentrated and further purified by column chromatography using silicon dioxide gel, eluting with 25% methanol in ethyl acetate to afford the title compound (10 mg); $^1$H NMR (400 MHz, Chloroform-d) δ 7.42-7.01 (m, 4H), 7.00-6.67 (m, 4H), 5.21-4.95 (m, 2H), 4.63-3.84 (m, 4H), 3.06 (d, 1H), 3.00 (t, 1H), 2.17-1.97 (m, 2H), 1.97-1.21 (m, 9H), 1.33 (d, 6H); LC-MS: 441.4 [M+H]$^+$.

Example 19: N-[(2,4-difluorophenyl)methyl]-N-(1-methylpiperidin-4-yl)-2-[4-(propan-2-yloxy)phenyl] acetamide; trifluoroacetic acid (19)

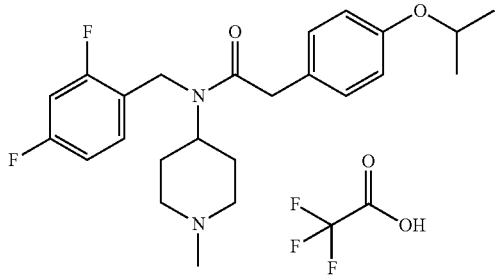

N-[(2,4-difluorophenyl)methyl]-1-methylpiperidin-4-amine (1 equivalent) was dissolved in dichloromethane. Pyridine (3 equivalents) was added followed by and 2-[4-(propan-2-yloxy)phenyl]acetyl chloride (1.2 equivalents) dissolved in dichloromethane. The mixture was stirred for 20 hours and then partitioned between dichloromethane and sodium hydroxide (aqueous, 0.5 M). The organic phase was dried and evaporated. The residue was purified by column chromatography using silicon dioxide gel. The crude material was purified by HPLC, eluting with 38 to 72% acetonitrile in water (containing 0.1% trifluoroacetic acid). Yield: 65%. $^1$H NMR (400 MHz, Chloroform-d) δ 11.90 (bs, 1H), 7.06 (dd 3H), 6.85 (dt, 4H), 4.85-4.72 (m, 1H), 4.56-4.47 (m, 3H), 3.5-3.50 (m, 4H), 2.86-2.73 (m, 5H), 2.06 (d, 2H), 1.87-1.79 (m, 2H), 1.35-1.30 (m, 6H); LC-MS: 417.2 [M+H]$^+$.

Example 20: 2-[2-fluoro-4-(2-methylpropoxy)phenyl]-N-[(4-fluorophenyl)methyl]-N-(1-methylpiperidin-4-yl)acetamide; trifluoroacetic acid (20)

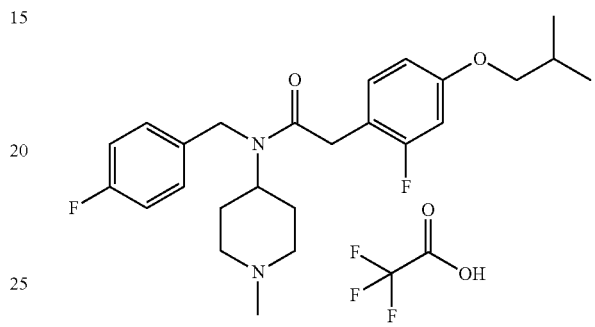

The compound was prepared in analogy with example 19 using N-[(4-fluorophenyl)methyl]-1-methylpiperidin-4-amine and 2-[2-fluoro-4-(2-methylpropoxy)-phenyl]acetyl chloride. The compound was purified by HPLC, eluting with 25 to 45% acetonitrile in water (containing 0.1% trifluoroacetic acid). Yield: 59%. $^1$H NMR (400 MHz, Chloroform-d) δ 12.73 (bs, 1H), 7.33-7.22 (m, 2H), 7.21-6.95 (m, 3H), 6.71 (d, 1H), 6.66 (d, 1H), 4.88 (t, 1H), 4.66 (s, 2H), 3.75 (d, 2H), 3.65 (s, 2H), 3.55 (d, 2H), 2.88 (t, 2H), 2.76 (s, 3H), 2.39-2.05 (m, 3H), 1.85 (d, 2H), 1.08 (d, 6H); LC-MS: 431.3 [M+H]$^+$.

Example 21: 2-[3-fluoro-4-(2-methylpropoxy)phenyl]-N-[(4-fluorophenyl)methyl]-N-(1-methylpiperidin-4-yl)acetamide; trifluoroacetic acid (21)

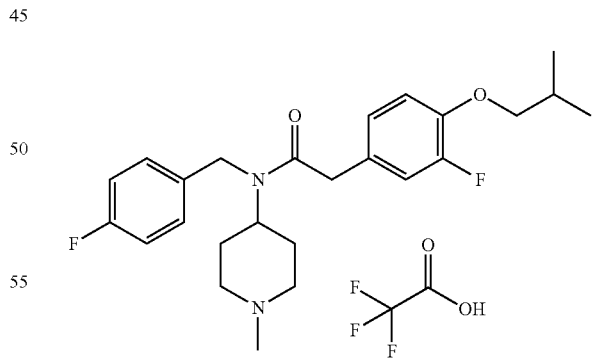

The compound was prepared in analogy with example 19 using N-[(4-fluorophenyl)methyl]-1-methylpiperidin-4-amine and 2-[3-fluoro-4-(2-methylpropoxy)phenyl]acetyl chloride. The compound was purified by HPLC, eluting with 25 to 45% acetonitrile in water (containing 0.1% trifluoroacetic acid). Yield: 47%. $^1$H NMR (400 MHz, Chloroform-d) δ 12.68 (bs, 1H), 7.18-7.10 (m, 2H), 7.05 (t, 2H), 6.93-6.82 (m, 2H), 6.77 (d, 1H), 4.81 (t, 1H), 4.51 (s, 2H), 3.75 (d, 2H), 3.55 (s, 2H), 3.50 (d, 2H), 2.79 (t, 2H), 2.72 (s, 3H), 2.22-2.02 (m, 3H), 1.76 (d, 2H), 1.02 (d, 6H); LC-MS: 431.3 [M+H]⁺.

Example 22: N-(2,4-difluorobenzyl)-2-(4-isobutoxyphenyl)-N-(1-methylpiperidin-4-yl)acetamide; trifluoroacetic acid (22)

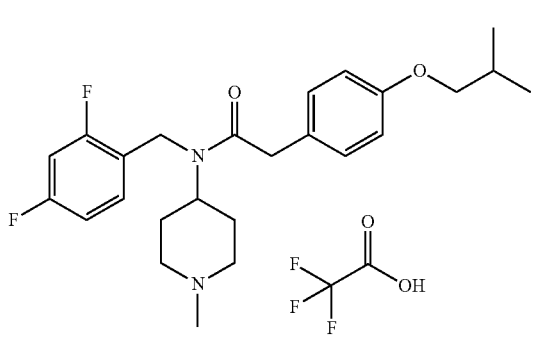

The compound was prepared in analogy to example 19 (N-[(2,4-difluorophenyl)methyl]-N-(1-methylpiperidin-4-yl)-2-[4-(propan-2-yloxy)phenyl]acetamide) using N-[(2,4-difluorophenyl)methyl]-1-methylpiperidin-4-amine and 2-[4-(2-methylpropoxy)phenyl]acetyl chloride. Yield: 42% ¹H NMR (400 MHz, Methanol-d) δ ¹H NMR (400 MHz, Chloroform-d) δ 12.62 (bs, 1H), 7.23-6.96 (m, 3H), 6.93-6.73 (m, 4H), 4.82 (t, 1H), 4.52 (s, 2H), 3.70 (d, 2H), 3.64-3.47 (m, 4H), 2.87-2.68 (m, 5H), 2.19-1.99 (m, 3H), 1.82 (d, 2H), 1.02 (d, 6H); LC-MS: 431.3 [M+H]⁺.

Example 23: N-(2,4-difluorobenzyl)-2-(4-ethoxyphenyl)-N-(1-methylpiperidin-4-yl)acetamide; trifluoroacetic acid (23)

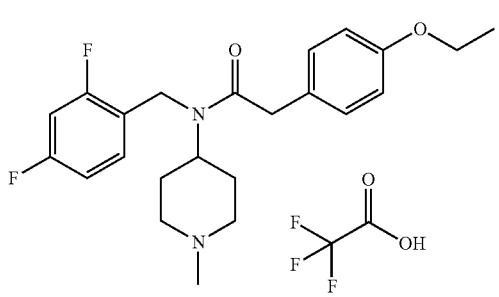

To N-[(2,4-difluorophenyl)methyl]-1-methylpiperidin-4-amine (200 mg, 0.832 mmol) in diethyl ether (2.0 ml) was added a solution of 2-(4-ethoxyphenyl)acetyl chloride (250 mg, 1.25 mmol) dissolved in diethyl ether (2.0 ml) and the resulting mixture was stirred at room temperature for 2 hours. The mixture was then partitioned between diethyl ether and sodium hydrogen carbonate (aqueous, saturated). The organic phase was collected, dried and the crude was purified by column chromatography using silicon dioxide gel, eluting with 0-66% methanol in ethyl acetate to afford the title compound as the free base (0.49 mmol, 199 mg, 59% yield). This was dissolved in dichloromethane (2.0 ml) and trifluoroacetic acid (0.51 mmol, 39 µl) was added. The volatiles were removed to afford the title compound (253 mg, 100% yield): ¹H NMR (400 MHz, Chloroform-d) δ 11.58 (s, 1H), 7.23-6.99 (m, 3H), 6.96-6.72 (m, 4H), 4.81 (m, 1H), 4.53 (s, 2H), 4.02 (q, 2H), 3.67-3.52 (m, 4H), 2.93-2.71 (m, 5H), 2.08 (q, 2H), 1.84 (d, 2H), 1.41 (t, 3H); LC-MS: 403.3 [M+H]⁺.

Example 24: N-(2,4-difluorobenzyl)-2-(4-butoxyphenyl)-N-(1-methylpiperidin-4-yl)acetamide trifluoroacetic acid (24)

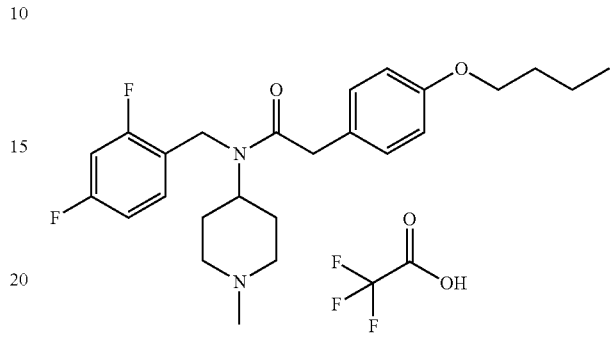

Prepared in analogy with example 23 (N-(2,4-difluorobenzyl)-2-(4-ethoxyphenyl)-N-(1-methylpiperidin-4-yl)acetamide) using N-[(2,4-difluorophenyl)methyl]-1-methylpiperidin-4-amine (200 mg, 0.832 mmol) and 2-(4-butoxyphenyl)acetyl chloride (283 mg, 1.25 mmol). Yield: 147 mg, 41%: ¹H NMR (400 MHz, Chloroform-d) δ 12.24 (s, 1H), 7.20-6.99 (m, 3H), 6.94-6.76 (m, 4H), 4.85 (m, 1H), 4.54 (s, 2H), 3.94 (t, 2H), 3.64-3.50 (m, 4H), 2.87-2.68 (m, 5H), 2.18 (q, 2H), 1.90-1.69 (m, 4H), 1.50 (h, 2H), 0.98 (t, 3H); LC-MS: 431.3 [M+H]⁺.

Example 25: 4-ethoxybenzyl (2,4-difluorobenzyl)(1-methylpiperidin-4-yl)carbamate (25)

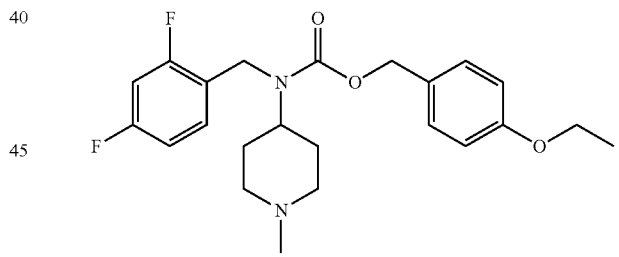

(4-Ethoxyphenyl)methanol (0.65 mmol, 101 mg) was dissolved in tetrahydrofuran (2.0 ml) and sodium hydride (0.975 mmol, 60%, 39 mg) was added in one portion. After gas evolution ceased the suspension was added to a solution of 4-nitrophenyl N-[(2,4-difluorophenyl)methyl]-N-(1-methylpiperidin-4-yl)carbamate (185 mg, 0.434 mmol) dissolved in tetrahydrofuran (2.0 ml). The mixture was stirred for 4 hours. The mixture was partitioned between diethyl ether and sodium hydroxide (0.2 M). The organic phase was collected, dried and the crude was purified by column chromatography using silicon dioxide gel, eluting with 10-25% methanol in ethyl acetate. Fractions containing product were collected, evaporated and stirred in diethyl ether (5.0 ml) for 20 min to precipitate silica. The solution was filtered and evaporated to afford the title compound (97 mg, yield 53%): ¹H NMR (400 MHz, Chloroform-d) δ 7.42-6.97 (m, 3H), 6.97-6.63 (m, 4H), 5.22-4.96 (m, 2H), 4.57-4.33 (m, 2H), 4.23-3.72 (m, 1H), 4.03 (q, 2H), 2.85 (d, 2H), 2.25 (s, 3H), 2.13-1.86 (m, 2H), 1.83-1.50 (m, 4H), 1.42 (t, 3H); LC-MS: 419.3 [M+H]+.

Example 26: 4-(allyloxy)benzyl (2,4-difluorobenzyl)(1-methylpiperidin-4-yl)carbamate (26)

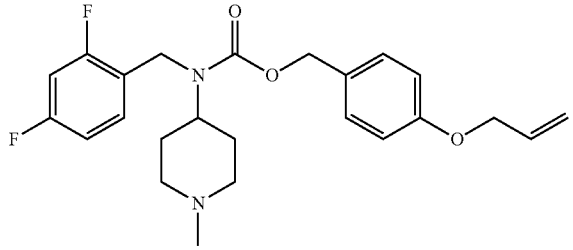

Prepared in analogy with example 25 using 4-nitrophenyl N-[(2,4-difluorophenyl)methyl]-N-(1-methylpiperidin-4-yl)carbamate (359 mg) and [4-(prop-2-en-1-yloxy)phenyl]methanol (304 mg). Yield: 221 mg, 58%; ¹H NMR (400 MHz, Chloroform-d) δ 7.46-6.98 (m, 3H), 6.98-6.65 (m, 4H), 6.06 (m, 1H), 5.42 (d, 1H), 5.30 (d, 1H), 5.23-4.97 (m, 2H), 4.54 (d, 2H), 4.54-4.36 (m, 2H), 4.24-3.71 (m, 1H), 2.86 (d, 2H), 2.26 (s, 3H), 2.14-1.87 (m, 2H), 1.84-1.50 (m, 4H); LC-MS: 431.3 [M+H]+.

Example 27: 4-(3-fluoropropoxy)benzyl (2,4-difluorobenzyl)(1-methylpiperidin-4-yl)carbamate; trifluoroacetic acid (27)

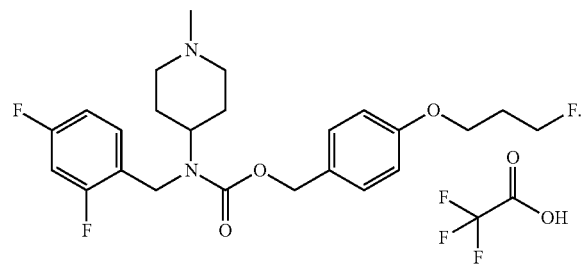

4-(3-fluoropropoxy)benzonitrile

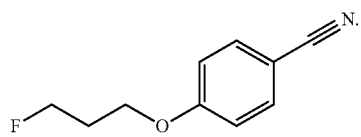 [SMILES: N#Cc1ccc(OCCCF)cc1]

1-bromo-3-fluoropropane (275 mg, 1.95 mmol) was added to 4-hydroxybenzonitrile (202 mg, 1.70 mmol) dissolved in dimethylformamide (2 ml). After 18 hours of stirring at room temperature the reaction mixture was added to ethyl acetate (10 ml). The solution was washed with sodium hydroxide (3×10 ml, 1 M aqueous), the organic phase was separated, dried using a phase separator and concentrated to afford the desired crude intermediate as oil (303 mg).

1-[4-(3-fluoropropoxy)phenyl]methanamine

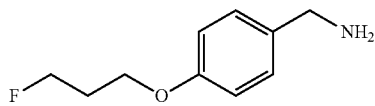 [SMILES: NCc1ccc(OCCCF)cc1]

Borane (5 ml, 1 M in tetrahydrofuran, 5 mmol) was added to 4-(3-fluoropropoxy)-benzonitrile (303 mg). After 3.5 hours of stirring at room temperature additional borane (2 ml, 1 M in tetrahydrofuran, 2 mmol) was added and the mixture heated to 50° C. After 17 hours of stirring the mixture was concentrated. The residue was re-dissolved in dichloro-methane (5 ml), washed with sodium hydroxide (5 ml, 1 M aqueous) and filtered. The organic phase was dried using a phase separator and concentrated to afford the desired crude intermediate as oil (540 mg).

[4-(3-fluoropropoxy)phenyl]methanol

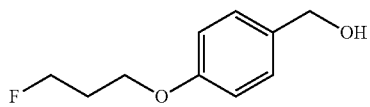 [SMILES: OCc1ccc(OCCCF)cc1]

Sodium nitrite (226 mg, 3.27 mmol) was added in small portion to [4-(3-fluoropropoxy)phenyl]methanamine (133 mg) dissolved in a mixture of water (500 µl), acetic acid (500 µl) and hydrochloric acid (5 µl) at 0° C. giving rapid gas evolution. After 150 minutes of stirring while reaching room temperature ethyl acetate (2 ml) was added to the mixture. The organic phase was separated, washed with sodium hydrogen carbonate (1 ml, saturated aqueous), brine (1 ml), dried using a phase separator and concentrated to afford the desired crude intermediate as oil (37.9 mg).

[4-(3-fluoropropoxy)phenyl]methyl N-[(2,4-difluorophenyl)methyl]-N-(1-methylpiperidin-4-yl)carbamate; trifluoroacetic acid Sodium hydride (42 mg, 60% in mineral oil, 1.75 mmol) was added to crude [4-(3-fluoropropoxy)phenyl]methanol (37.5 mg) dissolved in tetrahydrofuran (600 µl). After 10 minutes of stirring at room temperature 4-nitrophenyl N-[(2,4-difluorophenyl)methyl]-N-(1-methylpiperidin-4-yl)carbamate dissolved in tetrahydrofuran (400 µl) was added. After 28 hours of stirring ethyl acetate (2 ml) was added. The mixture was washed with sodium hydroxide (2 ml, 1 M aqueous) and the phases were separated. The aqueous phase was extracted with ethyl acetate (2×1 ml) and the combined organic phases were dried using a phase separator and concentrated to oil. The crude material was purified by HPLC, eluting with 25-40% acetonitrile in water (containing 0.1% trifluoroacetic acid) to afford the title compound (18.0 mg, 8% over 4 steps): ¹H NMR (400 MHz, Chloroform-d) δ 13.09 (bs, 1H), 7.45-6.65 (m, 7H), 5.17-5.00 (m, 2H), 4.70 (t, 1H), 4.58 (t, 1H), 4.53-4.27 (m, 2H), 4.16-4.03 (m, 2H), 3.57 (d, 2H), 3.52-3.24 (m, 1H), 2.86-2.60 (m, 5H), 2.39-2.06 (m, 4H), 1.96-1.60 (m, 2H); LCMS: 451.3 [M+H]+.

Example 28: 4-((1,3-difluoropropan-2-yl)oxy)benzyl (2,4-difluorobenzyl)(1-methylpiperidin-4-yl)carbamate; trifluoroacetic acid (28)

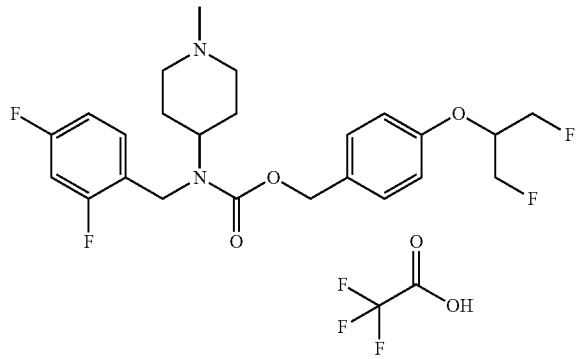

4-[(1,3-difluoropropan-2-yl)oxy]benzonitrile

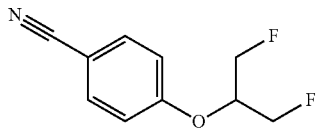 [SMILES: N#Cc1ccc(OC(CF)CF)cc1]

1,3-difluoropropan-2-ol (192 µl, 2.48 mmol) was added to potassium tert-butoxide (280 mg, 2.50 mmol) in dioxane (2 ml). After 10 minutes of stirring at room temperature 4-fluorobenzonitrile (209 mg, 1.73 mmol) in dioxane (2 ml) was added. After another 17 hours, the reaction mixture was diluted with diethyl ether (5 ml) and washed with water (5 ml). The water phase was extracted with diethyl ether (3×5 ml) and the combined organic phase was dried using a phase separator and concentrated to afford the desired crude intermediate as a white solid (190 mg).

{4-[(1,3-difluoropropan-2-yl)oxy]phenyl}methanamine

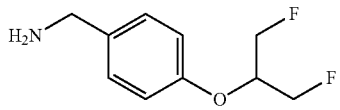 [SMILES: NCc1ccc(OC(CF)CF)cc1]

Borane (2 ml, 1 M in tetrahydrofuran, 2 mmol) was added to 4-[(1,3-difluoropropan-2-yl)oxy]benzonitrile (89.2 mg). After 1 hour of stirring at room temperature the mixture was heated to 50° C. After an additional 1 hour of stirring the mixture was concentrated. The residue was re-dissolved in methanol (2 ml), and heated to reflux for 1 hour. The mixture was then concentrated, sodium hydroxide (1 ml, 1 M aqueous) was added, then extracted with ethyl acetate (2×1 ml). The combined organic phase was dried using a phase separator and concentrated to afford the desired crude intermediate as oil (81.5 mg).

{4-[(1,3-difluoropropan-2-yl)oxy]phenyl}methanol

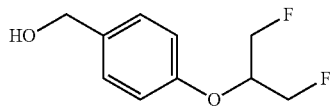 [SMILES: OCc1ccc(OC(CF)CF)cc1]

Sodium nitrite (223 mg, 3.23 mmol) was added in small portions to {4-[(1,3-difluoropropan-2-yl)oxy]phenyl}methanamine (51.2 mg) dissolved in a mixture of water (500 µl), acetic acid (500 µl) and hydrochloric acid (5 µl) at 0° C. giving rapid gas evolution. After 150 minutes of stirring while reaching room temperature ethyl acetate (2 ml) was added to the mixture. The organic phase was separated, washed with sodium hydrogen carbonate (1 ml, saturated aqueous), brine (1 ml), dried using a phase separator and concentrated to afford the desired crude intermediate as oil (18.0 mg).

{4-[(1,3-difluoropropan-2-yl)oxy]phenyl}methyl N-[(2,4-difluorophenyl)methyl]-N-(1-methylpiperidin-4-yl)carbamate; trifluoroacetic acid Sodium hydride (14.8 mg, 60% in mineral oil, 0.370 mmol) was added to crude {4-[(1,3-difluoropropan-2-yl)oxy]phenyl}methanol (18.0 mg) dissolved in tetrahydrofuran (600 µl). After 40 minutes of stirring at room temperature 4-nitrophenyl N-[(2,4-difluorophenyl)methyl]-N-(1-methylpiperidin-4-yl)carbamate dissolved in tetrahydrofuran (400 µl) was added. After 5.5 hours of stirring ethyl acetate (2 ml) was added. The mixture was washed with sodium hydroxide (2 ml, 1 M aqueous) and the phases were separated. The aqueous phase was extracted with diethyl ether (2×1 ml) and the combined organic phases were dried using a phase separator and concentrated to an oil. The crude material was purified by HPLC, eluting with 20-40% acetonitrile in water (containing 0.1% trifluoroacetic acid) to afford the title compound (9.4 mg, 3% over 4 steps): $^1$H NMR (400 MHz, Chloroform-d) δ 12.94 (bs, 1H), 7.27 (m, 2H), 7.03-6.88 (m, 3H), 6.88-6.69 (m, 2H), 5.10 (d, 2H), 4.84-4.58 (m, 6H), 4.48 (m, 2H), 3.59 (d, 2H), 2.76 (m, 5H), 2.23 (m, 2H), 1.82 (m, 2H); LCMS: 469.3 [M+H]$^+$.

Example 29: 4-(2-hydroxy-2-methylpropoxy)benzyl (2,4-difluorobenzyl)(1-methylpiperidin-4-yl)carbamate (29)

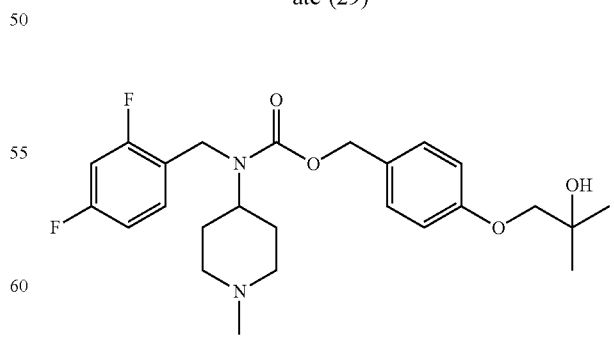

Prepared in analogy with example 26 (4-(allyloxy)benzyl (2,4-difluorobenzyl)(1-methylpiperidin-4-yl)carbamate) using N-[(2,4-difluorophenyl)methyl]-N-(1-methylpiperidin-4-yl)carbamate (130 mg) and 1-[4-(hydroxymethyl)phenoxy]-2-methylpropan-2-ol (94.4 mg). The crude material was purified by HPLC, eluting with acetonitrile in water (containing 2% acetic acid). Yield: 36 mg, 24%; $^1$H NMR (400 MHz, Chloroform-d) δ 7.39-6.96 (m, 3H), 6.96-6.65 (m, 4H), 5.09 (bs, 2H), 4.54-4.24 (m, 3H), 3.80 (s, 2H), 3.58 (d, 2H), 2.86-2.50 (m, 2H), 2.74 (s, 3H), 2.39-2.04 (m, 2H), 1.89-1.65 (m, 2H), 1.36 (s, 6H); LC-MS: 463.3 [M+H]$^+$.

Example 30: 4-cyclopropoxybenzyl (2,4-difluorobenzyl)(1-methylpiperidin-4-yl)carbamate (30)

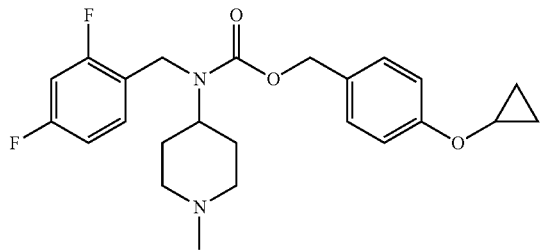 [SMILES: CN1CCC(N(Cc2ccc(F)cc2F)C(=O)OCc2ccc(OC3CC3)cc2)CC1]

Prepared in analogy with example 26 (4-(allyloxy)benzyl (2,4-difluorobenzyl)(1-methylpiperidin-4-yl)carbamate) using 4-nitrophenyl N-[(2,4-difluorophenyl)methyl]-N-(1-methylpiperidin-4-yl)carbamate (275 mg) and 4-cyclopropoxyphenyl)methanol (106 mg). Yield: 195 mg, 70% yield; $^1$H NMR (400 MHz, DMSO-d$_6$) δ 7.45-7.09 (m, 4H), 6.99 (bs, 3H), 5.02 (bs, 2H), 4.40 (s, 2H), 3.88-3.65 (m, 2H), 2.73 (d, 2H), 2.09 (s, 3H), 1.83 (t, 2H), 1.63 (q, 2H), 1.49 (d, 2H), 0.77 (m, 2H), 0.63 (m, 2H); LC-MS: 431.3 [M+H]$^+$.

Example 31: N-[(4-chloro-2-fluorophenyl)methyl]-N-(1-methylpiperidin-4-yl)-2-[4-(2-methylpropoxy)phenyl]acetamide; trifluoroacetic acid (31)

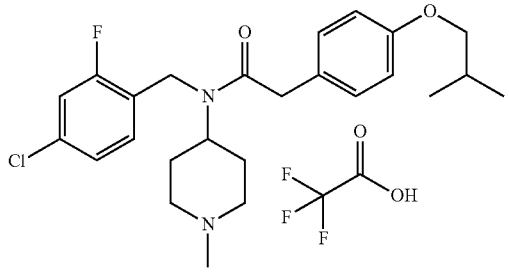

N-[(4-chloro-2-fluorophenyl)methyl]-1-methylpiperidin-4-amine

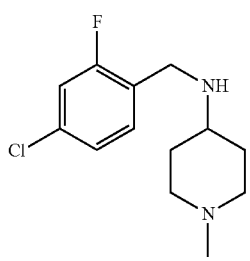 [SMILES: CN1CCC(NCc2ccc(Cl)cc2F)CC1]

1-methylpiperidin-4-one (213 mg, 1.88 mmol) and (4-chloro-2-fluorophenyl)-methanamine (300 mg, 1.88 mmol) were dissolved in ethanol (7.5 ml). The reaction was stirred for 10 minutes. Sodium triacetoxyborohydride (597 mg, 2.82 mmol) was added. The reaction was stirred at room temperature overnight. The mixture was concentrated. The residue was dissolved in dichloromethane and Na$_2$CO$_3$ (sat, in water). The phases were separated. The water phase was extracted two more times with dichloromethane. The combined organic phases were dried over sodium sulfate. The organic phase was concentrated and the crude material was used without further purification in the next step.

To a solution of N-[(4-chloro-2-fluorophenyl)methyl]-1-methylpiperidin-4-amine (35.0 mg, 0.14 mmol) and triethylamine (38 μl, 0.27 mmol) in dichloromethane (0.60 ml) was added drop-wise a solution of 2-[4-(2-methylpropoxy)phenyl]acetyl chloride (32.4 mg, 0.14 mmol) in dichloromethane (0.55 ml). The reaction was stirred at room-temperature overnight. The organic phase was concentrated and the crude material was purified by HPLC, eluting with 35-65% acetonitrile in water (containing 0.1% trifluoroacetic acid) to afford the title compound (35 mg, 46%): $^1$H NMR (400 MHz, Chloroform-d) δ 13.08 (s, 1H), 7.20-7.09 (m, 3H), 7.04 (d, 2H), 6.82 (d, 2H), 4.83 (t, 1H), 4.52 (s, 2H), 3.70 (d, 2H), 3.56 (s, 2H), 3.54-3.45 (m, 2H), 2.80 (d, 2H), 2.74 (s, 3H), 2.17-2.02 (m, 3H), 1.81 (d, 2H), 1.02 (d, 6H); LCMS: 447.3 [M+H]$^+$.

Example 32: N-[(4,5-difluoro-2-methoxyphenyl)methyl]-N-(1-methylpiperidin-4-yl)-2-[4-(propan-2-yloxy)phenyl]acetamide; trifluoroacetic acid (32)

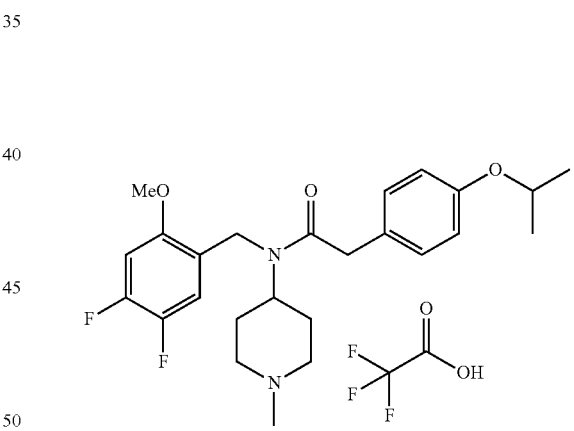

The compound was prepared in analogy with example 31 (N-[(4-chloro-2-fluorophenyl)methyl]-N-(1-methylpiperidin-4-yl)-2-[4-(2-methylpropoxy)phenyl]acetamide; trifluoroacetic acid) using (4,5-difluoro-2-methoxyphenyl)methanamine and 2-[4-(propan-2-yloxy)phenyl]acetyl chloride. The crude material was purified by HPLC, eluting with 35-65% acetonitrile in water (containing 0.1% trifluoroacetic acid) to afford the title compound (40 mg, 55%): $^1$H NMR (400 MHz, Chloroform-d) δ 12.78 (s, 1H), 7.03 (d, 2H), 6.92-6.77 (m, 3H), 6.73 (dd, 1H), 4.84 (t, 1H), 4.50 (dt, 1H), 4.42 (s, 2H); 3.82 (s, 3H), 3.55-3.50 (m, 4H), 2.86-2.75 (m, 2H), 2.73 (s, 3H), 2.04 (q, 2H), 1.80 (d, 2H), 1.32 (d, 6H); LCMS: 447.3 [M+H]$^+$ Example 33: N-[(2,6-difluoro-4-methoxyphenyl)
methyl]-N-(1-methylpiperidin-4-yl)-2-[4-(2-methyl-
propoxy)phenyl]acetamide; trifluoroacetic acid (33)

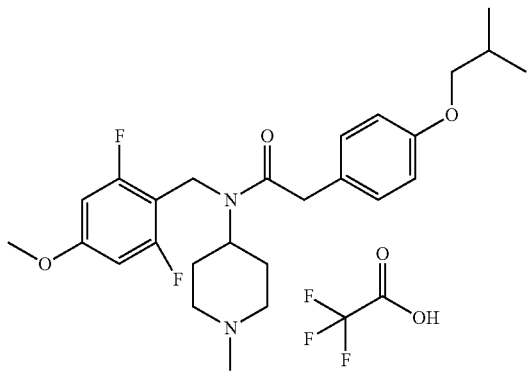

The compound was prepared in analogy with example 31 (N-[(4-chloro-2-fluoro-phenyl)methyl]-N-(1-methylpiperidin-4-yl)-2-[4-(2-methylpropoxy)phenyl]acetamide; trifluoroacetic acid) using (2,6-difluoro-4-methoxyphenyl)methanamine and 2-[4-(2-methyl-propoxy)phenyl]acetyl chloride. The crude material was purified by HPLC, eluting with 35-60% acetonitrile in water (containing 0.1% trifluoroacetic acid) to afford the title compound (29 mg, 39%): $^1$H NMR (400 MHz, Chloroform-d) δ 12.36 (s, 1H), 7.13 (d, 2H), 6.87 (d, 2H), 6.48 (d, 2H), 4.67-4.43 (m, 3H), 3.84 (s, 2H), 3.80 (s, 3H), 3.71 (d, 2H), 3.57 (d, 2H), 3.29-3.09 (m, 1H), 2.81-2.65 (m, 4H), 2.13-1.92 (m, 3H), 1.83 (d, 2H), 1.02 (d, 6H); LCMS: 461.3 [M+H]$^+$.

Example 34: N-(1-methylpiperidin-4-yl)-2-[4-(pro-
pan-2-yloxy)phenyl]-N-[(2,3,4-trifluorophenyl)
methyl]acetamide; trifluoroacetic acid (34)

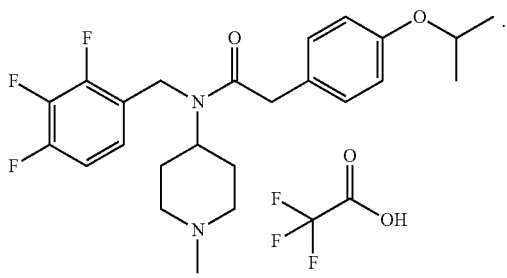

The compound was prepared in analogy with example 31 (N-[(4-chloro-2-fluoro-phenyl)methyl]-N-(1-methylpiperidin-4-yl)-2-[4-(2-methylpropoxy)phenyl]acetamide; trifluoroacetic acid) using (2,3,4-trifluorophenyl)methanamine and 2-[4-(propan-2-yloxy)-phenyl]acetyl chloride. The crude material was purified by HPLC, eluting with 35-65% acetonitrile in water (containing 0.1% trifluoroacetic acid) to afford the title compound (45 mg, 60%): $^1$H NMR (400 MHz, Chloroform-d) δ 12.38 (s, 1H), 7.03 (d, 2H), 6.96 (q, 1H), 6.90-6.78 (m, 3H), 4.81 (t, 1H), 4.61-4.45 (m, 3H), 3.62-3.49 (m, 4H), 2.91-2.79 (m, 2H), 2.76 (s, 3H), 2.10 (q, 2H), 1.83 (d, 2H), 1.33 (d, 6H); LCMS: 435.3 [M+H]$^+$.

Example 35: [4-(2-methylpropoxy)phenyl]methyl
N-[(4,5-difluoro-2-methoxy-phenyl)methyl]-N-(1-
methylpiperidin-4-yl)carbamate (35)

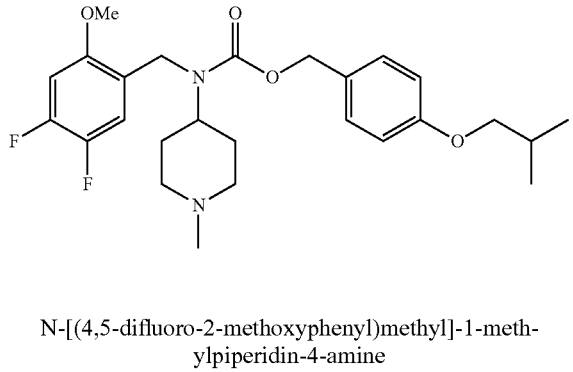

N-[(4,5-difluoro-2-methoxyphenyl)methyl]-1-meth-
ylpiperidin-4-amine

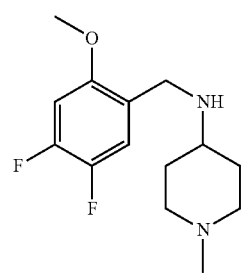 [SMILES: COc1cc(F)c(F)cc1CNC1CCN(C)CC1]

1-methylpiperidin-4-one (198 mg, 1.73 mmol) and (4,5-difluoro-2-methoxyphenyl)methanamine (300 mg, 1.73 mmol) were dissolved in ethanol (7.0 ml). The reaction was stirred for 10 minutes. Sodium triacetoxyborohydride (551 mg, 2.60 mmol) was added. The reaction was stirred at room temperature overnight. The mixture was concentrated. The residue was dissolved in dichloromethane and Na$_2$CO$_3$ (sat, in water). The phases were separated. The water phase was extracted two more times with dichloromethane. The combined organic phases were dried over sodium sulfate. The organic phase was concentrated and the crude material was used without further purification in the next step.

4-nitrophenyl N-[(4,5-difluoro-2-methoxyphenyl)
methyl]-N-(1-methylpiperidin-4-yl)carbamate

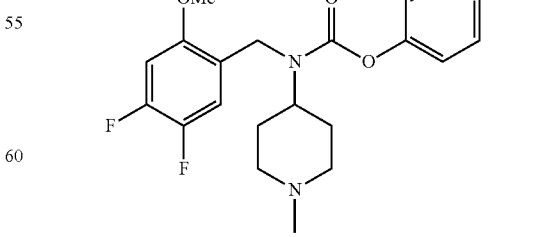

To a solution of N-[(4,5-difluoro-2-methoxyphenyl) methyl]-1-methylpiperidin-4-amine (63 mg, 0.23 mmol) in diethyl ether (0.6 ml) was added a solution of 4-nitrophenyl chloroformate (82.9 mg, 0.35 mmol) in diethyl ether (1.6 ml). The reaction was stirred at room temperature for 30 minutes. The suspension formed was added to a mixture of diethyl ether and saturated sodium bicarbonate. The organic phase was collected. The aqueous phase was extracted two times with diethyl ether. The combined organic phases were dried over sodium sulfate, filtered, and concentrated. The crude material was purified by column chromatography using silicon dioxide gel, eluting with methanol to afford the desired intermediate (49 mg).

To a solution of [4-(2-methylpropoxy)phenyl]methanol (30 mg, 0.17 mmol) in dry tetrahydrofuran (0.5 ml) was added sodium hydride (9.98 mg, 0.25 mmol). The reaction was stirred at room temperature for 30 minutes. 4-nitrophenyl N-[(4,5-difluoro-2-methoxyphenyl)methyl]-N-(1-methylpiperidin-4-yl)carbamate (36.2 mg, 0.083 mmol) dissolved in dry tetrahydrofuran (0.6 ml) was added. The reaction was stirred at room temperature overnight. The reaction was added to a mixture of diethyl ether and sodium hydroxide (0.5 M). The organic phase was collected. The aqueous phase was extracted two times with diethyl ether. The combined organic phases were dried over sodium sulfate, filtered, and concentrated. The crude material was purified by HPLC, eluting with 35-60% acetonitrile in water (containing 2% acetic acid) to afford the title compound (20 mg, 51%): $^1$H NMR (400 MHz, Chloroform-d) δ 7.21-7.09 (m, 2H), 6.94-6.73 (m, 3H), 6.64 (dd, 1H), 5.07 (s, 2H), 4.37 (s, 2H), 4.32-4.18 (m, 1H), 3.80 (s, 3H), 3.71 (d, 2H), 3.31-3.12 (m, 2H), 2.63-2.40 (m, 5H), 2.08 (hept, 3H), 1.80-1.63 (m, 2H), 1.02 (d, 6H); LCMS: 477.3 [M+H]$^+$ Example 36: [4-(2-methylpropoxy)phenyl]methyl N-[(2,6-difluoro-4-methoxyphenyl)methyl]-N-(1-methylpiperidin-4-yl)carbamate; acetic acid (36)

Example 37: [4-(2-methylpropoxy)phenyl]methyl N-(1-methylpiperidin-4-yl)-N-[(2,3,4-trifluorophenyl)methyl]carbamate (37)

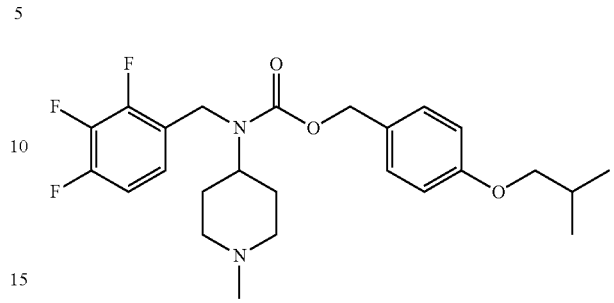

The compound was prepared in analogy with example 35 ([4-(2-methylpropoxy)-phenyl]methyl N-[(4,5-difluoro-2-methoxyphenyl)methyl]-N-(1-methylpiperidin-4-yl)carbamate) using (2,3,4-trifluorophenyl)methanamine. The crude material was purified by HPLC, eluting with 35-65% acetonitrile in water (containing 2% acetic acid) to afford the title compound (14 mg, 20%): $^1$H NMR (400 MHz, Chloroform-d) δ 7.44-7.04 (m, 2H), 7.01-6.66 (m, 4H), 5.08 (s, 2H), 4.57-4.31 (m, 3H), 3.72 (d, 2H), 3.59 (d, 2H), 2.86-2.64 (m, 5H), 2.42-2.16 (m, 2H), 2.08 (h, 1H), 1.95-1.74 (m, 2H), 1.03 (d, 6H); LCMS: 465.3 [M+H]$^+$.

Example 38: [4-(propan-2-yloxy)phenyl]methyl N-[(4-chloro-2-fluorophenyl)-methyl]-N-(1-methylpiperidin-4-yl)carbamate (38)

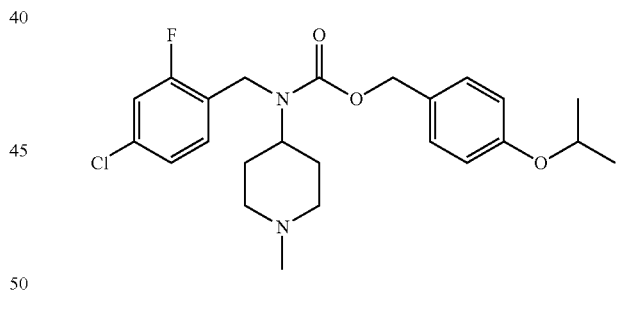

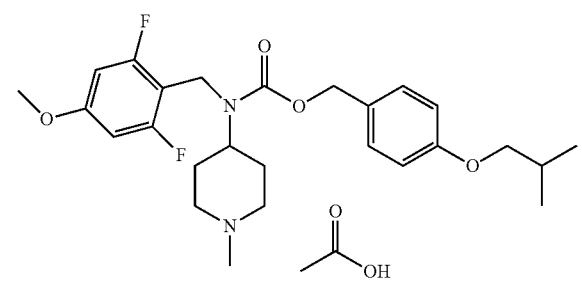

The compound was prepared in analogy with example 35 ([4-(2-methylpropoxy)-phenyl]methyl N-[(4,5-difluoro-2-methoxyphenyl)methyl]-N-(1-methylpiperidin-4-yl)carbamate) using (2,6-difluoro-4-methoxyphenyl)methanamine. The crude material was purified by HPLC, eluting with 35-60% acetonitrile in water (containing 2% acetic acid) to afford the title compound (14 mg, 20%): $^1$H NMR (400 MHz, Chloroform-d) δ 7.23 (d, 2H), 6.85 (d, 2H), 6.38 (d, 2H), 5.06 (s, 2H), 4.48 (s, 2H), 3.90 (s, 1H), 3.77 (s, 3H), 3.71 (d, 2H), 3.26 (d, 2H), 2.60-2.45 (m, 5H), 2.34-2.19 (m, 2H), 2.15-2.04 (m, 1H), 2.03 (s, 3H), 1.75 (s, 2H), 1.02 (d, 6H); LCMS: 477.3 [M+H]$^+$.

The compound was prepared in analogy with example 35 ([4-(2-methylpropoxy)-phenyl]methyl N-[(4,5-difluoro-2-methoxyphenyl)methyl]-N-(1-methylpiperidin-4-yl)carbamate) using (4-chloro-2-fluorophenyl)methanamine and [4-(propan-2-yloxy)phenyl]methanol. The crude material was purified by HPLC, eluting with 35-60% acetonitrile in water (containing 2% acetic acid) to afford the title compound (21 mg, 35%): $^1$H NMR (400 MHz, Chloroform-d) δ 7.25-7.00 (m, 3H), 7.06-6.92 (m, 2H), 6.83 (bs, 2H), 5.06 (bs, 2H), 4.54 (p, 1H), 4.46 (s, 2H), 4.24 (bs, 1H), 3.13 (bs, 2H), 2.59-2.26 (m, 5H), 2.14-1.98 (m, 2H), 1.71 (bs, 2H), 1.34 (d, 6H); LCMS: 449.2 [M+H]$^+$.

Example 39: [4-(2-fluoroethoxy)phenyl]methyl N-[(2,4-difluorophenyl)methyl]-N-(1-methylpiperidin-4-yl)carbamate (39)

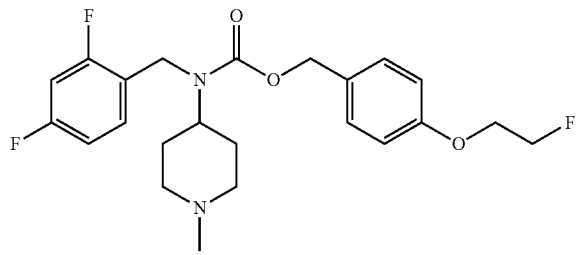 [SMILES: CN1CCC(N(Cc2ccc(F)cc2F)C(=O)OCc2ccc(OCCF)cc2)CC1]

[4-(2-fluoroethoxy)phenyl]methanol (0.81 mmol, 140 mg) and NaH (1.1 mmol, 60%, 44 mg) was mixed in a test tube and tetrahydrofuran (1.0 ml) was added slowly. After gas evolution ceased the suspension was added to a solution of 4-nitrophenyl N-[(2,4-difluorophenyl)methyl]-N-(1-methylpiperidin-4-yl)carbamate (219 mg, 0.54 mmol) dissolved in tetrahydrofuran (2.0 ml) and the mixture was stirred 20 hours, the mixture was partitioned between diethyl ether and 0.5 M NaOH, the organic phase was washed three times with 0.5 M NaOH, then collected, dried, evaporated and the crude was purified by column chromatography using silicon dioxide gel, eluting with 0-40% methanol in ethyl acetate to afford pure fractions. These were collected, evaporated, and dissolved in diethyl ether (4 ml) and let to stand 20 min to precipitate any silica. The mixture was filtered through a pad of $Na_2SO_4$ and the clear solution was evaporated to give the title compound (116 mg, 49% yield). $^1$H NMR (400 MHz, Chloroform-d) δ 7.48-6.98 (m, 3H), 6.98-6.66 (m, 4H), 5.25-4.97 (m, 2H), 4.82 (m, 1H), 4.70 (m, 1H), 4.58-4.36 (m, 2H), 4.35-3.68 (m, 3H), 2.86 (d, 2H), 2.26 (s, 3H), 2.14-1.87 (m, 2H), 1.84-1.48 (m, 4H); LC-MS: 437.3 [M+H]$^+$.

Example 40: (4-butoxyphenyl)methyl N-[(2,4-difluorophenyl)methyl]-N-(1-methylpiperidin-4-yl)carbamate (40)

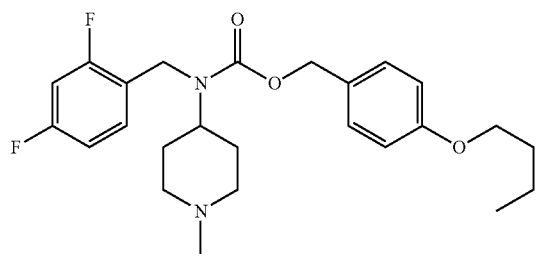 [SMILES: CCCCOc1ccc(COC(=O)N(Cc2ccc(F)cc2F)C2CCN(C)CC2)cc1]

(4-butoxyphenyl)methanol (0.48 mmol, 91.3 mg) was dissolved in tetrahydrofuran (2.0 ml) and NaH (0.96 mmol, 60%, 38.4 mg) was added in one portion. After gas evolution ceased the suspension was added to a solution of 4-nitrophenyl N-[(2,4-difluorophenyl)methyl]-N-(1-methylpiperidin-4-yl)carbamate (130 mg, 0.32 mmol) dissolved in tetrahydrofuran (2.0 ml). The mixture was stirred for 4 hours, the mixture was partitioned between diethyl ether and 0.2 M NaOH, the organic phase was collected, dried, and the crude was purified by column chromatography using silicon dioxide gel, eluting with 10-25% methanol in ethyl acetate to afford the title compound (86 mg, yield 60%): $^1$H NMR (400 MHz, Chloroform-d) δ 7.42-6.97 (m, 3H), 6.97-6.63 (m, 4H), 5.25-4.96 (m, 2H), 4.58-4.33 (m, 2H), 4.23-3.72 (m, 1H), 3.96 (t, 2H), 2.85 (d, 2H), 2.25 (s, 3H), 2.13-1.86 (m, 2H), 1.84-1.41 (m, 8H), 0.98 (t, 3H); LC-MS: 447.3 [M+H]$^+$.

Example 41: [4-(propan-2-yloxy)phenyl]methyl N-[(2-fluoro-4-methoxyphenyl)-methyl]-N-(1-methylpiperidin-4-yl)carbamate (41)

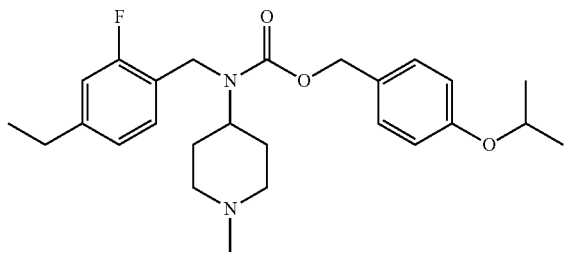 [SMILES: CCc1ccc(CN(C(=O)OCc2ccc(OC(C)C)cc2)C2CCN(C)CC2)c(F)c1]

N-[(2-fluoro-4-methoxyphenyl)methyl]-1-methylpiperidin-4-amine (prepared in analogy with intermediate 7, (N-[(2,4-difluorophenyl)methyl]-1-methylpiperidin-4-amine)) (155 mg, 0.583 mmol) was dissolved in acetonitrile (2.0 ml) and 4-nitrophenyl [4-(2-methylpropoxy)phenyl]methyl carbonate (1.2 equiv., 0.70 mmol, 244 mg) was added. The mixture was stirred at 60° C. for 18 hours, then partitioned between 0.5 M NaOH and diethyl ether, the organic phase was separated, concentrated and the crude was purified by column chromatography using silicon dioxide gel, eluting with 0-30% methanol in ethyl acetate to afford fractions. These fractions were combined and evaporated. To the residue was added diethyl ether and the solution was filtered to remove the solids. The clear solution was evaporated and gave 121 mg impure material. This material was dissolved in diethyl ether and washed several times with aqueous 1 M NaOH, the organic phase was dried, evaporated, and gave the title compound (100 mg, 39% yield): $^1$H NMR (400 MHz, DMSO-d$_6$) δ 7.39-6.99 (m, 3H), 6.97-6.61 (m, 4H), 5.01 (bs, 2H), 4.59 (hept, 1H), 4.37 (bs, 2H), 3.80-3.62 (m, 1H), 3.74 (s, 3H), 2.76-2.64 (m, 2H), 2.08 (s, 3H), 1.81 (m, 2H), 1.62 (m, 2H), 1.45 (m, 2H), 1.25 (d, 6H). LC-MS: 445.3 [M+H]$^+$.

Example 42: methyl 3-(4-{[[(2,4-difluorophenyl)methyl]({[4-(propan-2-yloxy)phenyl]methoxy}carbonyl)amino}piperidin-1-yl)-2,2-dimethylpropanoate (42)

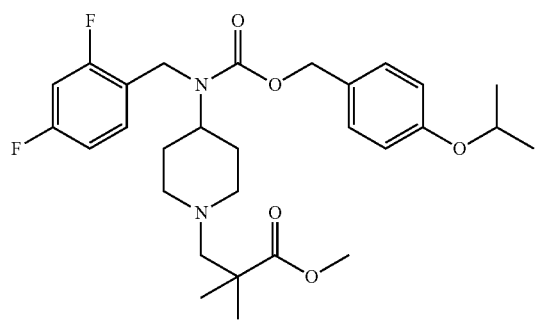 [SMILES: COC(=O)C(C)(C)CN1CCC(N(Cc2ccc(F)cc2F)C(=O)OCc2ccc(OC(C)C)cc2)CC1]

Methyl 3-hydroxy-2,2-dimethylpropanoate (500 mg, 3.7 mmol) was dissolved in dichloromethane (4.0 ml) and Dess-Martin periodinane (4 mmol, 1.79 g) was added. The mixture was stirred 4 hours at room temperature and was then concentrated and filtered through silica eluting with 50% petroleum ether in EtOAc to afford the volatile aldehyde methyl 2,2-dimethyl-3-oxopropanoate (333 mg, 69% yield).

[4-(propan-2-yloxy)phenyl]methyl N-[(2,4-difluorophenyl)methyl]-N-(piperidin-4-yl)carbamate (101 mg, 0.241 mmol) was dissolved in tetrahydrofuran (1.0 ml) and methyl 2,2-dimethyl-3-oxopropanoate (0.484 mmol, 63 mg) dissolved in tetrahydrofuran (1.0 ml) was added followed by sodium triacetoxyborohydride (0.723 mmol, 158 mg). The reaction was stirred for 1 hour and then the mixture was partitioned between diethyl ether and saturated sodium bicarbonate. The organic phase was collected, evaporated, and the crude was purified by column chromatography using silicon dioxide gel, eluting with 15-30% ethyl acetate in petroleum ether to afford the title compound (107 mg, 83% yield): $^1$H NMR (400 MHz, Chloroform-d) δ 7.38-6.96 (m, 3H), 6.95-6.65 (m, 4H), 5.19-4.94 (m, 2H), 4.54 (heptet, 1H), 4.50-4.32 (m, 2H), 4.13-3.69 (m, 1H), 3.64 (s, 3H), 2.76 (d, 2H), 2.44 (s, 2H), 2.33-2.10 (m, 2H), 1.74-1.41 (m, 4H), 1.34 (d, 6H), 1.13 (s, 6H); LC-MS: 533.4 [M+H]$^+$.

Example 43: 3-(4-{[(2,4-difluorophenyl)methyl]({[4-(propan-2-yloxy)phenyl]-methoxy}carbonyl)amino}piperidin-1-yl)-2,2-dimethylpropanoic acid (43)

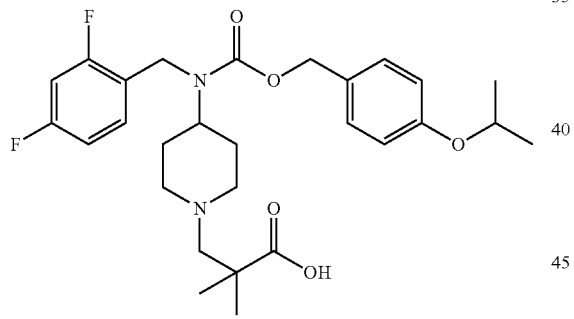

methyl 3-(4-{[(2,4-difluorophenyl)methyl]({[4-(propan-2-yloxy)phenyl]methoxy}carbonyl)amino}piperidin-1-yl)-2,2-dimethylpropanoate (Example 42) (88 mg, 0.165 mmol) was treated with 2 M LiOH in water (1 ml), tetrahydrofuran (1 ml), water (0.5 ml) and ethanol (0.5 ml) for 18 hours and the mixture was partitioned between water and chloroform. Acetic acid (240 μl) was added and pH in the aqueous phase become approximately 5. The aqueous phase was extracted three times with chloroform, the organic phases were collected and evaporated and the crude was purified by column chromatography using silicon dioxide gel, eluting with 10-30% methanol in ethyl acetate to afford the title compound (71 mg, 83% yield): $^1$H NMR (400 MHz, Chloroform-d) δ 7.40-6.96 (m, 3H), 6.96-6.66 (m, 4H), 5.08 (bs, 2H), 4.55 (heptet, 1H), 4.44 (bs, 2H), 4.26-3.65 (m, 1H), 3.13 (d, 2H), 2.54 (bs, 4H), 1.88 (q, 2H), 1.70 (bs, 2H), 1.34 (d, 6H), 1.21 (s, 6H); LC-MS: 519.3 [M+H]$^+$.

Example 44: [4-(propan-2-yloxy)phenyl]methyl N-[(2,4-difluorophenyl)methyl]-N-(1-ethylpiperidin-4-yl)carbamate (44)

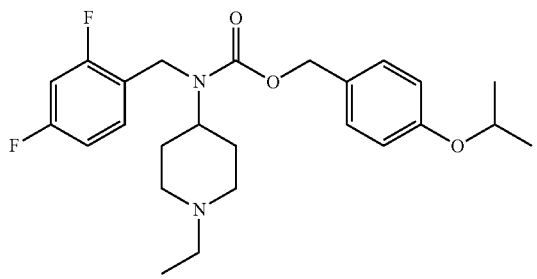 [SMILES: CCN1CCC(N(Cc2ccc(F)cc2F)C(=O)OCc2ccc(OC(C)C)cc2)CC1]

[4-(propan-2-yloxy)phenyl]methyl N-[(2,4-difluorophenyl)methyl]-N-(piperidin-4-yl)carbamate (Example 11) (105 mg, 0.246 mmol) was dissolved in tetrahydrofuran (2.0 ml) and acetaldehyde (1.6 M solution in THF, 0.492 mmol, 310 μl) was added followed by sodium triacetoxyborohydride (0.615 mmol, 135 mg). The reaction was stirred for 1 hour and then the mixture was partitioned between diethyl ether and 0.5 M NaOH. The organic phase was collected, evaporated, and the crude was purified by column chromatography using silicon dioxide gel, eluting with 0-25% methanol in ethyl acetate to afford the title compound (100 mg, 91% yield): $^1$H NMR (400 MHz, Chloroform-d) δ 7.41-6.95 (m, 3H), 6.95-6.64 (m, 4H), 5.23-4.94 (m, 2H), 4.64-4.34 (m, 3H), 4.26-3.75 (m, 1H), 2.96 (d, 2H), 2.38 (q, 2H), 2.05-1.82 (m, 2H), 1.79-1.52 (m, 4H), 1.33 (d, 6H), 1.05 (t, 3H); LC-MS: 447.3 [M+H]$^+$.

Example 45: [4-(propan-2-yloxy)phenyl]methyl N-(1-cyclopropylpiperidin-4-yl)-N-[(2,4-difluorophenyl)methyl]carbamate (45)

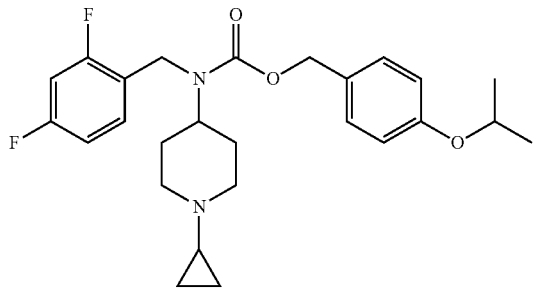 [SMILES: CC(C)Oc1ccc(COC(=O)N(Cc2ccc(F)cc2F)C2CCN(C3CC3)CC2)cc1]

[4-(propan-2-yloxy)phenyl]methyl N-[(2,4-difluorophenyl)methyl]-N-(piperidin-4-yl)carbamate (101 mg, 0.237 mmol) was dissolved in methanol (2.0 ml) and (1-ethoxycyclopropoxy)trimethylsilane (0.752 mmol, 131 mg) was added followed by sodium cyanoborohydride (0.752 mmol, 50 mg). The mixture was stirred 48 hours and then partitioned between diethyl ether and 0.5 M NaOH. The organic phase was collected, evaporated, and the crude was purified by column chromatography using silicon dioxide gel, eluting with 15-50% ethyl acetate in petroleum ether to afford the title compound (35 mg, 32% yield): $^1$H NMR (400 MHz, Chloroform-d) δ 7.42-6.96 (m, 3H), 6.96-6.64 (m, 4H), 5.26-4.93 (m, 2H), 4.62-4.32 (m, 3H), 4.28-3.77 (m, 1H), 3.03 (bs, 2H), 2.41-2.05 (m, 2H), 1.80-1.41 (m, 5H), 1.34 (d, 6H), 0.54-0.23 (m, 4H); LC-MS: 459.3 [M+H]⁺.

Example 46: [4-(propan-2-yloxy)phenyl]methyl N-[(2,4-difluorophenyl)methyl]-N-[1-(oxetan-3-yl)piperidin-4-yl]carbamate (46)

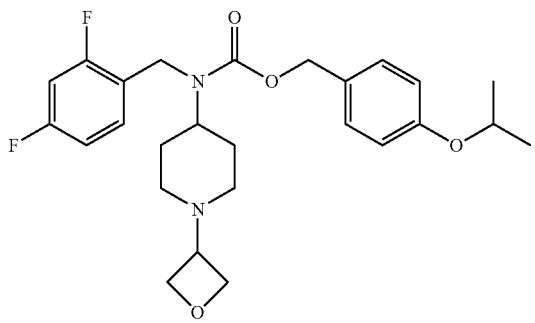 [SMILES: CC(C)Oc1ccc(COC(=O)N(Cc2ccc(F)cc2F)C2CCN(C3COC3)CC2)cc1]

[4-(propan-2-yloxy)phenyl]methyl N-[(2,4-difluorophenyl)methyl]-N-(piperidin-4-yl)carbamate (100 mg, 0.238 mmol) was dissolved in tetrahydrofuran (1.0 ml) and oxetan-3-one (0.478 mmol, 35 mg) dissolved in tetrahydrofuran (1.0 ml) was added followed by sodium triacetoxyborohydride (0.714 mmol, 156 mg). The reaction was stirred for 1 hour and then the mixture was partitioned between diethyl ether and 0.5 M NaOH. The organic phase was collected, evaporated, and the crude was purified by column chromatography using silicon dioxide gel, eluting with 0-5% methanol in ethyl acetate to afford the title compound (85 mg, 76% yield): ¹H NMR (400 MHz, Chloroform-d) δ 7.38-6.96 (m, 3H), 6.96-6.65 (m, 4H), 5.22-4.97 (m, 2H), 4.62 (t, 2H), 4.59-4.38 (m, 3H), 4.56 (t, 2H), 4.25-3.74 (m, 1H), 3.44 (p, 1H), 2.75 (d, 2H), 1.99-1.79 (m, 2H), 1.79-1.53 (m, 4H), 1.34 (d, 6H); LC-MS: 475.3 [M+H]⁺.

Example 47: N-[(2-fluoro-4-methoxyphenyl)methyl]-N-(1-methylpiperidin-4-yl)-2-[4-(2-methylpropoxy)phenyl]acetamide (47)

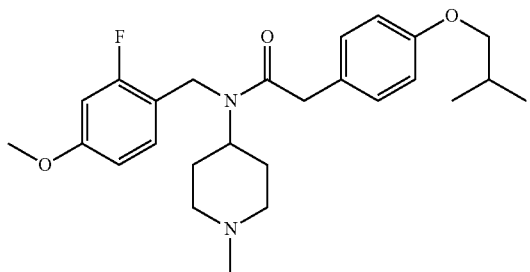 [SMILES: COc1ccc(CN(C(=O)Cc2ccc(OCC(C)C)cc2)C2CCN(C)CC2)c(F)c1]

N-[(2-fluoro-4-methoxyphenyl)methyl]-1-methylpiperidin-4-amine (155 mg, 0.584 mmol) was dissolved in diethyl ether (2.0 ml) and 2-[4-(2-methylpropoxy)phenyl]acetyl chloride (0.70 mmol, 167 mg) in diethyl ether (2.0 ml) was added. The suspension was stirred at 20° C. for 1 hour, then partitioned between 0.5 M NaOH and diethyl ether, the organic phase was separated, concentrated and the crude was purified by column chromatography using silicon dioxide gel, eluting with 0-30% methanol in ethyl acetate to afford fractions. These fractions were combined and evaporated. To the residue was added diethyl ether and the solution was filtered to remove the solids. The clear solution was evaporated and gave the title compound (oil, 162 mg, 62% yield). Two rotamers seen in nmr spectrum: ¹H NMR (400 MHz, Chloroform-d) δ 7.25-6.49 (m, 7H), 4.66-4.42 (m, 3H), 3.84-3.50 (m, 7H), 2.95-2.75 (two doublets, 2H), 2.32-2.19 (two singlets, 3H), 2.18-1.99 (m, 3H), 1.84-1.58 (m, 4H), 1.05-0.99 (m, 6H); LC-MS: 443.3 [M+H]⁺.

Example 48: (2E)-N-[(2,4-difluorophenyl)methyl]-N-(1-methylpiperidin-4-yl)-3-[4-(propan-2-yloxy)phenyl]prop-2-enamide (48)

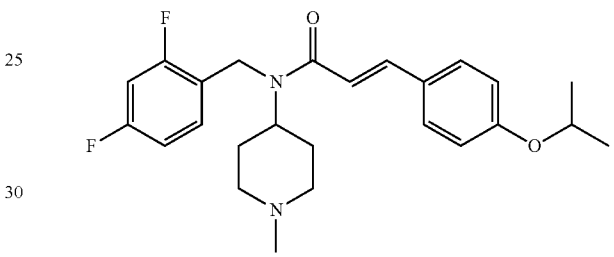

methyl (2E)-3-(4-hydroxyphenyl)prop-2-enoate (1041 mg, 5.7 mmol), Cs₂CO₃ (14.3 mmol, 4.71 g), DMF (10 ml), and 2-iodopropane (14.3 mmol, 1.442 ml) were stirred at 60° C. for 2 hours and then partitioned between diethyl ether and water. The organic phase was washed with brine and evaporated to give an oil that was hydrolyzed in ethanol (10 ml) and aqueous NaOH (2 M, 5.0 ml) for 18 h. Acidification with HCl (1 M) and collecting the precipitate gave the carboxylic acid (997 mg, 4.8 mmol). This acid was stirred in a mixture of dichloromethane (10 ml), oxalyl chloride (12 mmol, 1036 µl) and DMF (20 µl) for 1 hour, it was then concentrated and gave (2E)-3-[4-(propan-2-yloxy)phenyl]prop-2-enoyl chloride (1.1 g).

N-[(2,4-difluorophenyl)methyl]-1-methylpiperidin-4-amine (250 mg, 1.0 mmol) was dissolved in diethyl ether (4 ml) and a solution of (2E)-3-[4-(propan-2-yloxy)phenyl]prop-2-enoyl chloride (1.2 mmol, 284 mg) in diethyl ether (2 ml) was added which resulted in precipitation. The mixture was stirred 30 min, the precipitate was collected by filtration and was then dissolved in MeOH (3 ml). NaOH (1 M) was added to pH>11, followed by water which resulted in precipitation. The suspension was stirred for 1 hour and the crystals were isolated by filtration, washed with 33% aq. McOH, and dried to give the title compound (198 mg, 46% yield): ¹H NMR (400 MHz, Chloroform-d) δ 7.74 (d, 1H), 7.56-7.12 (m, 3H), 6.95-6.70 (d, 5H), 4.79-4.47 (d, 4H), 2.92 (d, 2H), 2.30 (s, 3H), 2.23-1.97 (m, 2H), 1.95-1.63 (m, 4H), 1.34 (m, 6H); LC-MS: 429.3 [M+H]⁺.

Example 49: N-[(2,4-difluorophenyl)methyl]-N-[(3S,4R)-3-fluoro-1-methylpiperidin-4-yl]-2-[4-(propan-2-yloxy)phenyl]acetamide and N-[(2,4-difluorophenyl)methyl]-N-[(3R,4S)-3-fluoro-1-methylpiperidin-4-yl]-2-[4-(propan-2-yloxy)phenyl]acetamide (49)

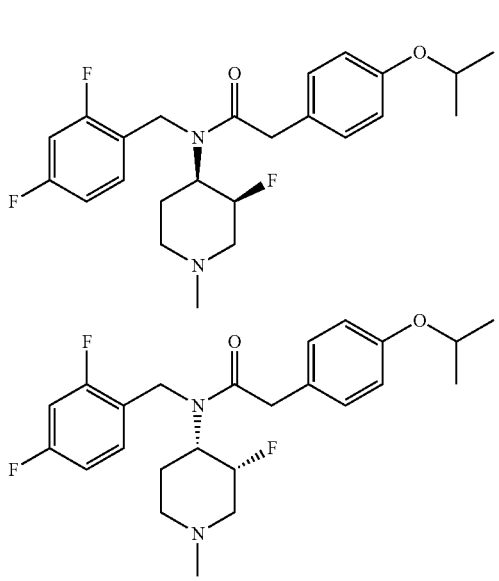

tert-Butyl 4-{[(2,4-difluorophenyl)methyl]amino}-3-fluoropiperidine-1-carboxylate (prepared in analogy with intermediate 7, (N-[(2,4-difluorophenyl)methyl]-1-methylpiperidin-4-amine)) (300 mg, 0.871 mmol) was dissolved in dichloromethane (3.0 ml) and pyridine (3.5 mmol, 283 μl) was added followed by 2-[4-(propan-2-yloxy)phenyl]acetyl chloride (1.3 mmol, 320 μl) dissolved in dichloromethane (2.0 ml) dropwise. The mixture was stirred at room temperature for 30 min, then partitioned between dichloromethane and 0.5 M NaOH, the organic phase was separated, washed with water, dried, then concentrated, and the crude was purified by column chromatography using silicon dioxide gel, eluting with 75-0% ethyl acetate in petroleum ether to afford the desired protected intermediate (403 mg, 89%). This was stirred in dichloromethane (2.0 ml) and trifluoroacetic acid (2.0 ml) for 30 min, then evaporated and free based by partition between diethyl ether and 1 M NaOH. The residue after evaporation of the organic phase was purified by column chromatography using silicon dioxide gel, eluting with 5-50% methanol in ethyl acetate to afford the desired piperidine (235 mg, 0.558 mmol, 72%). This material was dissolved in tetrahydrofuran (3.0 ml), formaldehyde (1.68 mmol, 125 μl) followed by sodium triacetoxyborohydride (1.68 mmol, 367 mg) were added and the mixture was stirred for 1 hour, then partitioned between diethyl ether and 1 M NaOH. The organic phase was separated, dried, evaporated and the crude was purified by column chromatography using silicon dioxide gel, eluting with 0-10% methanol in ethyl acetate to afford the title compound (107 mg, 44%): $^1$H NMR (400 MHz, Chloroform-d) δ 7.23-6.98 (m, 3H), 6.93-6.68 (m, 4H), 4.98-4.15 (m, 5H), 3.55 (s, 2H), 3.17 (t, 1H), 2.95 (d, 1H), 2.49-1.90 (m, 3H), 2.34 (s, 3H), 1.48 (d, 1H), 1.32 (d, 6H); LC-MS: 435.3 [M+H]$^+$.

Example 50: N-{[4-chloro-2-(trifluoromethyl)phenyl]methyl}-N-(1-methylpiperidin-4-yl)-2-[4-(2-methylpropoxy)phenyl]acetamide; trifluoroacetic acid (50)

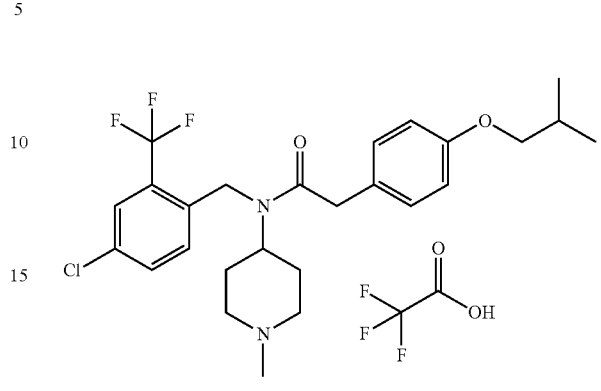

To N-{[4-chloro-2-(trifluoromethyl)phenyl]methyl}-1-methylpiperidin-4-amine (30.7 mg, 100 μmol) (prepared in analogy with intermediate 7 (N-[(2,4-difluorophenyl)methyl]-1-methylpiperidin-4-amine) using [4-chloro-2-(trifluoromethyl)phenyl]methanamine) in dichloromethane was added 2-[4-(2-methylpropoxy)phenyl]acetyl chloride (27.2 mg, 120 μmol) and triethylamine (27.9d, 200 μmol). The reaction was stirred for 1.5 h at rt and then evaporated. The crude material was purified by HPLC, eluting with 20-40% acetonitrile in water (containing 0.1% trifluoroacetic acid) to afford the title compound. Yield: 56%. $^1$H NMR (400 MHz, Chloroform-d) δ 12.80 (bs, 1H), 7.71 (s, 1H), 7.48 (d, 1H), 7.22 (d, 1H), 7.00 (d, 2H), 6.80 (d, 2H), 4.86 (t, 1H), 4.66 (s, 2H), 3.69 (d, 2H), 3.64-3.50 (m, 2H), 3.47 (s, 2H), 2.87-2.68 (m, 5H), 2.17-1.96 (m, 3H), 1.83 (d, 2H), 1.03 (d, 6H); LCMS: 497.3 [M+H]$^+$.

Example 51: N-{[4-fluoro-2-(trifluoromethoxy)phenyl]methyl}-N-(1-methyl-piperidin-4-yl)-2-[4-(2-methylpropoxy)phenyl]acetamide; trifluoroacetic acid (51)

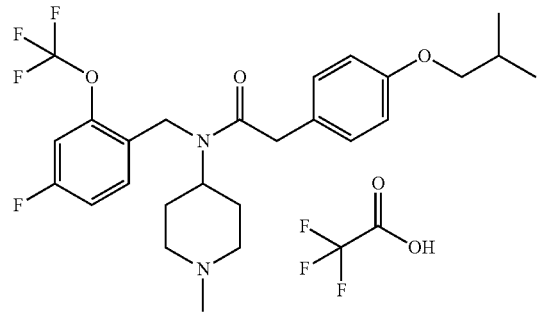

The compounds were prepared in analogy with N-{[4-chloro-2-(trifluoromethyl)-phenyl]methyl}-N-(1-methylpiperidin-4-yl)-2-[4-(2-methylpropoxy)phenyl]acetamide; trifluoroacetic acid (Ex. 50) using [4-fluoro-2-(trifluoromethoxy)phenyl]methanamine. Yield: 52%. $^1$H NMR (400 MHz, Chloroform-d) δ 12.80 (bs, 1H), 7.17-7.11 (m, 1H), 7.11-7.04 (m, 1H), 7.05-6.95 (m, 3H), 6.82 (d, 2H), 4.83 (t, 1H), 4.51 (s, 2H), 3.69 (d, 2H), 3.56 (d, 2H), 3.51 (s, 2H), 2.85-2.67 (m, 5H), 2.15-1.97 (m, 3H), 1.81 (d, 2H), 1.02 (d, 6H); LCMS: 497.3 [M+H]$^+$.

Example 52: N-[(4-fluoro-2-methylphenyl)methyl]-N-(1-methylpiperidin-4-yl)-2-[4-(2-methylpropoxy)phenyl]acetamide; trifluoroacetic acid (52)

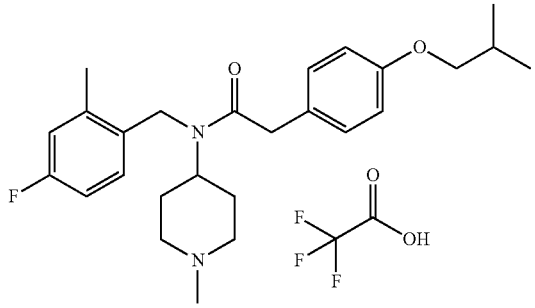

The compounds were prepared in analogy with N-{[4-chloro-2-(trifluoromethyl)-phenyl]methyl}-N-(1-methylpiperidin-4-yl)-2-[4-(2-methylpropoxy)phenyl]acetamide; trifluoroacetic acid (Ex. 50) using (4-fluoro-2-methylphenyl)methanamine. Yield: 76%. $^1$H NMR (400 MHz, Chloroform-d) δ 13.00 (bs, 1H), 7.11-6.99 (m, 3H), 6.97-6.76 (m, 4H), 4.91 (t, 1H), 4.37 (s, 2H), 3.70 (d, 2H), 3.57-3.43 (m, 4H), 2.90-2.66 (m, 5H), 2.28 (s, 3H), 2.22-2.01 (m, 3H), 1.81 (d, 2H), 1.02 (d, 6H); LCMS: 427.3 [M+H]$^+$.

Example 53: N-[(2-chloro-4-methoxyphenyl)methyl]-N-(1-methylpiperidin-4-yl)-2-[4-(2-methylpropoxy)phenyl]acetamide; trifluoroacetic acid (53)

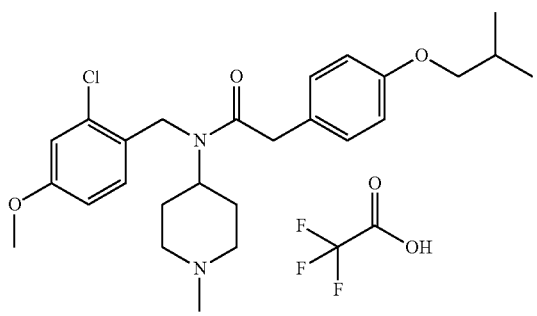

The compounds were prepared in analogy with N-{[4-chloro-2-(trifluoromethyl)-phenyl]methyl}-N-(1-methylpiperidin-4-yl)-2-[4-(2-methylpropoxy)phenyl]acetamide; trifluoroacetic acid (Ex. 50) using (2-chloro-4-methoxyphenyl)methanamine. Yield: 73%. $^1$H NMR (400 MHz, Chloroform-d) δ 13.06 (bs, 1H), 7.23-6.93 (m, 4H), 6.91-6.74 (m, 3H), 4.82 (t, 1H), 4.48 (s, 2H), 3.81 (s, 3H), 3.70 (d, 2H), 3.61-3.47 (m, 4H), 2.93-2.65 (m, 5H), 2.16-1.96 (m, 3H), 1.83 (d, 2H), 1.02 (d, 6H); LCMS: 459.3 [M+H]$^+$.

Example 54: [4-(propan-2-yloxy)phenyl]methyl N-{[4-chloro-2-(trifluoromethyl)-phenyl]methyl}-N-(1-methylpiperidin-4-yl)carbamate; trifluoroacetic acid (54)

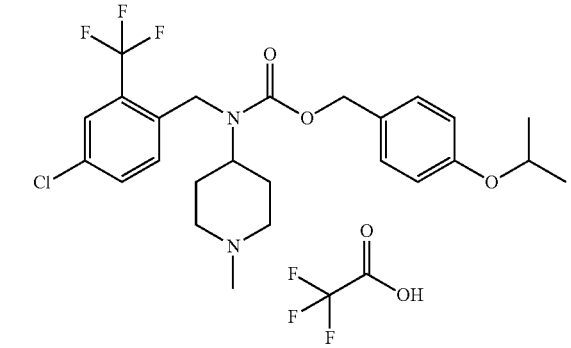

The compounds were prepared in analogy with [4-(propan-2-yloxy)phenyl]methyl-N-[(2-fluoro-4-methoxyphenyl)methyl]-N-(1-methylpiperidin-4-yl)carbamate (Example 41) using N-{[4-chloro-2-(trifluoromethyl)phenyl]methyl}-1-methylpiperidin-4-amine (prepared in analogy with intermediate 7 using [4-chloro-2-(trifluoromethyl)phenyl]methanamine). Yield: 15%. $^1$H NMR (400 MHz, Chloroform-d) δ 13.30 (bs, 1H), 7.62 (s, 1H), 7.40-7.24 (m, 2H), 7.19-6.97 (m, 2H), 6.92-6.67 (m, 2H), 5.20-4.96 (m, 2H), 4.72-4.31 (m, 4H), 3.59 (d, 2H), 2.87-2.64 (m, 5H), 2.36-2.00 (m, 2H), 1.94-1.69 (m, 2H), 1.34 (d, 6H); LCMS: 499.3 [M+H]$^+$.

Example 55: [4-(propan-2-yloxy)phenyl]methyl N-{[4-fluoro-2-(trifluoromethoxy)phenyl]methyl}-N-(1-methylpiperidin-4-yl)carbamate; trifluoroacetic acid (55)

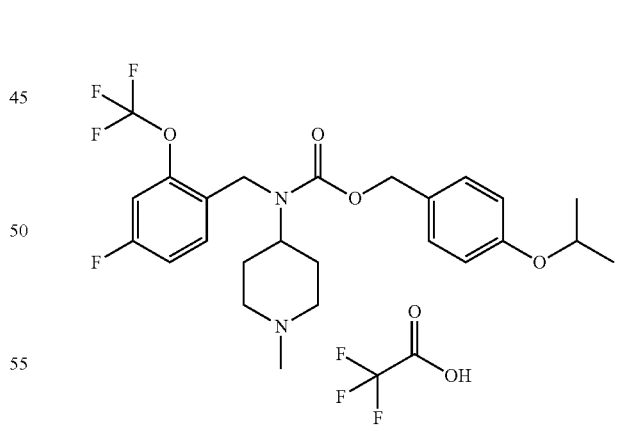

The compounds were prepared in analogy with [4-(propan-2-yloxy)phenyl]methyl-N-[(2-fluoro-4-methoxyphenyl)methyl]-N-(1-methylpiperidin-4-yl)carbamate (Example 41) using N-{[4-chloro-2-(trifluoromethyl)phenyl]methyl}-1-methylpiperidin-4-amine (prepared in analogy with intermediate 7 using [4-fluoro-2-(trifluoromethyl)phenyl]methanamine). Yield: 23%. $^1$H NMR (400 MHz, Chloroform-d) δ 12.87 (bs, 1H), 7.27-6.70 (m, 7H), 5.28-4.95 (m, 2H), 4.70-4.27 (m, 4H), 3.59 (d, 2H), 2.95-2.66 (m, 5H), 2.36-2.09 (m, 2H), 1.97-1.68 (m, 2H), 1.34 (d, 6H); LCMS: 499.3 [M+H]⁺.

Example 56: [4-(propan-2-yloxy)phenyl]methyl N-[(4-fluoro-2-methylphenyl)-methyl]-N-(1-methylpiperidin-4-yl)carbamate; trifluoroacetic acid (56)

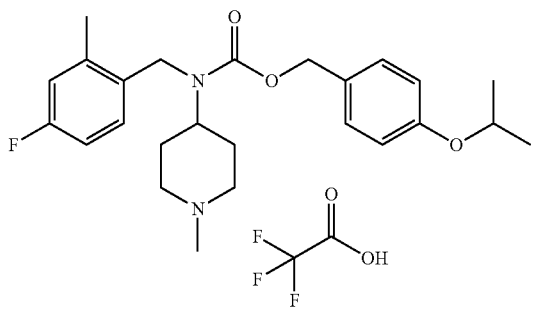

The compounds were prepared in analogy with [4-(propan-2-yloxy)phenyl]methyl-N-[(2-fluoro-4-methoxyphenyl)methyl]-N-(1-methylpiperidin-4-yl)carbamate (Example 41) using N-[(4-fluoro-2-methylphenyl)methyl]-1-methylpiperidin-4-amine (prepared in analogy with intermediate 7 using [4-fluoro-2-methylphenyl]methanamine). Yield: 42%. ¹H NMR (400 MHz, Chloroform-d) δ 13.06 (bs, 1H), 7.27-6.68 (m, 7H), 5.29-4.95 (m, 2H), 4.70-4.25 (m, 4H), 3.53 (d, 2H), 2.83-2.62 (m, 5H), 2.27 (s, 3H), 2.25-2.04 (m, 2H), 1.93-1.61 (m, 2H), 1.34 (d, 6H); LCMS: 429.3 [M+H]⁺.

Example 57: [4-(propan-2-yloxy)phenyl]methyl N-[(2-chloro-4-methoxy-phenyl)methyl]-N-(1-methylpiperidin-4-yl)carbamate; trifluoroacetic acid (57)

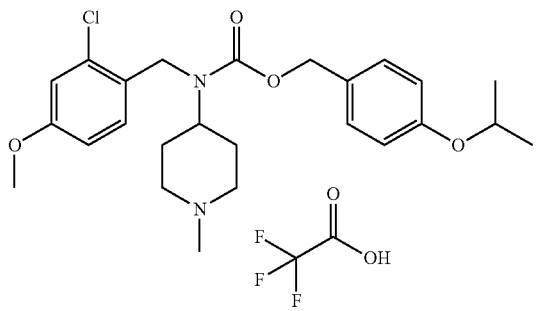

The compounds were prepared in analogy with [4-(propan-2-yloxy)phenyl]methyl-N-[(2-fluoro-4-methoxyphenyl)methyl]-N-(1-methylpiperidin-4-yl)carbamate (Example 41) using N-[(2-chloro-4-methoxyphenyl)methyl]-1-methylpiperidin-4-amine (prepared in analogy with intermediate 6 using (2-chloro-4-methoxyphenyl)methanamine). Yield: 44%. H NMR (400 MHz, Chloroform-d) δ 13.32 (bs, 1H), 7.29-7.11 (m, 2H), 6.99-6.59 (m, 5H), 5.27-5.00 (m, 2H), 4.70-4.17 (m, 4H), 3.78 (s, 3H), 3.56 (d, 2H), 2.78-2.67 (m, 5H), 2.38-2.01 (m, 2H), 1.93-1.62 (m, 2H), 1.33 (d, 6H); LCMS: 461.3 [M+H]⁺.

Example 58: [4-(2-methylpropoxy)phenyl]methyl N-[(2-chloro-4-fluorophenyl)methyl]-N-(1-methylpiperidin-4-yl)carbamate (58)

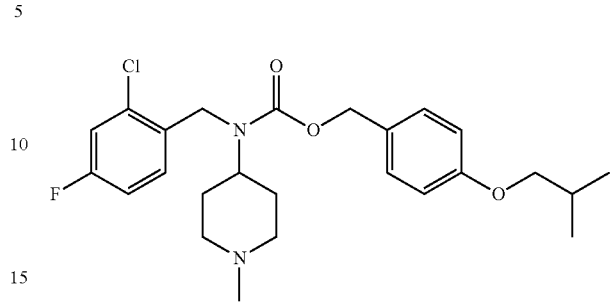

The compounds were prepared in analogy with [4-(propan-2-yloxy)phenyl]methyl-N-[(2-fluoro-4-methoxyphenyl)methyl]-N-(1-methylpiperidin-4-yl)carbamate (Example 41) using N-[(2-chloro-4-fluorophenyl)methyl]-1-methylpiperidin-4-amine (prepared in analogy with intermediate 7 using (2-chloro-4-fluorophenyl)methanamine). Yield: 65%. ¹H NMR (400 MHz, Chloroform-d) δ 7.42-6.74 (m, 7H), 5.24-4.96 (m, 2H), 4.45 (s, 2H), 4.30-3.83 (m, 1H), 3.79-3.57 (m, 2H), 2.91 (d, 2H), 2.27 (s, 3H), 2.19-1.99 (m, 3H), 1.82-1.51 (m, 4H), 1.02 (d, 6H); LCMS: 463.3 [M+H]⁺.

Example 59: N-[(2,4-dichlorophenyl)methyl]-N-(1-methylpiperidin-4-yl)-2-[4-(2-methylpropoxy)phenyl]acetamide; trifluoroacetic acid (59)

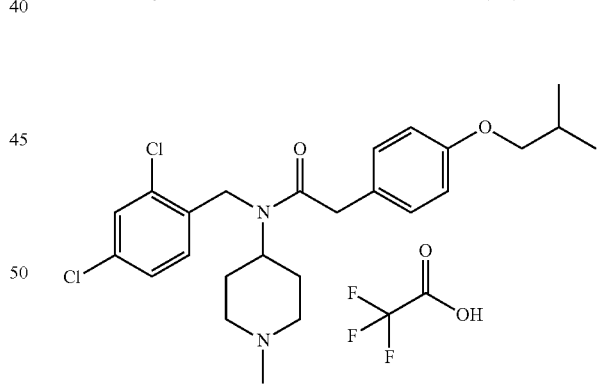

The compounds were prepared in analogy with N-{[4-chloro-2-(trifluoromethyl)-phenyl]methyl}-N-(1-methylpiperidin-4-yl)-2-[4-(2-methylpropoxy)phenyl]acetamide; trifluoroacetic acid (50) using (2,4-dichlorophenyl)methanamine. Yield: 49%. ¹H NMR (400 MHz, Chloroform-d) δ 12.82 (bs, 1H), 7.45 (s, 1H), 7.24 (d, 1H), 7.06 (s, 1H), 7.02 (d, 2H), 6.82 (d, 2H), 4.95-4.79 (m, 1H), 4.51 (s, 2H), 3.70 (d, 2H), 3.57 (d, 2H), 3.48 (s, 2H), 2.93-2.69 (m, 5H), 2.20-2.02 (m, 3H), 1.84 (d, 2H), 1.03 (d, 6H); LCMS: 463.2 [M+H]⁺.

Example 60: N-[(2,4-dichlorophenyl)methyl]-N-(1-methylpiperidin-4-yl)-2-[4-(propan-2-yloxy)phenyl]acetamide; trifluoroacetic acid (60)

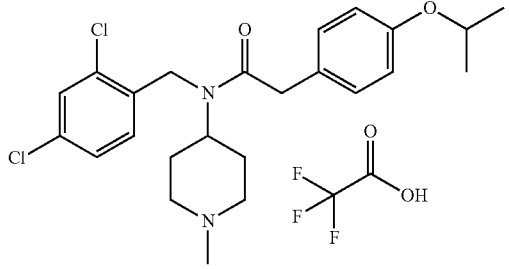

The compounds were prepared in analogy with N-{[4-chloro-2-(trifluoromethyl)-phenyl]methyl}-N-(1-methylpiperidin-4-yl)-2-[4-(2-methylpropoxy)phenyl]acetamide; trifluoroacetic acid (50) using (2,4-dichlorophenyl)methanamine and 1-(isocyanatomethyl)-4-(propan-2-yloxy)benzene. Yield: 54%. $^1$H NMR (400 MHz, Chloroform-d) δ 12.80 (bs, 1H), 7.45 (d, 1H), 7.23 (dd, 1H), 7.05 (d, 1H), 7.01 (d, 2H), 6.80 (d, 2H), 4.85 (t, 1H), 4.65-4.42 (m, 3H), 3.57 (d, 2H), 3.48 (s, 2H), 2.88-2.68 (m, 5H), 2.18-2.00 (m, 2H), 1.83 (d, 2H), 1.33 (d, 6H); LCMS: 449.2 [M+H]$^+$.

Example 61: N-[(2-chloro-4-fluorophenyl)methyl]-N-(1-methylpiperidin-4-yl)-2-[4-(2-methylpropoxy)phenyl]acetamide; trifluoroacetic acid (61)

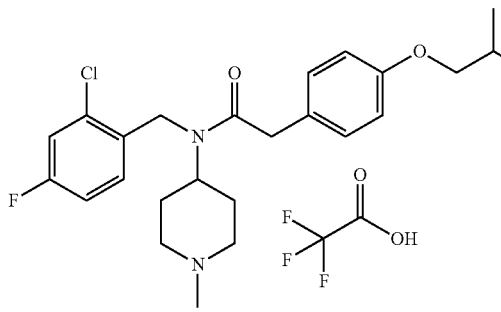

The compounds were prepared in analogy with N-{[4-chloro-2-(trifluoromethyl)-phenyl]methyl}-N-(1-methylpiperidin-4-yl)-2-[4-(2-methylpropoxy)phenyl]acetamide; trifluoroacetic acid (50) using (2-chloro-4-fluorophenyl)methanamine. Yield: 54%. $^1$H NMR (400 MHz, Chloroform-d) δ 12.83 (bs, 1H), 7.20 (dd, 1H), 7.13-7.06 (m, 1H), 7.03 (d, 2H), 6.98 (td, 1H), 6.82 (d, 2H), 4.85 (t, 1H), 4.50 (s, 2H), 3.70 (d, 2H), 3.57 (d, 2H), 3.49 (s, 2H), 2.88-2.67 (m, 5H), 2.17-1.98 (m, 3H), 1.83 (d, 2H), 1.02 (d, 6H); LCMS: 447.3 [M+H]$^+$

Example 62: N-[(2-chloro-4-fluorophenyl)methyl]-N-(1-methylpiperidin-4-yl)-2-[4-(propan-2-yloxy)phenyl]acetamide; trifluoroacetic acid (62)

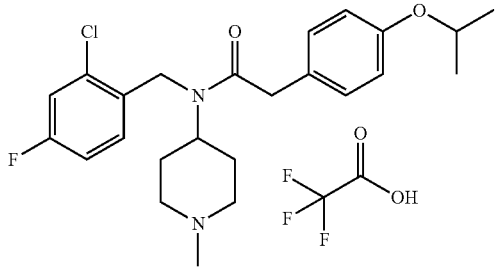

The compounds were prepared in analogy with N-{[4-chloro-2-(trifluoromethyl)-phenyl]methyl}-N-(1-methylpiperidin-4-yl)-2-[4-(2-methylpropoxy)phenyl]acetamide; trifluoroacetic acid (50) using (2-chloro-4-fluorophenyl)methanamine and 1-(isocyanatomethyl)-4-(propan-2-yloxy)benzene. Yield: 49%. 1H NMR (400 MHz, Chloroform-d) δ 12.98 (bs, 1H), 7.20 (dd, 1H), 7.12-7.05 (m, 1H), 7.02 (d, 2H), 6.97 (td, 1H), 6.81 (d, 2H), 4.85 (t, 1H), 4.62-4.43 (m, 3H), 3.56 (d, 2H), 3.49 (s, 2H), 2.87-2.66 (m, 5H), 2.09 (q, 2H), 1.83 (d, 2H), 1.33 (d, 6H); LCMS: 433.3 [M+H]$^+$.

Example 63: [4-(propan-2-yloxy)phenyl]methyl N-[(2-chloro-4-fluorophenyl)-methyl]-N-(1-methylpiperidin-4-yl)carbamate (63)

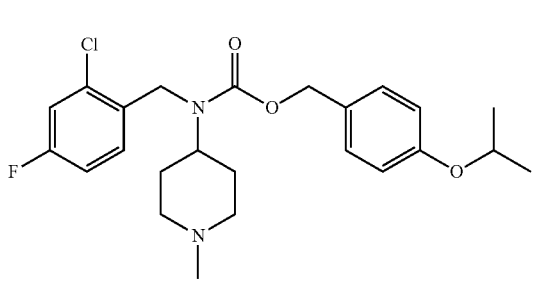

The compounds were prepared in analogy with [4-(propan-2-yloxy)phenyl]methyl-N-[(2-fluoro-4-methoxyphenyl)methyl]-N-(1-methylpiperidin-4-yl)carbamate (Example 41) using N-[(2-chloro-4-fluorophenyl)methyl]-1-methylpiperidin-4-amine (prepared in analogy with intermediate 7 using (2-chloro-4-fluorophenyl)methanamine). Yield: 47%. H NMR (400 MHz, Chloroform-d) δ 7.47-6.55 (m, 7H), 5.05 (s, 2H), 4.71-4.35 (m, 3H), 4.35-3.81 (m, 1H), 3.00 (s, 2H), 2.35 (s, 3H), 2.29-2.04 (m, 2H), 1.92-1.75 (m, 2H), 1.75-1.56 (m, 2H), 1.34 (d, 6H); LCMS: 449.3 [M+H]$^+$.

Example 64: [4-(2-methylpropoxy)phenyl]methyl N-[(2,4=dichlorophenyl)methyl]-N-(1-methylpiperidin-4-yl)carbamate (64)

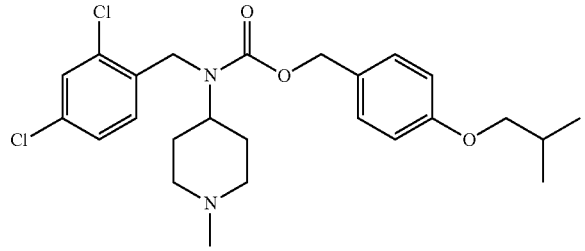 [SMILES: CC(C)COc1ccc(COC(=O)N(Cc2ccc(Cl)cc2Cl)C2CCN(C)CC2)cc1]

The compounds were prepared in analogy with [4-(propan-2-yloxy)phenyl]methyl-N-[(2-fluoro-4-methoxyphenyl)methyl]-N-(1-methylpiperidin-4-yl)carbamate (Example 41) using N-[(2,4-dichlorophenyl)methyl]-1-methylpiperidin-4-amine (prepared in analogy with intermediate 7 using (2,4-dichlorophenyl)methanamine) and [4-(2-methylpropoxy)phenyl]methyl 4-nitrophenyl carbonate (prepared in analogy with intermediate 5 using [4-(2-methylpropoxy)phenyl]methanol). Yield: 64%. $^1$H NMR (400 MHz, Chloroform-d) δ 7.44-6.65 (m, 7H), 5.33-4.97 (m, 2H), 4.65-4.36 (m, 2H), 4.32-3.80 (m, 1H), 3.71 (d, 2H), 2.90 (d, 2H), 2.27 (s, 3H), 2.18-2.00 (m, 3H), 1.80-1.51 (m, 4H), 1.03 (d, 6H); LCMS: 479.2 [M+H]$^+$.

Example 66: [4-(propan-2-yloxy)phenyl]methyl N-(1-methylpiperidin-4-yl)-N-[(2,3,6-trifluorophenyl)methyl]carbamate (66)

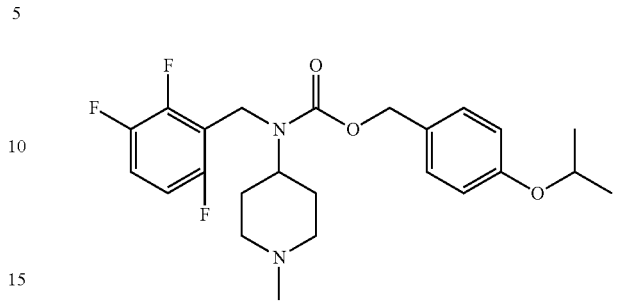

The compounds were prepared in analogy with [4-(propan-2-yloxy)phenyl]methyl-N-[(2-fluoro-4-methoxyphenyl)methyl]-N-(1-methylpiperidin-4-yl)carbamate (Example 41) using 1-methyl-N-[(2,3,6-trifluorophenyl)methyl]piperidin-4-amine (prepared in analogy with intermediate 7 using (2,3,6-trifluorophenyl)methanamine). Yield: 34%. $^1$H NMR (400 MHz, Chloroform-d) δ 7.26-7.08 (m, 2H), 7.07-6.94 (m, 1H), 6.83 (d, 2H), 6.79-6.66 (m, 1H), 5.06 (s, 2H), 4.68-4.43 (m, 3H), 4.09-3.54 (m, 1H), 2.93 (d, 2H), 2.30 (s, 3H), 2.18-1.97 (m, 2H), 1.94-1.77 (m, 2H), 1.71 (d, 2H), 1.34 (d, 6H); LCMS: 451.3 [M+H]$^+$.

Example 65: [4-(propan-2-yloxy)phenyl]methyl N-[(2,6-difluoro-3-methylphenyl)methyl]-N-(1-methylpiperidin-4-yl)carbamate (65)

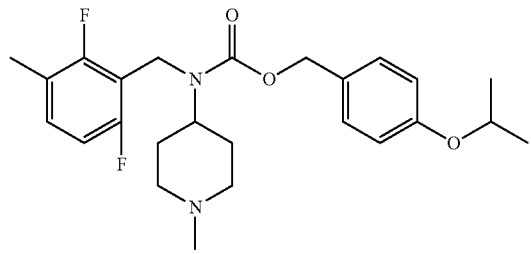 [SMILES: Cc1ccc(F)c(CN(C(=O)OCc2ccc(OC(C)C)cc2)C2CCN(C)CC2)c1F]

The compound was prepared in analogy with [4-(propan-2-yloxy)phenyl]methyl-N-[(2-fluoro-4-methoxyphenyl)methyl]-N-(1-methylpiperidin-4-yl)carbamate (Example 41) using N-[(2,6-difluoro-3-methylphenyl)methyl]-1-methylpiperidin-4-amine (prepared in analogy with intermediate 7 using (2,6-difluoro-3-methylphenyl)methanamine). Yield: 40%. $^1$H NMR (400 MHz, Chloroform-d) δ 7.26-7.11 (m, 2H), 7.01 (q, 1H), 6.83 (d, 2H), 6.71 (t, 1H), 5.07 (s, 2H), 4.68-4.46 (m, 3H), 4.00-3.57 (m, 1H), 2.90 (d, 2H), 2.28 (s, 3H), 2.18 (s, 3H), 2.14-1.95 (m, 2H), 1.95-1.80 (m, 2H), 1.75-1.58 (m, 2H), 1.33 (d, 6H); LCMS: 447.3 [M+H]$^+$.

Example 67: [4-(propan-2-yloxy)phenyl]methyl N-[(2,4-difluoro-3-methylphenyl)methyl]-N-(1-methylpiperidin-4-yl)carbamate (67)

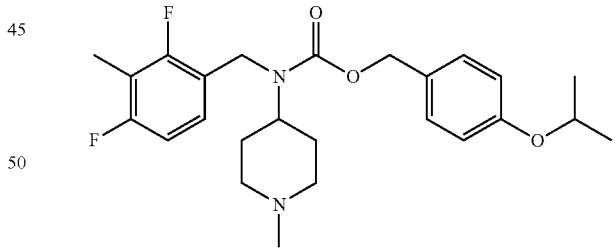

The compounds were prepared in analogy with [4-(propan-2-yloxy)phenyl]methyl-N-[(2-fluoro-4-methoxyphenyl)methyl]-N-(1-methylpiperidin-4-yl)carbamate (Example 41) using N-[(2,4-difluoro-3-methylphenyl)methyl]-1-methylpiperidin-4-amine (prepared in analogy with intermediate 7 using (2,4-difluoro-3-methylphenyl)methanamine). Yield: 53%. $^1$H NMR (400 MHz, Chloroform-d) δ 7.43-6.61 (m, 6H), 5.06 (s, 2H), 4.63-4.33 (m, 3H), 4.22-3.76 (m, 1H), 2.89 (d, 2H), 2.28 (s, 3H), 2.16 (s, 3H), 2.13-1.90 (m, 2H), 1.83-1.68 (m, 2H), 1.68-1.52 (m, 2H), 1.33 (d, 6H); LCMS: 447.3 [M+H]$^+$.

Example 68: [4-(propan-2-yloxy)phenyl]methyl N-[(2-fluoro-4-methylphenyl)-methyl]-N-(1-methylpiperidin-4-yl)carbamate (68)

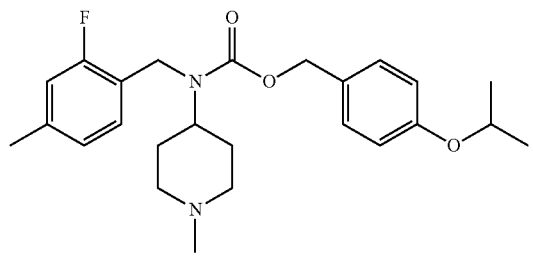 [SMILES: Cc1ccc(CN(C(=O)OCc2ccc(OC(C)C)cc2)C2CCN(C)CC2)c(F)c1]

The compounds were prepared in analogy with [4-(propan-2-yloxy)phenyl]methyl-N-[(2-fluoro-4-methoxyphenyl)methyl]-N-(1-methylpiperidin-4-yl)carbamate (Example 41) using N-[(2-fluoro-4-methylphenyl)methyl]-1-methylpiperidin-4-amine (prepared in analogy with intermediate 7 using (2-fluoro-4-methylphenyl)methanamine). Yield: 45%. $^1$H NMR (400 MHz, Chloroform-d) δ 7.40-6.72 (m, 7H), 5.07 (s, 2H), 4.62-4.37 (m, 3H), 4.24-3.72 (m, 1H), 2.89 (d, 2H), 2.31 (s, 3H), 2.28 (s, 3H), 2.16-1.94 (m, 2H), 1.87-1.69 (m, 2H), 1.69-1.52 (m, 2H), 1.34 (d, 6H); LCMS: 429.3 [M+H]$^+$.

General Procedures (GP)

Scheme S1: General procedure A (GP A), used to prepare compounds 69-71.

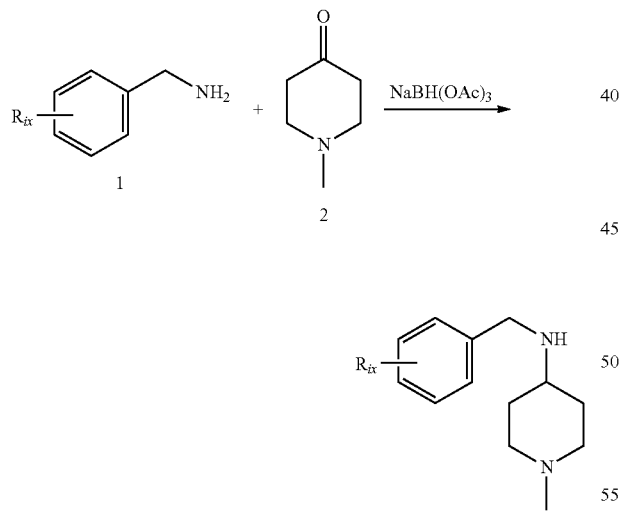

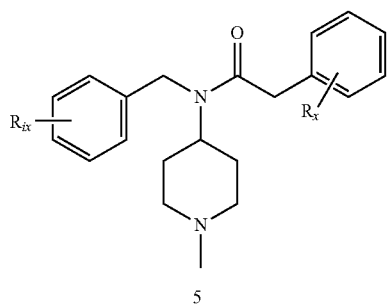

Amine 1 (1.1 equiv.) was added to ketone 2 (1.0 equiv.) in CH$_2$Cl$_2$ followed by addition of sodium triacetoxyborohydride (1.5 equiv.). The reaction mixture was stirred for 3 hours at room temperature, then concentrated under reduced pressure. The residue was diluted with NaOH (1 M, aq.) and extracted with CH$_2$Cl$_2$. The organic phase was dried and concentrated under reduced pressure to give secondary amines 3, that was used in the next step without purification or purified by silica gel column chromatography. Acid chloride 4 (1.25 equiv.) was added dropwise to a solution of a secondary amine 3 (1.0 equiv.) and DIPEA (3.0 equiv.) in CH$_2$Cl$_2$ at room temperature. The reaction mixture was stirred overnight. The mixture was concentrated under reduced pressure and the desired urea 5 was purified by preparative HPLC eluting with acetonitrile in water (containing 0.1% trifluoroacetic acid) to afford the TFA salt of the product or purified by preparative HPLC eluting with acetonitrile in water, containing 6 ppm ammonia (28% aq.), to afford the product as the free base.

Scheme S2: General procedure B (GP B), used to prepare compounds 72-74.

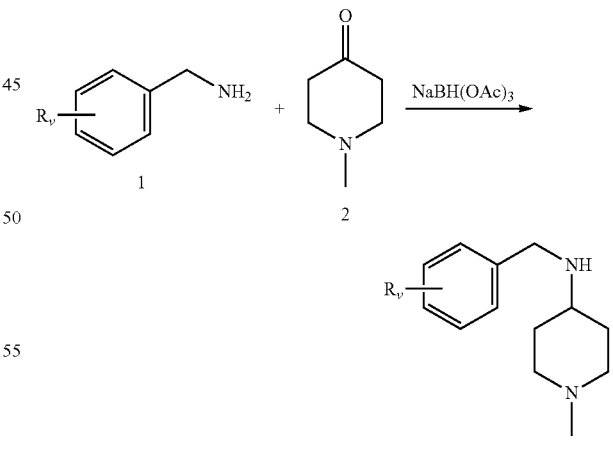

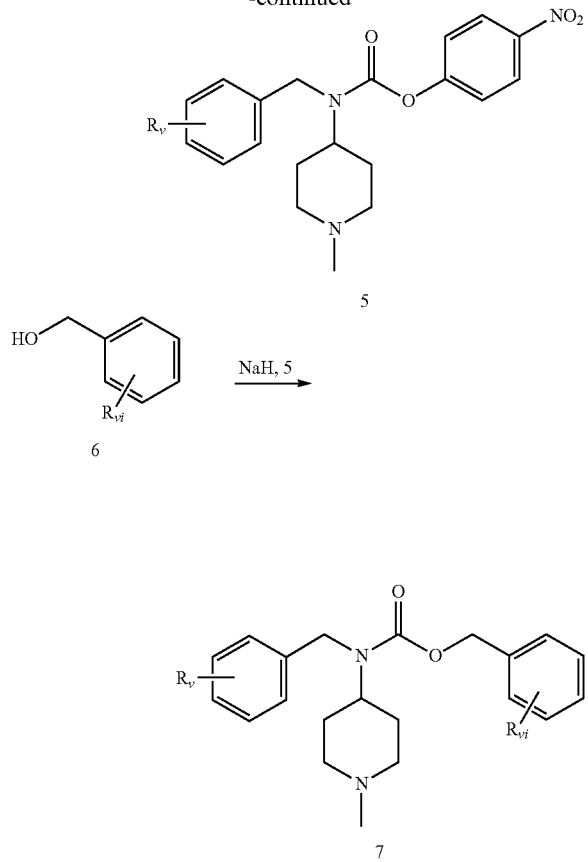

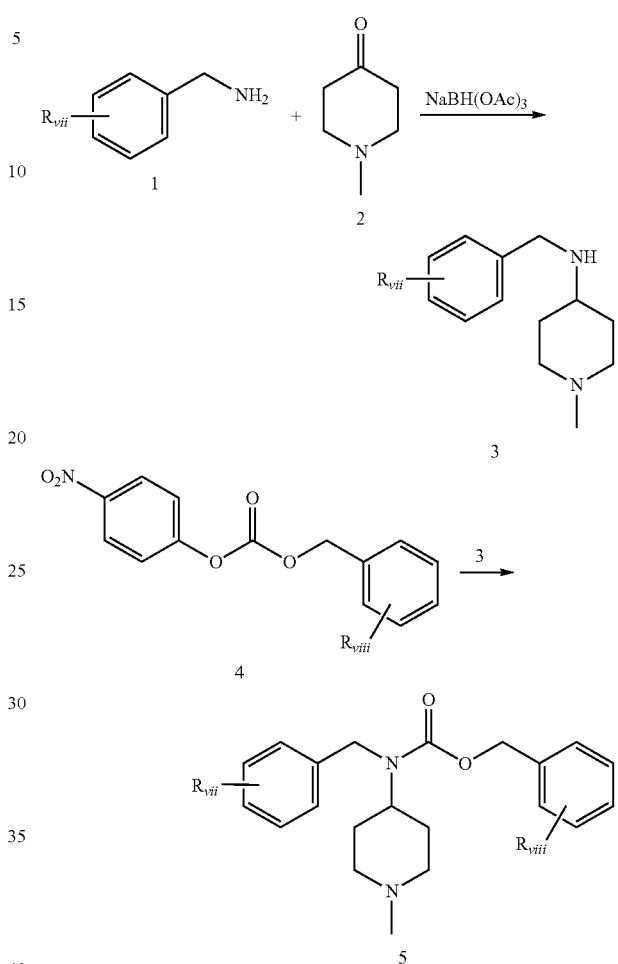

Scheme S3: General procedure C
(GP C), used to prepare compounds 75-81.

Amine 1 (1.1 equiv.) was added to ketone 2 (1.0 equiv.) in CH$_2$Cl$_2$ followed by addition of sodium triacetoxyborohydride (1.5 equiv.). The reaction mixture was stirred for 3 hours at room temperature, then concentrated under reduced pressure. The residue was diluted with NaOH (1 M, aq.) and extracted with CH$_2$Cl$_2$. The organic phase was dried and concentrated under reduced pressure to give secondary amines 3, used in the next step without purification or purified by silica gel column chromatography. The secondary amine 3 (1.0 equiv.) was dissolved in diethyl ether, cooled down on an ice bath and a solution of 4-nitrophenyl chloroformate 4 (1.1 equiv.) in diethyl ether was added dropwise giving a precipitate. The precipitate was stirred for 10 min at room temperature, then NaHCO$_3$ (sat. aq.) was added. The organic phase was separated, dried, and concentrated under reduced pressure. The crude intermediate 5 was purified by silica gel column chromatography. NaH (60% on mineral oil, 2.0 equiv.) was added in portions to alcohol 6 (1.5 equiv.) in THF at room temperature. After gas liberation was complete the obtained suspension was added to a stirred solution of intermediate 5 (1.0 equiv.) in THF at room temperature. The reaction mixture was stirred for 4 hours and partitioned between diethyl ether and NaOH (1 M aq.). The organic phase was dried and concentrated under reduced pressure. The crude product was purified by silica gel column chromatography giving the desired carbamate 7.

Amine 1 (1.1 equiv.) was added to ketone 2 (1.0 equiv.) in CH$_2$Cl$_2$ followed by addition of sodium triacetoxyborohydride (1.5 equiv.). The reaction mixture was stirred for 3 hours at room temperature, then concentrated under reduced pressure. The residue was diluted with NaOH (1 M, aq.) and extracted with CH$_2$Cl$_2$. The organic phase was dried and concentrated under reduced pressure to give secondary amines 3, used in the next step without purification or purified by silica gel column chromatography. Carbonate 4 (1.2 equiv.), made in analogy with 4-nitrophenyl [4-(propan-2-yloxy)phenyl]methyl carbonate, was added to secondary amine 3 (1.0 equiv.) in DMF. The mixture was heated to 60° C. and stirred for 6 hours, then NaOH (1 M aq.) was added and the mixture extracted with CH$_2$Cl$_2$. The organic phase was dried and concentrated under reduced pressure. The crude product was purified by silica gel column chromatography giving the desired carbamate 5.

In Schemes S1-S3 above R$_V$, R$_{VI}$, R$_{VII}$, R$_{VIII}$, R$_{IX}$, and R$_X$ are independently present 1 or 2 times and the respective R-group is disclosed in the final compound in Table 1, i.e. in Example 69, R$_X$ is present once and 4-(2-methylpropoxyl, R$_{XI}$ is present twice and fluoro and —CF$_3$.

TABLE 1

Compounds prepared by GP A, GP B and GP C.

Compounds obtained by GP A

| | | Starting materials | | |
|---|---|---|---|---|
| Example | Structure | Amine 1 | Ketone 2 | Acid chloride 4 |
| 69 | | [2-fluoro-4-(trifluoromethyl)phenyl]methanamine* | 1-methyl-piperidin-4-one* | 2-[4-(2-methylpropoxy)phenyl]acetyl chloride** |
| 70 | | [2-methoxy-4-(trifluoromethyl)phenyl]methanamine* | 1-methyl-piperidin-4-one* | 2-[4-(2-methylpropoxy)phenyl]acetyl chloride** |
| 71 | | [2-chloro-4-(trifluoromethyl)phenyl]methanamine* | 1-methyl-piperidin-4-one* | 2-[4-(2-methylpropoxy)phenyl]acetyl chloride** |

Compounds obtained using GP B

| | | Starting materials | | |
|---|---|---|---|---|
| Example | Structure | Amine 1 | Ketone 2 | Alcohol 6 |
| 72 | | (2,4-difluorophenyl)methanamine* | 1-methyl-piperidin-4-one* | [4-(tert-butoxy)phenyl]methanol* |

TABLE 1-continued

Compounds prepared by GP A, GP B and GP C.

| | | | | |
|---|---|---|---|---|
| 73 | 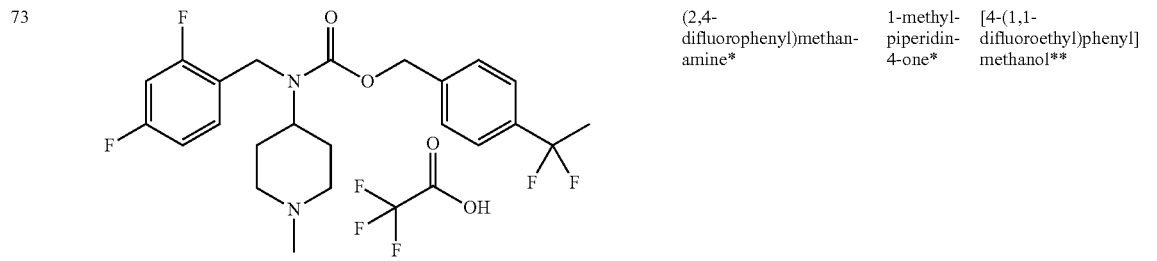 | (2,4-difluorophenyl)methanamine* | 1-methyl-piperidin-4-one* | [4-(1,1-difluoroethyl)phenyl]methanol** |
| 74 | 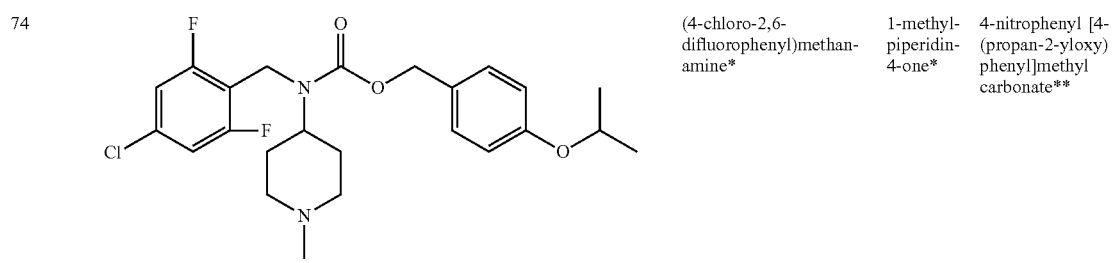 | (4-chloro-2,6-difluorophenyl)methanamine* | 1-methyl-piperidin-4-one* | 4-nitrophenyl [4-(propan-2-yloxy)phenyl]methyl carbonate** |

Compounds obtained using GP C

| | | Starting materials | | |
|---|---|---|---|---|
| Example | Structure | Amine 1 | Ketone 2 | Carbonate 4 |
| 75 | | (4-chloro-3-methoxyphenyl)methanamine* | 1-methyl-piperidin-4-one* | 4-nitrophenyl [4-(propan-2-yloxy)phenyl]methyl carbonate** |
| 76 | | (4-chloro-2-methoxyphenyl)methanamine* | 1-methyl-piperidin-4-one* | 4-nitrophenyl [4-(propan-2-yloxy)phenyl]methyl carbonate** |
| 77 | | [2-methoxy-4-(trifluoromethyl)phenyl]methanamine* | 1-methyl-piperidin-4-one* | 4-nitrophenyl [4-(propan-2-yloxy)phenyl]methyl carbonate** |

TABLE 1-continued

Compounds prepared by GP A, GP B and GP C.

| # | Structure | | | |
|---|---|---|---|---|
| 78 | [structure: 2-chloro-4-(trifluoromethyl)benzyl piperidine carbamate with 4-isopropoxybenzyl, N-methyl piperidine, TFA salt] | [2-chloro-4-(trifluoromethyl)phenyl]methanamine* | 1-methyl-piperidin-4-one* | 4-nitrophenyl [4-(propan-2-yloxy)phenyl]methyl carbonate** |
| 79 | [structure: 2-fluoro-4-(trifluoromethyl)benzyl analog, TFA salt] | [2-fluoro-4-(trifluoromethyl)phenyl]methanamine* | 1-methyl-piperidin-4-one* | 4-nitrophenyl [4-(propan-2-yloxy)phenyl]methyl carbonate** |
| 80 | [structure: 2,4,5-trifluorobenzyl analog] | (2,4,5-trifluorophenyl)methanamine* | 1-methyl-piperidin-4-one* | 4-nitrophenyl [4-(propan-2-yloxy)phenyl]methyl carbonate** |
| 81 | [structure: 4-fluoro-2-(trifluoromethyl)benzyl analog] | [4-fluoro-2-(trifluoromethyl)phenyl]methanamine* | 1-methyl-piperidin-4-one* | 4-nitrophenyl [4-(propan-2-yloxy)phenyl]methyl carbonate** |

*Commercially available **prepared intermediate descried herein.

TABLE 2 characterization of compounds

| Example | NMR | m/z [M + H]+ |
|---|---|---|
| 69 | $^1$H NMR (400 MHz, Chloroform-d) δ 12.44 (bs, 1H), 7.36-7.23 (m, 1H), 7.22-7.03 (m, 2H), 6.89 (d, 2H), 6.69 (d, 2H), 4.72 (t, 1H), 4.48 (s, 2H), 3.56 (d, 2H), 3.48-3.32 (m, 4H), 2.69 (t, 2H), 2.61 (s, 3H), 2.11-1.86 (m, 3H), 1.69 (d, 2H), 0.89 (d, 6H). | 481.3 |
| 70 | $^1$H NMR (400 MHz, Chloroform-d) δ 12.35 (bs, 1H), 7.22-7.12 (m, 2H), 7.10 (s, 1H), 7.02 (d, 2H), 6.81 (d, 2H), 4.87 (t, 1H), 4.51 (s, 2H), 3.91 (s, 3H), 3.68 (d, 2H), 3.59-3.48 (m, 4H), 2.87-2.71 (m, 5H), 2.15-1.98 (m, 3H), 1.81 (d, 2H), 1.01 (d, 6H). | 493.3 |
| 71 | $^1$H NMR (400 MHz, Chloroform-d) δ 12.82 b(s, 1H), 7.70 (s, 1H), 7.49 (d, 1H), 7.24 (d, 1H), 7.00 (d, 2H), 6.80 (d, 2H), 4.90 (s, 1H), 4.59 (s, 2H), 3.68 (d, 2H), 3.55 (d, 2H), 3.46 (s, 2H), 2.87-2.70 (m, 5H), 2.34-1.99 (m, 3H), 1.84 (d, 2H), 1.02 (d, 6H). | 497.3 |

TABLE 2-continued characterization of compounds

| Example | NMR | m/z [M + H]+ |
|---|---|---|
| 72 | 1H NMR (400 MHz, Chloroform-d) δ 12.77 (s, 1H), 7.40-6.89 (m, 5H), 6.87-6.65 (m, 2H), 5.21-5.03 (m, 2H), 4.56-4.41 (m, 2H), 4.36 (s, 1H), 3.59 (d, 2H), 2.86-2.61 (m, 5H), 2.38-2.10 (m, 2H), 1.92-1.66 (m, 2H), 1.34 (s, 9H). | 447.3 |
| 73 | 1H NMR (400 MHz, Chloroform-d) δ 12.70 (bs, 1H), 7.26 (m, 4H), 7.03 (s, 1H), 6.77 (m, 2H), 5.17 (s, 2H), 4.48 (s, 2H), 4.35 (m, 1H), 3.60 (d, 2H), 2.68 (m, 5H), 2.24 (m, 2H), 1.91 (m, 5H). | 439.2 |
| 74 | 1H NMR (400 MHz, Chloroform-d) δ 7.17 (bs, 2H), 6.83 (d, 4H), 5.04 (s, 2H), 4.63-4.36 (m, 3H), 3.96 (bs, 1H), 2.98 (bs, 2H), 2.35 (s, 3H), 2.18 (bs, 2H), 1.96 (bs, 2H), 1.72 (bs, 2H), 1.39-1.29 (m, 6H). | 466.9 |
| 75 | 1H NMR (400 MHz, DMSO-d6) δ 9.18 (bs, 1H), 7.34 (d, 1H), 7.31-7.11 (m, 2H), 6.98-6.81 (m, 3H), 6.78 (d, 1H), 5.04 (s, 2H), 4.65-4.54 (m, 1H), 4.41 (s, 2H), 4.08-3.95 (m, 1H), 3.70 (s, 3H), 3.38 (d, 2H), 3.07-2.94 (m, 2H), 2.70 (d, 3H), 2.01-1.80 (m, 2H), 1.80-1.69 (m, 2H), 1.25 (d, 6H). | 461.3 |
| 76 | 1H NMR (400 MHz, DMSO-d6) δ 9.14 (bs, 1H), 7.38-7.10 (m, 2H), 7.06 (s, 1H), 6.99 (d, 1H), 6.96-6.77 (m, 3H), 5.18-4.91 (m, 2H), 4.66-4.53 (m, 1H), 4.29 (s, 2H), 4.11-3.98 (m, 1H), 3.82 (s, 3H), 3.37 (d, 2H), 3.08-2.94 (m, 2H), 2.70 (d, 3H), 2.01-1.72 (m, 4H), 1.25 (d, 6H). | 461.3 |
| 77 | 1H NMR (400 MHz, Chloroform-d) δ 12.77 (bs, 1H), 7.40-6.96 (m, 5H), 6.94-6.72 (m, 2H), 5.19-4.95 (m, 2H), 4.47 (d, 4H), 3.86 (s, 3H), 3.56 (d, 2H), 2.84-2.61 (m, 5H), 2.11 (d, 2H), 1.81 (d, 2H), 1.32 (d, 6H). | 495.3 |
| 78 | 1H NMR (400 MHz, Chloroform-d) δ 13.03 (bs, 1H), 7.61 (s, 1H), 7.48-6.98 (m, 4H), 6.93-6.70 (m, 2H), 5.07 (d, 2H), 4.69-3.87 (m, 4H), 3.58 (d, 2H), 2.85-2.63 (m, 5H), 2.34-2.08 (m, 2H), 1.84 (d, 2H), 1.33 (d, 6H). | 499.3 |
| 79 | 1H NMR (400 MHz, Chloroform-d) δ 13.27 (bs, 1H), 7.42-6.99 (m, 5H), 6.93-6.68 (m, 2H), 5.18-4.96 (m, 2H), 4.67-4.34 (m, 4H), 3.58 (d, 2H), 2.85-2.62 (m, 5H), 2.38-2.13 (m, 2H), 1.95-1.67 (m, 2H), 1.33 (d, 6H). | 483.3 |
| 80 | 1H NMR (400 MHz, Chloroform-d) δ 7.22-7.04 (m, 3H), 6.96-6.72 (m, 3H), 5.06 (s, 2H), 4.58-4.49 (m, 1H), 4.41 (s, 2H), 4.28-3.78 (m, 1H), 2.94 (bs, 2H), 2.32 (s, 3H), 2.20 (bs, 2H), 1.78 (bs, 2H), 1.65 (bs, 2H), 1.33 (d, 6H). | 451.0 |
| 81 | 1H NMR (400 MHz, Chloroform-d) δ 7.26 (m, 5H), 6.76 (m, 2H), 5.23-4.92 (m, 2H), 4.57 (bs, 3H), 4.37-3.80 (m, 1H), 2.94 (bs, 2H), 2.51-1.93 (m, 5H), 1.91-1.51 (m, 4H), 1.33 (d, 6H). | 483.0 |

Example 82: [4-(2-methylpropoxy)phenyl]methyl N-[(4-fluoro-2-hydroxyphenyl)methyl]-N-(1-methylpiperidin-4-yl)carbamate

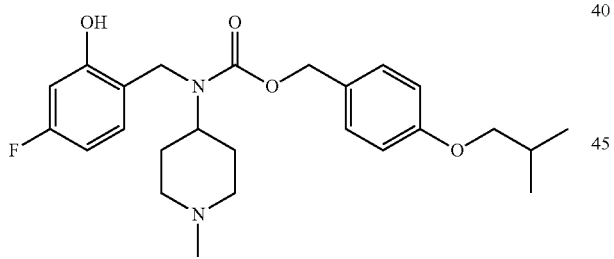

5-fluoro-2-{[(1-methylpiperidin-4-yl)amino]methyl}phenol

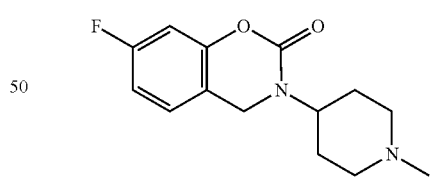

Palladium on charcoal (52 mg, 10%) was added to a solution of N-{[2-(benzyloxy)-4-fluorophenyl]methyl}-1-methylpiperidin-4-amine (74 mg, 0.23 mmol) in ethanol (5 ml), under an $N_2$ atmosphere at room temperature. The $N_2$ was exchanged for $H_2$. After 21 hours of stirring at room temperature the $H_2$ was exchanged for $N_2$ and the mixture was filtered through a plug of celite. The filtrate was concentrated to afford the desired intermediate as an oil (65 mg, quantitative).

7-fluoro-3-(1-methylpiperidin-4-yl)-3,4-dihydro-2H-1,3-benzoxazin-2-one 1,1'-Carbonyldiimidazole (55 mg, 0.34 μmol) and 4-dimethylaminopyridine (1.4 mg, 11 μmol) in dichloromethane (0.5 ml) was added to 5-fluoro-2-{[(1-methylpiperidin-4-yl)amino]methyl}phenol (27 mg, 0.11 mmol) in dichloromethane (1.5 ml). After 6 hours of stirring at room temperature the mixture was washed with NaOH (3×1 ml, 1 M aqueous), the organic phase was separated, dried using a phase separator, and concentrated to afford the desired intermediate as yellow solids (24 mg, 80%).

[4-(2-methylpropoxy)phenyl]methyl N-[(4-fluoro-2-hydroxyphenyl)methyl]-N-(1-methylpiperidin-4-yl) carbamate Sodium hydride (34 mg, 1.4 mmol) was added to [4-(2-methylpropoxy)phenyl]methanol (168 mg, 0.93 mmol) in tetrahydrofuran (0.5 ml) at room temperature. After 15 minutes 7-fluoro-3-(1-methylpiperidin-4-yl)-3,4-dihydro-2H-1,3-benzoxazin-2-one (24 mg, 91 µmol) in tetrahydrofuran (0.75 ml) was added to the mixture dropwise over 1 minute. After 1 hour the mixture was diluted with ethyl acetate (2 ml) and washed with water (2 ml). The water layer was extracted with additional ethyl acetate (2×2 ml), the combined organic phases were dried using a phase separator and concentrated to oil. The crude material was purified by column chromatography using silicon dioxide gel, eluting with 100% methanol to afford the title compound (21 mg, 52%): $^1$H NMR (400 MHz, Methanol-$d_4$) δ 7.47-6.73 (m, 5H), 6.53-6.32 (m, 2H), 5.06 (s, 2H), 4.42 (s, 2H), 3.91 (s, 1H), 3.73 (d, 2H), 2.84 (d, 2H), 2.20 (s, 3H), 2.11-1.91 (m, 3H), 1.80 (q, 2H), 1.68-1.52 (m, 2H), 1.03 (d, 6H); LCMS: 445.3 [M+H]$^+$.

TABLE 3

Additional Compounds that are synthesized using GP A

| COMPOUND # | Ar$^A$ | Ar$^B$ | R$_3$ |
|---|---|---|---|
| 83 | 2-fluoro-4-cyclopropoxyphenyl | 4-isobutoxyphenyl | methyl |
|  | 2-fluoro-4-cyclopropoxyphenyl | 4-isobutoxyphenyl | methyl |
| 84 | 2-fluoro-4-(trifluoromethoxy)phenyl | 4-isobutoxyphenyl | methyl |
|  | 2-fluoro-4-(trifluoromethoxy)phenyl | 4-isobutoxyphenyl | methyl |
| 85 | 2-fluoro-4-(2,2,2-trifluoro-1,1-dideuterioethoxy)phenyl | 4-isobutoxyphenyl | methyl |

TABLE 3-continued
Additional Compounds that are synthesized using GP A
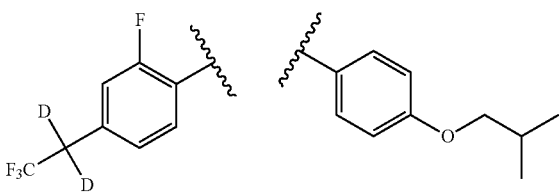
| COMPOUND # | Ar^A | Ar^B | R_3 |
|---|---|---|---|
| 86 | 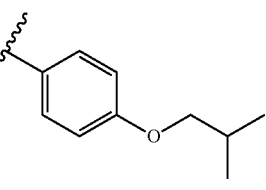 | 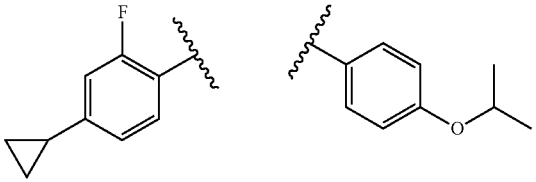 | methyl |
| 87 | 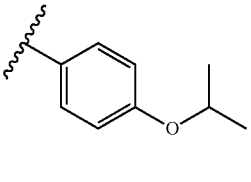 [SMILES: *c1ccc(OC(C)C)cc1] | 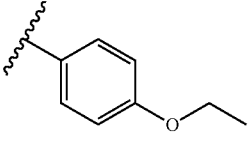 [SMILES: *c1ccc(OCC)cc1] | methyl |
| 88 | 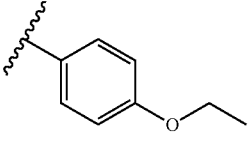 [SMILES: *c1ccc(OCC)cc1] | 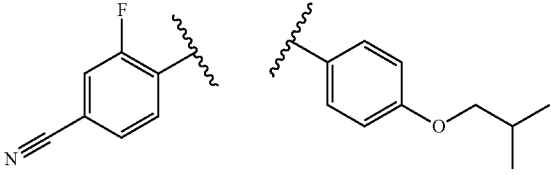 | methyl |
| 89 | 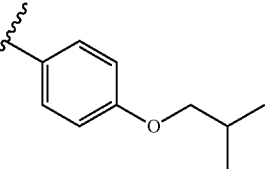 | 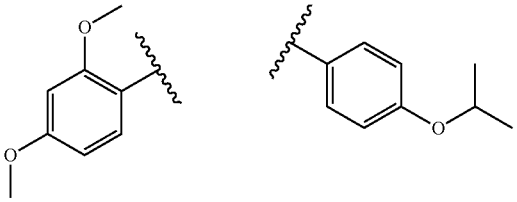 | methyl |
| 90 | 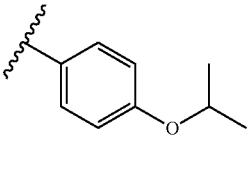 | 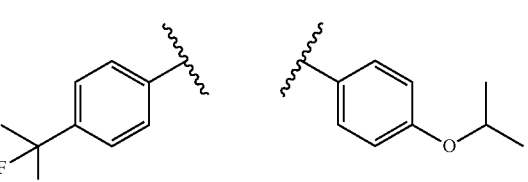 | methyl |
| 91 | 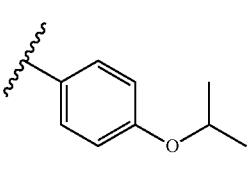 | | methyl |

TABLE 3-continued

Additional Compounds that are synthesized using GP A

| COMPOUND # | Ar$^A$ | Ar$^B$ | R$_3$ |
|---|---|---|---|
| 92 | 4-(fluoromethoxy)phenyl | 4-isobutoxyphenyl | methyl |
| 93 | 4-((1,3-difluoropropan-2-yl)oxy)phenyl | 4-ethoxyphenyl | methyl |
| 94 | 4-(2,2-difluoroethoxy)phenyl | 4-isobutoxyphenyl | methyl |
| 95 | 4-isopropoxyphenyl | 4-isopropoxyphenyl | methyl |
| 96 | 4-ethoxyphenyl | 4-isopropoxyphenyl | methyl |

TABLE 3-continued
Additional Compounds that are synthesized using GP A
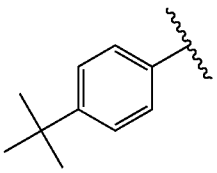 [SMILES: *c1ccc(C(C)(C)C)cc1]
| COMPOUND # | $Ar^A$ | $Ar^B$ | $R_3$ |
|---|---|---|---|
| 97 | 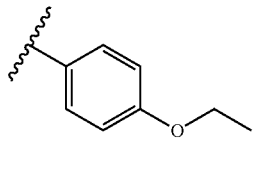 [SMILES: *c1ccc(OCC)cc1] | 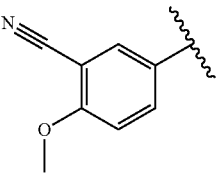 [SMILES: *c1ccc(OC)c(C#N)c1] | methyl |
| 98 | 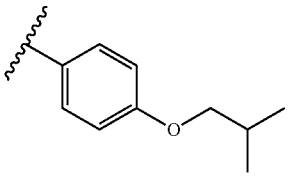 [SMILES: *c1ccc(OCC(C)C)cc1] | 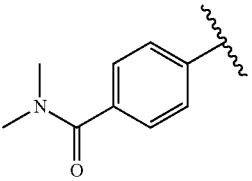 [SMILES: *c1ccc(C(=O)N(C)C)cc1] | methyl |
| 99 | 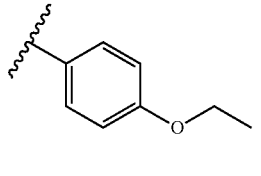 [SMILES: *c1ccc(OCC)cc1] | 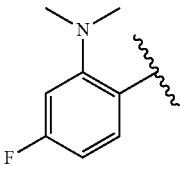 [SMILES: *c1ccc(F)cc1N(C)C] | methyl |
| 100 | 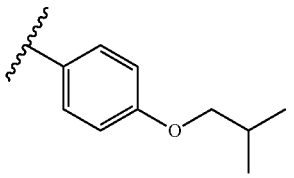 [SMILES: *c1ccc(OCC(C)C)cc1] | 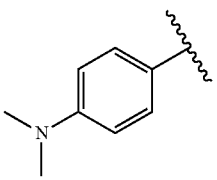 [SMILES: *c1ccc(N(C)C)cc1] | methyl |
| 101 | 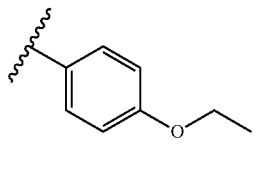 [SMILES: *c1ccc(OCC)cc1] | | methyl |

TABLE 4

Additional Compounds that are synthesized using GP B and C

| COMPOUND # | Ar$^C$ | Ar$^D$ | R$_3$ |
|---|---|---|---|
| 102 | 2-fluoro-4-cyclopropoxyphenyl | 4-isobutoxyphenyl | methyl |
| 103 | 2-fluoro-4-trifluoromethoxyphenyl | 4-isopropoxyphenyl | methyl |
| 104 | 2-fluoro-4-(1,1-dideutero-2,2,2-trifluoroethyl)phenyl | 4-isobutoxyphenyl | methyl |
| 105 | 2-fluoro-4-cyclopropylphenyl | 4-isobutoxyphenyl | methyl |
| 106 | 2-fluoro-4-methylsulfonylphenyl | 4-ethoxyphenyl | methyl |
| 107 | 2-fluoro-4-cyanophenyl | 4-ethoxyphenyl | methyl |

TABLE 4-continued
Additional Compounds that are synthesized using GP B and C
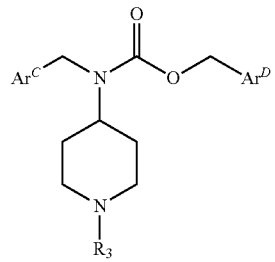
| COMPOUND # | Ar$^C$ | Ar$^D$ | R$_3$ |
|---|---|---|---|
| 108 | 2,4-dimethoxyphenyl | 4-isobutoxyphenyl | methyl |
| 109 | 4-(1,1-difluoroethyl)phenyl | 4-isobutoxyphenyl | methyl |
| 110 | 4-(fluoromethoxy)phenyl | 4-ethoxyphenyl | methyl |
| 111 | 4-((1,3-difluoropropan-2-yl)oxy)phenyl | 4-isopropoxyphenyl | methyl |
| 112 | 4-(2,2-difluoroethoxy)phenyl | 4-isopropoxyphenyl | methyl |

TABLE 4-continued
Additional Compounds that are synthesized using GP B and C
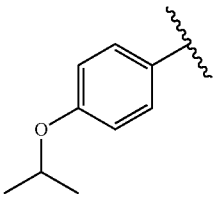 [SMILES: *c1ccc(OC(C)C)cc1]
| COMPOUND # | Ar$^C$ | Ar$^D$ | R$_3$ |
|---|---|---|---|
| 113 | 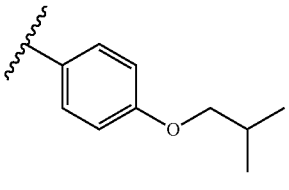 [SMILES: *c1ccc(OCC(C)C)cc1] | 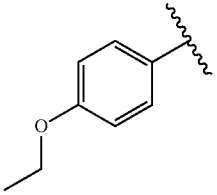 [SMILES: *c1ccc(OCC)cc1] | methyl |
| 114 | 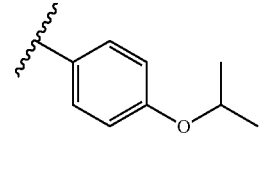 | 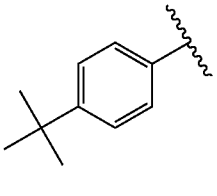 | methyl |
| 115 | 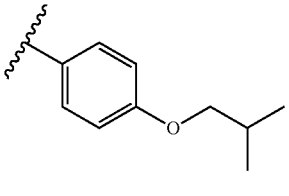 [SMILES: *c1ccc(OCC(C)C)cc1] | 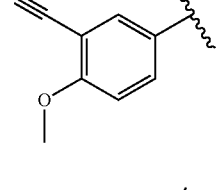 | methyl |
| 116 | 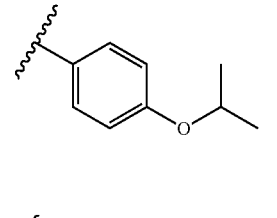 | 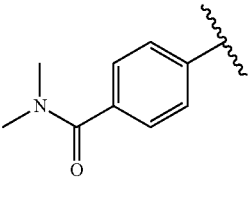 [SMILES: *c1ccc(C(=O)N(C)C)cc1] | methyl |
| 117 | 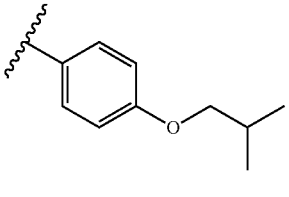 [SMILES: *c1ccc(OCC(C)C)cc1] | 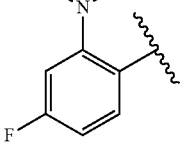 | methyl |
| 118 | 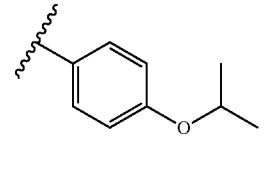 [SMILES: *c1ccc(OC(C)C)cc1] |  | methyl |

TABLE 4-continued

Additional Compounds that are synthesized using GP B and C

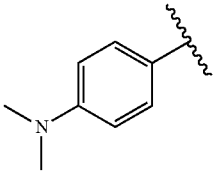 [SMILES: *c1ccc(N(C)C)cc1]

| COMPOUND # | Ar$^C$ | Ar$^D$ | R$_3$ |
|---|---|---|---|
| 119 | 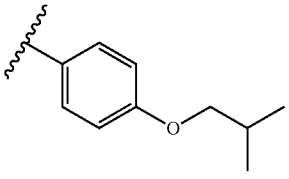 [SMILES: *c1ccc(OCC(C)C)cc1] | | methyl |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

In Vitro Determination of Receptor Activity

Receptor Selection and Amplification (R-SAT) Assays. The functional receptor assay, Receptor Selection and Amplification Technology (R-SAT®), was used (with minor modifications from the procedure described previously (Brann, M. R. U.S. Pat. No. 5,707,798, 1998; Chem. Abstr. 1998, 128, 111548) to screen compounds for activity at the 5-HT2A receptor. Briefly, NIH3T3 cells were grown in 96 well tissue culture plates to 70-80% confluence. Cells were transfected for 12-16 h with plasmid DNAs using superfect (Qiagen Inc.) as per manufacturer's protocols. R-SAT's were generally performed with 50 ng/well of receptor and 20 ng/well of β-galactosidase plasmid DNA. All receptor constructs used were in the pSI mammalian expression vector (Promega Inc) as described previously. The 5-HT2A receptor gene was amplified by nested PCR (polymerase chain reaction) from brain cDNA using the oligodcoxynuclcotides based on the published sequence (Saltzman et al., Biochem. Biophys. Res. Comm. 1991, 181, 1469). For large-scale transfections, cells were transfected for 12-16 h, then trypsinized and frozen in DMSO. Frozen cells were later thawed, plated at 10,000-40,000 cells per well of a 96 well plate that contained a compound according to Formula (I). To run functional antagonist assays, cells and compounds were additionally combined with a fixed concentration (approximately 3× the previously determined EC50) of an agonist (usually 5-CT) at 5-HT2A or other appropriate agonists for other receptors. With both methods, cells were then grown in a humidified atmosphere with 5% ambient $CO_2$ for five days. Media was then removed from the plates and marker gene activity was measured by the addition of the b-galactosidase substrate o-nitrophenyl b-D-galactopyranoside (ONPG, in PBS with 5% NP-40). The resulting colorimetric reaction was measured in a spectrophotometric plate reader (Titertek Inc.) at 420 nM. All data were analyzed using the computer program XLFit (IDBSm). Efficacy is the percent maximal repression compared to repression by a control compound (ritanserin in the case of 5-HT2A). $pIC_{50}$ is the negative of the $log(IC_{50})$, where $IC_{50}$ is the calculated concentration in molar that produces 50% maximal repression. The compounds as provided herein were assayed as described herein. Compounds of Formulas (I) and (II), demonstrated high inhibition of the 5-HT2A receptor activity as shown in the table below. This data below indicates that compounds as provide herein may be useful as pharmaceutical agents.

The data in table one may for example be interpreted using the following guidance High affinity pKi≥8.4

Moderate affinity pKi≥7.7.

TABLE 1 pKi values of exemplified compounds

| Compound No. | 5-HT2a pKi |
|---|---|
| 1 | 9.7 |
| 2 | 9.9 |
| 3a/3b | 10.0 |
| 4a/4b | 10.0 |
| 5a/5b | 9.6 |
| 6a/6b | 9.6 |
| 7a/7b | 7.4 |
| 8a/8b | 7.0 |
| 9a/9b | 7.2 |
| 10a/10b | 7.8 |
| 11 | 9.6 |
| 12 | 9.6 |
| 13 | 9.9 |
| 14 | 7.6 |
| 15 | 9.3 |
| 16 | 7.6 |
| 17 | 7.5 |
| 18 | 10.8 |
| 19 | 8.3 |
| 20 | 8.2 |
| 21 | 8.6 |
| 22 | 8.2 |
| 23 | 7.8 |
| 24 | 7.2 |
| 26 | 9.3 |
| 25 | 9.7 |
| 27 | 9.8 |
| 28 | 10.1 |
| 29 | 10.2 |
| 30 | 10.5 |
| 31 | 7.3 |
| 32 | 1 |
| 33 | 7.5 |
| 34 | 7.4 |
| 35 | 1 |
| 36 | 9.0 |
| 37 | 8.9 |
| 38 | 9.3 |
| 39 | 9.8 |
| 40 | 8.9 |
| 41 | 8.6 |
| 42 | 8.0 |
| 43 | 8.5 |
| 44 | 9.4 |
| 45 | 8.6 |
| 46 | 7.6 |
| 47 | 8.1 |
| 48 | 7.4 |
| 49 | 8.0 |
| 50 | 3.7 |
| 51 | 6.7 |
| 52 | 6.7 |
| 53 | 6.9 |
| 54 | 1 |
| 55 | 1 |
| 56 | 7.8 |
| 57 | 7.8 |
| 58 | 8.1 |
| 59 | 6.6 |
| 60 | 6.5 |
| 61 | 6.7 |
| 62 | 6.5 |
| 63 | 8.4 |
| 64 | 8.0 |
| 65 | 7.7 |
| 66 | 8.4 |
| 67 | 10.0 |
| 68 | 7.3 |

TABLE 1-continued pKi values of exemplified compounds

| Compound No. | 5-HT2a pKi |
|---|---|
| 69 | 7.7 |
| 70 | 1.0 |
| 71 | 1.0 |
| 72 | 10.0 |
| 73 | 9.4 |
| 74 | 9.1 |
| 75 | 6.8 |
| 76 | 1.0 |
| 77 | 1.0 |
| 78 | 7.6 |
| 79 | 8.4 |
| 80 | 7.8 |
| 81 | 2.7 |
| 82 | 7.8 |

What is claimed is:

1. A compound according to Formula (1)

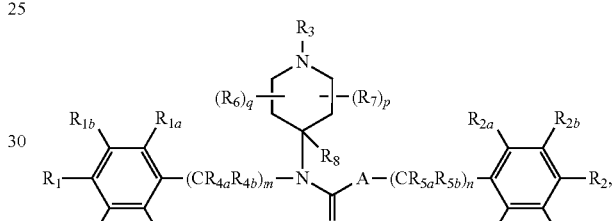

(I)

or a pharmaceutically acceptable salt; hydrate, solvate, stereoisomer, or deuterated analogue thereof, wherein:

m and n are independently an integer selected from the group consisting of 0, 1, 2, and 3;

p and q are independently an integer selected from the group consisting of 0, 1, 2, 3, and 4;

$R_1$ and $R_{1d}$ are fluoro;

$R_{1a}$, $R_{1b}$, and $R_{1c}$ are hydrogen;

$R_2$, $R_{2a}$, $R_{2b}$, $R_{2c}$ and $R_{2d}$ are independently selected from the group consisting of hydrogen, deuterium; amino, hydroxyl, -OD, halogen, cyano, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_3$-6 heteroalicyclyl, substituted or unsubstituted aryl, and substituted or unsubstituted heteroaryl, wherein at least one of $R_2$, $R_{2a}$, $R_{2b}$, $R_{2c}$ and $R_{2d}$ is not hydrogen, or $R_2$ and $R_{2b}$ or $R_{2c}$, taken together with the atoms to which they are attached form a ring system;

$R_3$ is selected from the group consisting of hydrogen, deuterium, hydroxyl, -OD, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{3-6}$ cycloalkyl, unsubstituted or substituted $C_{3-6}$ heteroalicyclyl, unsubstituted or substituted aryl, and substituted or unsubstituted heteroaryl; or $R_3$, the nitrogen to which $R_3$ is attached and a carbon atom adjacent to the nitrogen taken together with $R_6$ or $R_7$ form a heteroalicyclic ring system;

$R_{4a}$, $R_{4b}$, $R_{5a}$, and $R_{5b}$, are independently selected from the group consisting of hydrogen, deuterium, and unsubstituted or substituted $C_{1-6}$ alkyl;

$R_6$ is selected from the group consisting of hydrogen, deuterium, halogen, hydroxyl, oxo, -OD, cyano, substituted or unsubstituted $C_{1-4}$ alkyl, and substituted or unsubstituted $C_{1-4}$ alkoxy, and substituted or unsubstituted aryl;

$R_7$ is selected from the group consisting of hydrogen, deuterium, halogen, hydroxyl, oxo, -OD, cyano, substituted or unsubstituted $C_{1-4}$ alkyl, and substituted or unsubstituted $C_{1-4}$ alkoxy;

$R_8$ is absent, or selected from the group consisting of hydrogen, deuterium, cyano, hydroxyl, -OD, substituted or unsubstituted $C_{1-4}$ alkyl, substituted or unsubstituted $C_{2-4}$ alkenyl, substituted or unsubstituted $C_{3-6}$ cycloalkyl, and substituted or unsubstituted $C_{1-4}$ alkoxy;

A is —O—; and

X is O or S.

2. The compound, or pharmaceutically acceptable salt, hydrate, solvate, stereoisomer, or deuterated analogue thereof of claim 1, wherein $R_2$, $R_{2a}$, $R_{2b}$, $R_{2c}$ and $R_{2d}$ independently are selected from the group consisting of hydrogen, hydroxyl, halogen, cyano, $C_{1-6}$ alkyl, $C_{1-6}$ haloalkyl, $C_{1-6}$ alkoxy, $C_{1-6}$ haloalkoxy, $C_{3-4}$ cycloalkyl, $C_{3-4}$ cycloalkyl-$C_{1-3}$ alkyl and deuterated analogues thereof; or $R_2$ and $R_{2b}$, taken together with the phenyl ling they attach to and the atoms to which they are attached form a bicyclic fused ring system that has the following general formulae

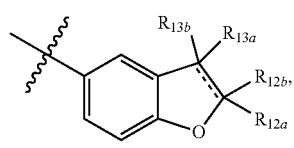

(III)

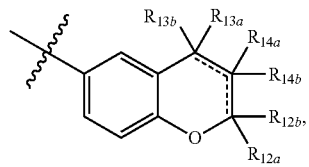

(IV)

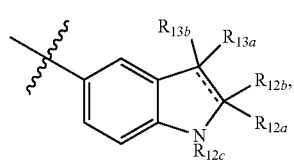

(V)

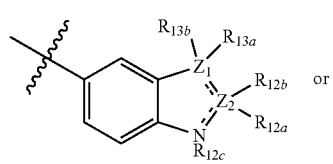

(VI)

or

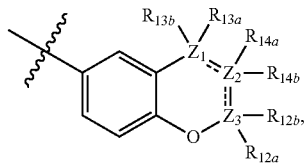

(VII)

wherein $R_{12a}$, $R_{12b}$, $R_{12c}$, $R_{13a}$, $R_{13b}$, $R_{14a}$, and $R_{14b}$ independently are absent or selected from the group consisting of hydrogen, halogen, hydroxyl, cyano, $C_{1-4}$ alkyl, and $C_{1-4}$ alkoxy, and wherein $Z_1$, $Z_2$ and $Z_3$ independently are selected from the group consisting of C, N, O and S; or $R_{2a}$, $R_{2c}$, $R_{2d}$, and $R_{2b}$, provided $R_{2b}$ is not forming a ring, system with $R_2$, independently are selected from the group consisting of hydrogen, deuterium, hydroxyl, halogen, methyl, —CD3, methoxy, —OCD$_3$, —OCF$_3$, and —CF$_3$; or $R_{2a}$, $R_{2c}$, and $R_{2b}$, provided $R_{2b}$ is not forming a ring system with $R_2$, are hydrogen, and $R_{2d}$ is hydrogen, fluoro, or hydroxyl.

3. The compound, or pharmaceutically acceptable salt, hydrate, solvate, stereoisomer, or deuterated analogue thereof of claim 1, wherein $R_2$, provided $R_2$ is not forming a ring system with $R_{2b}$, is selected from the group consisting of halogen, cyano, methyl, —CD$_3$, ethyl, —CD$_2$CD$_3$, optionally deuterated n-propyl, optionally deuterated iso-propyl, optionally deuterated n-butyl, optionally deuterated iso-butyl, optionally deuterated n-pentyl, optionally deuterated 2-methyl-butyl, optionally deuterated n-hexyl, optionally deuterated 2-methyl-pentyl, optionally deuterated methoxy, optionally deuterated ethoxy, optionally deuterated n-propoxy, optionally deuterated isopropoxy, optionally deuterated allyloxy, optionally deuterated prop-2-yn-1-yloxy, optionally deuterated n-butoxy, optionally deuterated iso-butoxy, optionally deuterated tert-butoxy, optionally deuterated pentyl-oxy, optionally deuterated 4-methyl-butoxy, optionally deuterated hexyl-oxy, optionally deuterated 4-methylpentoxy, optionally deuterated cyclopropyloxy, optionally deuterated cyclopropylmethoxy, optionally deuterated cyclopropylethoxy, optionally deuterated cyclobutyloxy, optionally deuterated cyclobutyloxy, optionally deuterated cyclobutylmethoxy, optionally deuterated cyclobutylethoxy, optionally deuterated $C_{1-6}$ haloalkoxy, —OCF$_3$, —OCF$_2$CF$_3$, —OCHF$_2$, —OCDF$_2$, —CF$_3$, —CF$_2$CF$_3$, —CHF$_2$, —CDF$_2$ —CH$_2$CF$_3$, CH$_2$F, —CF$_2$CH$_3$, 2-fluoroethoxy, 3-fluoropropoxy, 4-fluorobutoxy, (1,3-difluoropropan-2-yl) oxy, 2-hydroxyl-2-methyl-propoxy, 1,1,2,2-tetrafluorobutyl, and 1,1,1,2,2-pentafluorobutyl, or or $R_2$, provided $R_2$ is not forming a ring system with $R_{2b}$, selected from methoxy, ethoxy, n-propoxy, isopropoxy, allyloxy, prop-2-yn-1-yloxy, n-butoxy, iso-butoxy, tert-butoxy, pentyl-oxy, 4-methyl-butoxy, hexyl-oxy 4-methylpentoxy cyclopropyloxy, cyclopropylmethoxy, cyclopropylethoxy, cyclobutyloxy, cyclobutylmethoxy, cyclobutylethoxy, —CF$_2$CH$_3$, 2-fluoroethoxy, 3-fluoropropoxy, 4-fluorobutoxy, 2-hydroxyl-, 2-methyl-propoxy, 1,1-difluoroethyl, and (1,3-difluoropropan-2-yl)oxy; or $R_2$ and $R_{2b}$, taken together with the phenyl ring they attach to and the atoms to which they are attached form a bicyclic fused ring system that, has the following general formula

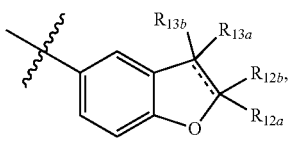

(III)

wherein $R_{12a}$ and $R_{12b}$ are hydrogen or methyl, and both $R_{13a}$ and $R_{13b}$ are hydrogen or methyl, and $R_{2a}$, $R_{2c}$, and $R_{2d}$ are hydrogen.

4. The compound, or pharmaceutically acceptable salt, hydrate, solvate, stereoisomer, or deuterated analogue thereof of claim 1, wherein $R_1$ and $R_{1d}$ are fluoro, and $R_{1a}$, $R_{1b}$ and $R_{1c}$ are hydrogen; and $R_2$ is selected from the group consisting of ethoxy, isopropoxy, allyloxy, tert-butoxy, isobutoxy, n-butoxy, cyclopropyloxy, 2-fluoroethoxy, 3-fluoropropoxy, 2-hydroxyl-2-methyl-propoxy, 1,1-difluoroethyl, and (1,3-difluoropropan-2-yl)oxy, and $R_{2a}$, $R_{2b}$, $R_{2c}$ and $R_{2d}$ are hydrogen; or $R_2$ and $R_{2b}$, taken together with the atoms to which they are attached form a heteroalicyclic ring system wherein the formed ring system, taken together with the phenyl group to which it is fused, has the following formulae

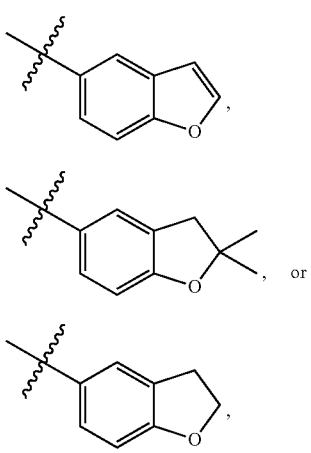

(IIIa)

, (IIIb)

, or (IIIc)

and $R_{2a}$, $R_{2c}$ and $R_{2d}$ are hydrogen.

5. The compound, or pharmaceutically acceptable salt, hydrate, solvate, stereoisomer, or deuterated analogue thereof of claim 1, wherein $R_3$ is selected from the group consisting of hydrogen, deuterium, hydroxyl, -OD, substituted or unsubstituted $C_{1-6}$ alkyl, substituted or unsubstituted $C_{1-6}$ alkoxy, substituted or unsubstituted —$(CH_2)_s$—$C_{3-6}$ cycloalkyl, substituted or unsubstituted —$(CH_2)_s$—$C_{2-5}$ heteroalicyclyl, substituted or unsubstituted —$(CH_2)_s$—$C_{2-5}$ heteroaryl, and substituted or unsubstituted —$(CH_2)_s$—$C_{5-6}$ aryl, wherein each s is selected from the group consisting of 0, 1, 2 and 3; or $R_3$ is selected from the group consisting of hydrogen, methyl, —$CD_3$, ethyl, —$CD_2CD_3$, n-propyl, —$CD_2CD_2CD_3$, iso-propyl, cyclopropyl, 3-oxetanyl, —$CDCD_3CD_3$, —$(CR_{9a}R_{9b})_tC(=O)OR_{9c}$, —$(CR_{9a}R_{9b})_t(CR_{9c}R_{9d})_wC(=O)OR_{9c}$, —$(CH_2)_t(CR_{9c}R_{9d})_wC(=O)NR_{9a}R_{9b}$ and —$(CH_2)_tC(=O)NR_{9a}R_{9b}$, wherein $R_{9a}$, $R_{9b}$, $R_{9c}$, $R_{9d}$, and $R_{9e}$ independently are hydrogen or $C_{1-4}$-alkyl, wherein each of t and w is selected from 0, 1, and 3.

6. The compound, or pharmaceutically acceptable salt, hydrate, solvate, stereoisomer, or deuterated analogue thereof of claim 1, wherein $R_3$ is hydrogen or methyl.

7. The compound, or pharmaceutically acceptable salt, hydrate, solvate, stereoisomer, or deuterated analogue thereof of claim 1, wherein $R_3$ taken together with $R_6$ or $R_7$ form a heteroalicyclic ring system according to the following formulas:

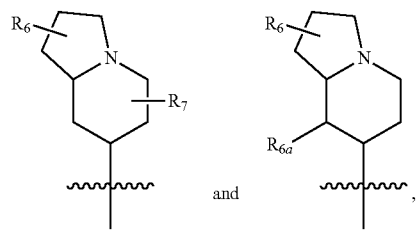

and

, wherein $R_{6a}$ is selected from the group consisting; of hydrogen, deuterium, halogen, hydroxyl, -OD, substituted or unsubstituted $C_{1-4}$ alkyl, and substituted or unsubstituted $C_{1-4}$ alkoxy.

8. The compound, or pharmaceutically acceptable salt, hydrate, solvate, stereoisomer, or deuterated analogue thereof of claim 1, wherein $R_{4a}$, $R_{4b}$, $R_{5a}$, and $R_{5b}$ are independently selected from the group consisting of hydrogen, methyl, and —$CF_3$; or $R_{4a}$, $R_{4b}$, and $R_{5a}$ are hydrogen and $R_{5b}$ is methyl or hydrogen; or $R_{4a}$, $R_{5a}$, and $R_{5b}$ are hydrogen and $R_{4b}$ is methyl or hydrogen.

9. The compound, or pharmaceutically acceptable salt, hydrate, solvate, stereoisomer, or deuterated analogue thereof of claim 1, wherein $R_{4a}$, $R_{4b}$, $R_{5a}$, and $R_{5b}$ are hydrogen.

10. The compound, or pharmaceutically acceptable salt, hydrate, solvate, stereoisomer, or deuterated analogue thereof of claim 1, wherein $R_7$ is hydrogen or fluoro.

11. The compound, or pharmaceutically acceptable salt, hydrate, solvate, stereoisomer, or deuterated analogue thereof of claim 1, wherein q is 1.

12. The compound, or pharmaceutically acceptable salt, hydrate, solvate, stereoisomer, or deuterated analogue thereof of claim 1, wherein p is 0.

13. The compound, or pharmaceutically acceptable salt, hydrate, solvate, stereoisomer, or deuterated analogue thereof of claim 1, wherein R$_8$ is selected from the group consisting of hydrogen, halogen, methyl, ethyl, propyl, methoxy, ethoxy, C$_{1-2}$-haloalkyl, and C$_{1-2}$-haloalkoxy; or R$_8$ is selected from the group consisting of hydrogen, —CF$_3$, —CHF$_2$, —CF$_2$CF$_3$, —OCF$_3$, —OCF$_2$CF$_3$ and —OCHF$_2$; or R$_8$ is hydrogen.

14. The compound, or pharmaceutically acceptable salt, hydrate, solvate, stereoisomer, or deuterated analogue thereof of claim 1, wherein X is O.

15. The compound, or pharmaceutically acceptable salt, hydrate, solvate, stereoisomer, or deuterated analogue thereof of claim 1; wherein m is 1 and n is 0 or 1.

16. The compound, or pharmaceutically acceptable salt, hydrate, solvate, stereoisomer, or deuterated analogue thereof of claim 1, wherein the compound is a compound according to Formula (II)

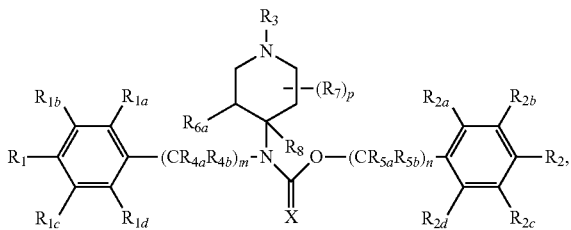

(II)

wherein R$_{6a}$ is selected from the group consisting of hydrogen, deuterium, halogen, hydroxyl, -OD, substituted or unsubstituted C$_{1-4}$ alkyl, and substituted or unsubstituted C$_{1-4}$ alkoxy.

17. A compound, pharmaceutically acceptable salt, polymorph, or stereoisomer selected from the group consisting of:

[4-(propan-2-yloxy)phenyl]methyl N-[(2,4-difluorophenyl)methyl]-N-(piperidin-4-yl)carbamate;

[4-(propan-2-yloxy)phenyl]methyl N-[(2,4-difluorophenyl)methyl]-N-(1-methylpiperidin-4-yl)carbamate;

[4-(2-methylpropoxy)phenyl]methyl N-[(2,4-difluorophenyl)methyl]-N-(1-methylpiperidin-4-yl)carbamate;

(4-methoxyphenyl)methyl N-[(2,4-difluorophenyl)methyl]-N-(1-methylpiperidin-4-yl)carbamate;

N-[(2,4-difluorophenyl)methyl]-N-(1-methylpiperidin-4-yl){[(4-methoxyphenyl)methyl]sulfanyl}formamide;

4-(allyloxy)benzyl (2,4-difluorobenzyl)(1-methylpiperidin-4-yl)carbamate, 4-ethoxybenzyl (2,4-difluorobenzyl)(1-methylpiperidin-4-yl)carbamate;

4-(3-fluoropropoxy)benzyl (2,4-difluorobenzyl)(1-methylpiperidin-4-yl)carbamate;

4-((1,3-difluoropropan-2-yl)oxy)benzyl (2,4-difluorobenzyl)(1-methylpiperidin-4-yl)carbamate;

4-(2-hydroxy-2-methylpropoxy)benzyl (2,4-difluorobenzyl)(1-methylpiperidin-4-yl)carbamate;

4-cyclopropoxybenzyl (2,4-difluorobenzyl)(1-methylpiperidin-4-yl)carbamate;

[4-(2-fluoroethoxy)phenyl]methyl N-[(2,4-difluorophenyl)methyl]-N-(1-methylpiperidin-4-yl)carbamate;

(4-butoxyphenyl)methyl N-[(2,4-difluorophenyl)methyl]-N-(1-methylpiperidin-4-yl)carbamate;

methyl 3-(4-}[(2,4-difluorophenyl)methyl](}[4-(propan-2-yloxy)phenyl]methoxy}carbonyl)amino}piperidin-1-yl)-2,2-dimethylpropanoate;

3-(4-{[(2,4-difluorophenyl)methyl]({[4-(propan-2-yloxy)phenyl]-methoxy}carbonyl)amino}piperidin-1-yl)-2,2-dimethylpropanoic acid;

[4-(propan-2-yloxy)phenyl]methyl N-[(2,4-difluorophenyl)methyl]-N-(1-ethylpiperidin-4-yl)carbamate;

[4-(propan-2-yloxy)phenyl]methyl N-(1-cyclopropylpiperidin-4-yl)-N-[(2,4-difluorophenyl)methyl]carbamate;

[4-(propan-2-yloxy)phenyl]methyl N-[(2,4-difluorophenyl)methyl]-N-[1-(oxetan-3-yl)piperidin-4-yl]carbamate;

(2E)-N-[(2,4-difluorophenyl)methyl]-N-(1-methylpiperidin-4-yl)-3-[4-(propan-2-yloxy)phenyl]prop-2-enamide;

N-[(2,4-dichlorophenyl)methyl]-N-(1-methylpiperidin-4-yl)-2[4-(2-methylpropoxy)phenyl]acetamide;

N-[(2,4-dichlorophenyl)methyl]-N-(1-methylpiperidin-4-yl)-2-[4-(propan-2-yloxy)phenyl]acetamide;

4-(tert-butoxy)benzyl (2,4-difluorobenzyl)(1-methylpiperidin-4-yl)carbamate; and 4-(1,1-difluoroethyl)benzyl (2,4-difluorobenzyl)(1-methylpiperidin-4-yl)carbamate.

* * * * *